United States Patent [19]
Nakao et al.

[11] Patent Number: 5,466,691
[45] Date of Patent: Nov. 14, 1995

[54] THIOPHENE COMPOUND

[75] Inventors: Tohru Nakao; Yuji Ono; Hiroshi Tanaka; Minoru Obata, all of Fukuoka; Yasuto Morimoto, Osaka, all of Japan

[73] Assignee: Yoshitomi Pharmaceutical Industries, Ltd., Osaka, Japan

[21] Appl. No.: 39,100

[22] PCT Filed: Aug. 5, 1992

[86] PCT No.: PCT/JP92/01002

§ 371 Date: Mar. 30, 1993

§ 102(e) Date: Mar. 30, 1993

[87] PCT Pub. No.: WO93/03025

PCT Pub. Date: Feb. 18, 1993

[30] Foreign Application Priority Data

Aug. 9, 1991 [JP] Japan ................................. 3-225230
Jan. 23, 1992 [JP] Japan ................................. 4-032611

[51] Int. Cl.$^6$ ................. C07D 409/00; C07D 419/00; C07D 411/00; A61K 31/495; A61K 31/445
[52] U.S. Cl. ................. 514/254; 514/252; 514/321; 514/326; 514/328; 544/295; 544/368; 544/379; 546/198; 546/209; 546/212; 546/213
[58] Field of Search ..................... 544/368, 295, 544/379; 546/213, 198, 209, 212; 514/254, 321, 328, 252, 326

[56] References Cited

U.S. PATENT DOCUMENTS

| | | | |
|---|---|---|---|
| 3,171,838 | 3/1965 | Janssen et al. | 514/329 |
| 3,806,526 | 4/1974 | Carr | 546/198 |
| 3,919,243 | 11/1975 | Hydro | 514/327 |
| 4,032,531 | 6/1977 | Hydro | 514/327 |
| 4,123,529 | 10/1978 | Verge et al. | 544/369 |
| 4,246,267 | 1/1981 | Vincent | 546/224 |
| 4,482,718 | 11/1984 | Chekroun et al. | 546/284 |
| 4,487,931 | 12/1984 | Chekroun et al. | 546/280 |
| 5,198,457 | 3/1993 | Yarrington | 514/392 |

FOREIGN PATENT DOCUMENTS

| | | |
|---|---|---|
| 2053759 | 11/1970 | Germany . |
| 1096341 | 12/1967 | United Kingdom . |
| 1294720 | 11/1972 | United Kingdom . |
| 1413138 | 11/1975 | United Kingdom . |

OTHER PUBLICATIONS

J. M. Luteijn et al, Tetrahedro vol. 44, No. 18, pp. 5921–5928 (1988).

*Primary Examiner*—Cecilia Trang
*Attorney, Agent, or Firm*—Wenderoth, Lind & Ponack

[57] ABSTRACT

Thiophene compounds of the formula

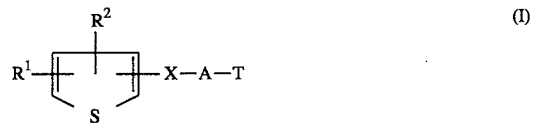

wherein each symbol is as defined in the specification, their pharmaceutically acceptable salts, pharmaceutical compositions containing said compound and additives for pharmaceuticals, and antipsychotics containing said compound as an active ingredient.

The compound of the present invention has pharmacological actions required of antipsychotic, such as motility suppressing action, anti-apomorphine action, mothamphetamine antagonistic action, tetrabenazine-induced blepharoptosis enhancing action, and the like. The compound of the present invention is useful as an antipsychotic having less extrapyramidal side-effects or a non-benzodiazepine type antianxiety agent.

9 Claims, No Drawings

THIOPHENE COMPOUND

TECHNICAL FIELD

This is a 371 application of PCT/JP92/01002, filed Aug. 5, 1992.

The present invention relates to novel thiophene compounds useful as pharmaceuticals and their pharmaceutically acceptable salts.

BACKGROUND ART

Up to the present, there have been developed a large number of psychotropic agents for the therapy of anxiety neurosis, schizophrenia, depression, etc. Yet, most of these drugs accompany various side-effects upon continuous administration, or the like, such as excessive sedation, addiction, dyskinesia and Parkinson disease, and they are not entirely satisfactory.

Meanwhile, Tetrahedron 44(18), 5921–5928 (1988) teaches methods for synthesizing 5-acetyl-3-cyano-2-(2-diethylaminoethyl)thio-4-phenylthiophene and 5-benzoyl-4-chloro-3-cyano-2((2-dimethylaminoethyl)thio)thiophene. Eur. J. Med. Chem. Chim. Ther. 12(6), 557–563 (1977)teaches 2-((2-piperidinoethyl)thio)thiophene, 2-((2-morpholinoethyl)thio)thiophene, and others having an antiviral activity. Japanese Patent Unexamined Publication No. 133989/1977 discloses compounds such as 1-[2-(2thienylthio)ethyl] -4-(N-phenyl-N-propionylamino)piperidine having a hypotensive action. Japanese Patent Unexamined Publication No. 81582/1981 discloses N-[3-[[5-(dimethylamino)-methyl-4-methyl-2-thienyl]thio]propyl]-isoindole-1,3(2H)-dione as a synthetic intermediate of a compound having a histamine $H_2$ antagonistic action. Also, Chemical Abstracts 112(9): 77137p shows N-[2-(2-thienylthio)ethyl]-2-oxo-5-hydroxypyrrolidine. However, there have not been reported action of these compounds on the central nervous system.

Japanese Patent Unexamined Publication No. 115568/1985 discloses methyl (2RS, 5R)-3-[2-(5-carbamoyl-2-thienyl)ethyl]-5-phenyl-2 oxazolidinecarboxylate having an antidiabetic effect. Japanese Patent Unexamined Publication No. 213278/1989 discloses 1-[2-(2-thienyl)ethyl]-4-(2-ethyl-1,3,4-oxadiazol-5-yl)-4-(N-phenylpropionamido)piperidine having an analgesic action. Yakugaku Zasshi 104(6), 680–690 (1984) reports 3-[2-(5-acetyl-2-thienyl)ethyl] -2,4-oxazolidincdione, etc. having an antiulcer action. Furthermore, Japanese Patent Unexamined Publication Nos. 185777/1985 and 45381/1989, US Patent No. 4032531, Japanese Patent Unexamined Publication Nos. 151183/1977, 93334/1974 and 40582/1975, US Patent No. 3919243, Japanese Patent Examined Publication No. 14557/1967, U.S. Pat. No. 3171838, UK Patent No. 1294720, and Japanese Patent Unexamined Publication Nos. 85576/1973, 85578/1973 and 206558/1983 disclose thiophene compounds. However, these compounds have not been reported as having an action on central nervous system.

As a compound having a psychotropic action, Japanese Patent Unexamined Publication No. 156879/1977 reports 4-2-(4- acetylaminomethylphenyl)ethyl-1-phenylpiperazine.

DISCLOSURE OF THE INVENTION

The present inventors have made intensive studies with the aim of developing a psychotropic agent having less side-effects and found a novel thiophenc compound exhibiting superior actions, which resulted in the completion of the invention.

That is, the present invention relates to:
1. a thiophene compound of the formula

wherein;

$R^1$ and $R^2$ are the same or different, and each is a hydrogen, a halogen, a nitro, an amino, a cyano, an alkyl, a mono- or di-substituted amino, a formyl, -COOR$^3$ ($R^3$ is a hydrogen, an alkyl or an ester residue hydrolyzablc in the body), an alkoxy, a hydroxyalkyl, a haloalkyl, a haloalkoxy, an alkanoyl, an aroyl, an arylalkanoyl, an alkanoyloxyalkyl, an aroyloxyalkyl, a formylamino, an alkanoylamino, an arylalkanoylamino, an aroylamino, a formylaminoalkyl, an alkanoylaminoalkyl, a haloalkanoylaminoalkyl, an arylalkanoylaminoalkyl, an aroylaminoalkyl, an arylalkyl, a carbamoyl, a mono- or di-substituted carbamoyl, a carbamoylalkyl, a mono- or di-substituted carbamoylalkyl, an aminoalkyl, a mono- or di-substituted aminoalkyl, an alkylsulfonylaminoalkyl, a hydroxyiminoalkyl or an alkoxyiminoalkyl;

X is -S(O)$_n$- (n is 0, 1 or 2), -CO-, -CH(OR$^{10}$)- (R$^{10}$ is a hydrogen, an alkyl or an acyl), -C$_2$-, -C(=NOR$^{11}$)- (R$^{11}$ is a hydrogen, an alkyl or an acyl), or -CH(NH$_2$)-;

A is an alkylene;

T is -NHR$^4$ (R$^4$ is a hetcroarylalkyl which may be hydrogenated),

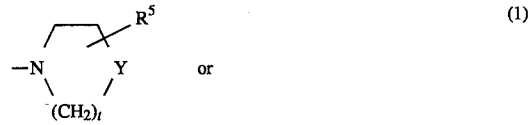

wherein t is an integer of 1–4, $R^5$ is a hydrogen, a hydroxyl group, an alkyl, an alkoxy or a carbamoyl, Y is C($R^6$)($R^7$) ($R^6$ is a hydrogen, a hydroxyl group, a carbamoyl, a mono- or di-substituted carbamoyl or an alkyl, and $R^v$ is a hydroxyl group, an alkyl, a cyanoalkyl, a hydroxyalkyl, an aryl, an arylalkyl, an alkoxycarbonyl, a diarylalkyl, a heteroaryl, a heteroarylalkyl, a heteroarylcarbonyl, a cycloalkyl, a cycloalkylalkyl, an alkanoyl, an aroyl, an aroylamino, an amino, a mono- or disubstituted amino or a cyclic amino, or $R^6$ and $R^7$ may form a bisarylmethylene), or N-$R^8$ ($R^8$ is an alkyl, a carbamoyl, a mono- or di-substituted carbamoyl, a cyanoalkyl, a hydroxyalkyl, an aryl, an arylalkyl, an alkoxycarbonyl, a diarylalkyl, a heteroaryl, a heteroarylalkyl, a heteroarylcarbonyl, a cycloalkyl, a cycloalkylalkyl, an alkanoyl, an aroyl or a cinnamyl), and the ring Am in the formula (2) is a 5 to 7-membered ring having an amide bond in the ring, which may further have an oxygen atom, a sulfur atom, a carbonyl and/or N-$R^9$ ($R^9$ is a hydrogen, an alkyl or an aryl), and may be condensed with a 5 to 7-membered saturated or unsaturated ring;

In the above definitions, the group having a cycloalkyl, an aryl or a heteroaryl may have 1 to 5 substituents on its ring; provided that when X is -CO-, -CH(OR$^{10}$)- ($R^{10}$ is a hydrogen, an alkyl or an acyl), -CH$_2$-, -C(=NOR$^{11}$)- (R$^{11}$ is a hydrogen, an alkyl or an acyl) or -CH(NH$_2$)-, T is represented by the formula (1), t is 2 or 3, R$^5$ is a hydrogen, and Y is any one of the following, at least either R$^1$ or R$^2$ is a group other than a hydrogen, a halogen, a nitro, an alkoxy and an alkyl;

(i) Y is C(R$^6$)(R$^7$) (R$^6$ is a hydroxyl group and R$^7$ is an aryl or an arylalkyl)

(ii) Y is C(R$^6$)(R$^7$) (R$^6$ is a hydrogen and R$^7$ is a diarylalkyl)

(iii) Y is C(R$^6$)(R$^7$) (R$^6$ and R$^7$ form a bisarylmethylene)

(iv) Y is N-R$^8$ (R$^8$ is an alkyl, an aryl, an arylalkyl, a heteroarylalkyl, a diarylalkyl, a cycloalkylalkyl or an aroyl; or its pharmaceutically acceptable salt, 2. the thiophene compound as described in 1. above, wherein;

R$^1$ and R$^2$ are the same or different, and each is a hydrogen, a halogen, a nitro, an amino, a cyano, an alkyl, a mono- or di-substituted amino, a formyl, -COOR$^3$ (R$^3$ is a hydrogen, an alkyl or an ester residue hydrolyzable in the body), an alkoxy, a hydroxyalkyl, a haloalkyl, an alkanoyl, an aroyl, an arylalkanoyl, an alkanoylamino, an arylalkanoylamino, an aroylamino, an alkanoylaminoalkyl, a haloalkanoylaminoalkyl, an arylalkanoylaminoalkyl, an aroylaminoalkyl, an arylalkyl, a carbamoyl, a mono- or di-substituted carbamoyl, a carbamoylalkyl, a mono- or di-substituted carbamoylalkyl, an aminoalkyl, a monoor di-substituted aminoalkyl, an alkylsulfonylaminoalkyl, a hydroxyiminoalkyl or an alkoxyiminoalkyl;

X is -S(O)$_n$- (n is 0, 1 or 2), -CO-, -CH(OR$^{10}$)- (R$^{10}$ is a hydrogen, an alkyl or an acyl), -CH$_2$-, -C(=NOR$^{11}$)- (R$^{11}$ is a hydrogen, an alkyl or an acyl), or -CH(NH$_2$)-;

A is an alkylene;

T is -NHR$^4$ (R$^4$ is a heteroarylalkyl which may be hydrogenated),

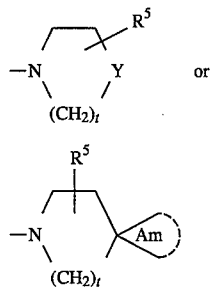

wherein t is an integer of 1–4, R$^4$ is a hydrogen or a hydroxyl group, Y is C(R$^6$)(R$^7$) (R$^6$ is a hydrogen, a hydroxyl group or a carbamoyl, and R$^7$ is an aryl, an arylalkyl, a diarylalkyl, a heteroaryl, a hetcroarylalkyl, a heteroarylcarbonyl, an alkanoyl, an aroyl, an aroylamino, an amino, a mono- or di-substituted amino or a cyclic amino, or R$^6$ and R$^7$ may form a bisarylmethylene), or N-R$^8$ (R$^8$ is an alkyl, a carbamoyl, monoor di-substitutcd carbamoyl, an aryl, an arylalkyl, a diarylalkyl, a heteroaryl, a heteroarylalkyl, a hetcroarylcarbonyl, an alkanoyl or an aroyl), and the ring Am in the formula (2) is a 5 to 7-membcrcd ring having an amide bond in the ring, which may further have an oxygen atom, a sulfur atom, a carbonyl and/or N-R$^9$ (R$^9$ is a hydrogen, an alkyl or an aryl), and may be condensed with a 5 to 7-membered saturated or unsaturated ring;

In the above definitions, the group having an aryl or a heteroaryl may have 1 to 5 substituents on its ring; provided that when X is -CO-, -CH(OR$^{10}$)- (R$^{10}$ is a hydrogen, an alkyl or an acyl), -CH$_2$-, -C(=NOR$^{11}$)- (R$^{11}$ is a hydrogen, an alkyl or an acyl), or -CH(NH$_2$)-, T is represented by the formula (1), t is 2 or 3, R$^5$ is a hydrogen, and Y is any one of the following, at least either R$^1$ or R$^2$ is a group other than a hydrogen, a halogen, a nitro, an alkoxy and an alkyl;

(i) Y is C(R$^6$)(R$^7$) (R$^e$ is a hydroxyl group and R$^7$ is an aryl or an arylalkyl)

(ii) Y is C(R$^6$)(R$^7$) (R$^6$ is a hydrogen and R$^7$ is a diarylalkyl)

(iii) Y is C(R$^6$)(R$^7$) (R$^6$ and R$^7$ form a bisarylmethylene)

(iv) Y is N-R$^8$ (R$^8$ is an alkyl, an aryl, an arylalkyl, a heteroarylalkyl, a diarylalkyl or an aroyl); or its pharmaceutically acceptable salt, 3. the thiophene compound as described in 1. above, wherein;

R$^1$ and R$^2$ are the same or different, and each is a hydrogen, a halogen, a cyano, an alkyl, a formyl, a hydroxyalkyl, a haloalkyl, an alkanoyl, an aroyl, an alkanoylamino, an alkanoylaminoalkyl, a haloalkanoylaminoalkyl, an arylalkanoylaminoalkyl, an aroylaminoalkyl, a carbamoylalkyl, a mono- or disubstituted carbamoylalkyl, an aminoalkyl, a mono- or di-substituted aminoalkyl, an aikylsulfonylaminoalkyl or a hydroxyiminoalkyl;

X is -S(O)$_n$- (n is 0, 1 or 2), -CO-, -CH(OR$^{10}$)- (R$^{10}$ is a hydrogen, an alkyl or an acyl), or -CH$_2$-;

A is an alkylene;

T is

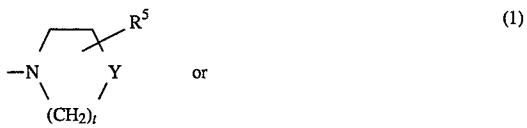

wherein t is an integer of 1–4, R$^5$ is a hydrogen or a hydroxyl group, Y is C(R$^6$)(R$^7$) (R$^6$ is a hydrogen, a hydroxyl group or a carbamoyl, and R$^7$ is an aryl, an arylalkyl, a diarylalkyl, a heteroaryl, a heteroarylalkyl, a heteroarylcarbonyl, an aroyl or a cyclic amino, or R$^6$ and R$^7$ may form a bisarylmethylene), or N-R$^8$ (R$^8$ is an alkyl, a carbamoyl, a mono- or di-substituted carbamoyl, an aryl, an arylalkyl, a diarylalkyl or a heteroaryl), and the ring Am in the formula (2) is a 5 to 7-membered ring having an amide bond in the ring, which may further have a carbonyl and/or N-R$^9$ (R$^9$ is hydrogen or an alkyl), and may be condensed with a 5 to 7-membcred saturated or unsaturated ring;

In the above definitions, the group having an aryl or a heteroaryl may have 1 to 5 substituents on its ring;

provided that when X is -CO-, -CH(OR$^{10}$)- (R$^{10}$ is a hydrogen, an alkyl or an acyl), or -CH$_2$-, T is represented by the formula (1), t is 2 or 3, R$^5$ is a hydrogen, and Y is any one of the following, at least either R$^1$ or R$^2$ is a group other than a hydrogen, a halogen and an alkyl;

(i) Y is C(R$^6$)(R$^7$) (R$^6$ is a hydroxyl group and R$^7$ is an aryl or an arylalkyl )

(ii) Y is C(R$^6$)(R$^7$) (R$^6$ is a hydrogen and R$^7$ is a diarylalkyl)

(iii) Y is C(R$^6$)(R$^7$) (R$^6$ and R$^7$ form a bisarylmethylene)

(iv) Y is N-R$^8$ (R$^8$ is an alkyl, an aryl, an arylalkyl or a diarylalkyl); or its pharmaceutically acceptable salt, 4. the thiophene compound as described in 1. above, wherein;

R$^1$ is a formyl, a hydroxyalkyl, a haloalkyl, an alkanoyl, an aroyl, an alkanoylamino, an alkanoylaminoalkyl, a haloalkanoylaminoalkyl, an arylalkanoylaminoalkyl, an aroylaminoalkyl, a carbamoylalkyl, a mono- or di-substituted carbamoylalkyl, an aminoalkyl, a mono- or di-substituted aminoalkyl, an alkylsulfonylaminoalkyl or a hydroxyiminoalkyl;

$R^2$ is a hydrogen, a halogen, a nitro, a cyano or an alkyl;

X is -S(O)$_n$- (n is 0, 1 or 2), -CO-, -CH(OR$^{10}$)- (R$^{10}$ is a hydrogen, an alkyl or an acyl) or -CH$_2$-;

A is an alkylene;

T is

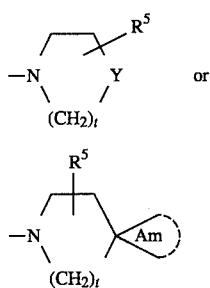

wherein t is an integer of 1–4, $R^5$ is a hydrogen or a hydroxyl group, Y is C(R$^6$)(R$^7$) (R$^6$ is a hydrogen, a hydroxyl group or a carbamoyl, and R$^7$ is an aryl, an arylalkyl, a diarylalkyl, a heteroaryl, heteroarylalkyl, heteroarylcarbonyl, an aroyl or a cyclic amino, or R$^6$ and R$^7$ may form a bisarylmethylene), or N-R$^8$ (R$^8$ is an alkyl, a carbamoyl, a mono- or di-substituted carbamoyl, an aryl, an arylalkyl, a diarylalkyl or a heteroaryl), and the ring Am in the formula (2) is a 5 to 7-membered ring having an amide bond in the ring, which may further have a carbonyl and/or N-R$^9$ (R$^9$ is a hydrogen or an alkyl), and may be condensed with a 5 to 7-membered saturated or unsaturated ring;

In the above definitions, the group having an aryl or a heteroaryl may have 1 to 5 substituents on its ring; or its pharmaceutically acceptable salt, 5. the thiophene compound as described in 1. above which is preferably selected from 3-(4-(3-((5-acetyl-2-thienyl)thio)- propyl)-1-piperazinyl)-1,2-benzisothiazole, 3-(1-(3-((5-acetyl-2-thienyl) thio)propyl)piperidin-4-yl)-6-fluoro-1,2-benzisoxazole, 3-(1-(3-((5-acetylamino-2-thienyl)thio)propyl)piperidin-4-yl)-6 -fluoro-1,2 benzisoxazole, 3-(1-(8-((5-acetylaminomethyl-2-thienyl) thio)propyl)piperidin-4-yl)-6-fluoro-1,2-benzisoxazole, 3-(1-(4-(5-acetylaminomethyl-2-thienyl)-4-oxobutyl)piperidin-4-yl) -6-fluoro-1,2-benzisoxazole, 3-(1-(4-(5-acetylaminomethyl-2-thienyl) butyl)piperidin-4-yl)-6-fluoro-1,2-benzisoxazole, 3-(1 (2-(5-acetylaminomethyl-2-thienyl)ethyl)piperidin-4-yl)-6-fluoro-1,2 -benzisoxazole, 3-(1-(2-(5-acetylaminomethyl-4-methyl 2-thienyl)ethyl)piperidin-4-yl)-6-fluoro-1,2-benzisoxazole, 3 (1-(2-(5-acetylaminomethyl-2-methyl-3-thienyl)ethyl))piperidin-4-yl) -6-fluoro-1,2-benzisoxazole, 3-(1-(2-(5-(2-acetylaminoethyl) 2-thienyl)ethyl)piperidin-4-yl)-6-fluoro-1,2-benzisoxazole, 3 (1-(2-(5-(2-acetylaminoethyl)-4-bromo-2-thienyl)ethyl)piperidin 4-yl)-6-fluoro-1,2-benzisoxazole, 3-(1-(4-(5-acetylamino-2-thienyl) butyl)piperidin-4-yl)-6-fluoro-1, 2-benzisoxazole, and their pharmaceutically acceptable salts, 6. a pharmaceutical composition containing the compound as described in 1. above and additives for pharmaceuticals, 7. an antipsychotic containing, as an active ingredient, the compound as described in 1. above, 8. a thiophene compound of the formula

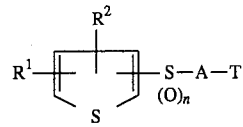

wherein;

$R^1$ and $R^2$ are the same or different, and each is a hydrogen, a halogen, a nitro, an amino, an alkyl, a mono- or di-substituted amino, a formyl, -COOR$^3$ (R$^3$ is a hydrogen, an alkyl or an ester residue hydrolyzable in the body), an alkoxy, a hydroxyalkyl, a haloalkyl, a haloalkoxy, an alkanoyl, an aroyl, an arylalkanoyl, an alkanoyloxyalkyl, an aroyloxyalkyl, a formylamino, an alkanoylamino, an arylalkanoylamino, an aroylamino, an aralkyl, a carbamoyl, a mono- or di-substituted carbamoyl, a hydroxyiminoalkyl, an alkoxyiminoalkyl, an aminoalkyl or a mono- or di-substituted aminoalkyl;

n is 0, 1 or 2;

A is an alkylene;

T is -NHR$^4$ (R$^4$ is a hetcroarylalkyl which may be hydrogenated),

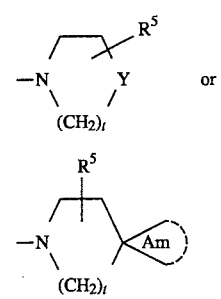

wherein t is an integer of 1–4, $R^5$ is a hydrogen, a hydroxyl group, an alkyl, an alkoxy or a carbamoyl, Y is C(R$^6$)(R$^7$) (R$^6$ is a hydrogen, a hydroxyl group, a carbamoyl, a mono- or di-substituted carbamoyl or an alkyl, and R$^7$ is a hydroxyl group, an alkyl, a cyanoalkyl, a hydroxyalkyl, an aryl, an arylalkyl, an alkoxycarbonyl, a diarylalkyl, a heteroaryl, a heteroarylalkyl, a heteroarylcarbonyl, a cycloalkyl, a cycloalkylalkyl, an alkanoyl, an aroyl, an aroylamino, an amino, a mono- or di-substituted amino or a cyclic amino, or R$^6$ and R$^7$ may form a bisarylmethylene), or N-R$^8$ (R$^8$ is alkyl, a cyanoalkyl, a hydroxyalkyl, an aryl, an arylalkyl, an alkoxycarbonyl, a diarylalkyl, a heteroaryl, a heteroarylalkyl, a heteroarylcarbonyl, a cycloalkyl, a cycloalkylalkyl, an alkanoyl, an aroyl or a cinnamyl), and the ring Am in the formula (2) is a 5 to 7-membered ring having an amide bond in the ring, which may further have an oxygen atom, a sulfur atom, a carbonyl and/or N-R$^9$ (R$^9$ is a hydrogen, an alkyl or an aryl), and may be condensed with a 5 to 7-membered saturated or unsaturated ring;

In the above definitions, the group having an aryl or a heteroaryl may have 1 to 5 substituents on its ring; or its pharmaceutically acceptable salt, and 9. a thiophene compound of the formula

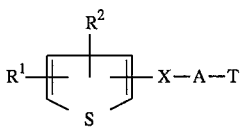

wherein;

$R^1$ and $R^2$ are the same or different, and each is a hydrogen, a halogen, a nitro, an amino, an alkyl, a mono- or di-substituted amino, a formyl, -COOR$^3$ ($R^3$ is a hydrogen, an alkyl or an ester residue hydrolyzable in the body), an alkoxy, a hydroxyalkyl, a haloalkyl, a haloalkoxy, an alkanoyl, an aroyl, an arylalkano yl, an alkanoyloxyalkyl, an aroyloxyalkyl, a formylamino, an alkanoylamino, an arylalkanoylamino, an aroylamino, a formylaminoalkyl, an alkanoylaminoalkyl, a haloalkanoylaminoalkyl, an arylalkanoylaminoalkyl, an aroylaminoalkyl, an arylalkyl, a carbamoyl, a mono- or di-substituted carbamoyl, a carbamoylalkyl, a mono- or di-substituted carbamoylalkyl, an aminoalkyl, a mono- or di-substituted aminoalkyl or an alkylsulfonylaminoalkyl;

X is -CO-, -CH(OR$^{10}$)- ($R^{10}$ is a hydrogen, an alkyl or an acyl), -CH$_2$-, -C(=NOR$^{11}$)- ($R^{11}$ is a hydrogen, an alkyl or an acyl), or -CH(NH$_2$)-;

A is an alkylene;

T is -NHR$^4$ ($R^4$ is a heteroarylalkyl which may be hydrogenated),

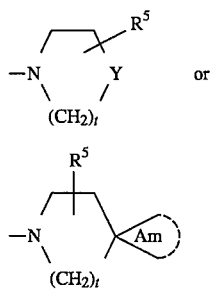

wherein t is an integer of 1–4, $R^5$ is a hydrogen, a hydroxyl group, an alkyl, an alkoxy or a carbamoyl, Y is C(R$^6$)(R$^7$) ($R^6$ is a hydrogen, a hydroxyl group, a carbamoyl, a mono- or di-substituted carbamoyl or an alkyl, and $R^7$ is a hydroxyl group, an alkyl, a cyanoalkyl, a hydroxyalkyl, an aryl, an arylalkyl, an alkoxycarbonyl, diarylalkyl, a heteroaryl, a heterorylalkyl, a heteroarylcarbonyl, a cycloalkyl, a cycloalkylalkyl, an alkanoyl, an aroyl, an aroylamino, an amino, a mono- or di-substituted amino or a cyclic amino, or $R^6$ and $R^7$ may form a bisarylmethylene), or N-R$^8$ ($R^8$ is an alkyl, a cyanoalkyl, a hydroxyalkyl, an aryl, an arylalkyl, an alkoxycarbonyl, diarylalkyl, a heteroaryl, a heteroarylalkyl, a heteroarylcarbonyl, a cycloalkyl, a cycloalkylalkyl, an alkanoyl, an aroyl or a cinnamyl), and the ring Am in the formula (2) is a 5 to 7-membered ring having an amide bond in the ring, which may further have an oxygen atom, a sulfur atom, a carbonyl and/or N-R9 ($R^9$ is a hydrogen, an alkyl or an aryl) and may be condensed with a 5 to 7-membered saturated or unsaturated ring;

In the above definitions, the group having an aryl or a heteroaryl may have 1 to 5 substituents on its ring;

provided that when T is represented by the formula (1), t is 2 or 3, $R^5$ is a hydrogen, and Y is any one of the following, at least either $R^1$ or $R^2$ is a group other than a hydrogen, a halogen, a nitro, an alkoxy and an alkyl:

(i) Y is C(R$^6$)(R$^7$) ($R^6$ is a hydroxyl group and $R^7$ is an aryl or an arylalkyl)

(ii) Y is C(R$^6$)(R$^7$) ($R^6$ is a hydrogen and $R^7$ is a diarylalkyl)

(iii) Y is C(R$^6$)(R$^7$) ($R^6$ and $R^7$ form a bisarylmethylene)

(iv) Y is N-R$^8$ ($R^8$ is an alkyl, an aryl, an arylalkyl, a heteroarylalkyl, a diarylalkyl, a cycloalkylalkyl or an aroyl);

or its pharmaceutically acceptable salt.

In the above formula (I), the halogen at $R^x$ or $R^2$ is chlorine, bromine, iodine or fluorine.

The alkyl at $R^1$, $R^2$, $R^3$, $R^5$, $R^6$, $R^7$, $R^8$, $R^9$, $R^{10}$ or $R^{11}$ is a straight or branched-chain alkyl having 1 to 8 carbon atoms, and is exemplified by methyl, ethyl, propyl, isopropyl, butyl, isobutyl, tert-butyl, pentyl, isopentyl, hexyl, heptyl or octyl, with preference given to an alkyl having 1 to 4 carbon atoms.

The mono- or di-substituted amino at $R^1$, $R^2$ or $R^7$ is an amino mono- or di-substituted by alkyl(s) having 1 to 4 carbon atoms, and is exemplified by methylamino, dimethylamino, ethylamino, diethylamino, propylamino, dipropylamino or isopropylamino.

The alkoxy at $R^1$, $R^2$ or $R^5$ is a straight or branched-chain alkoxy having 1 to 8 carbon atoms such as methoxy, ethoxy, propoxy, isopropoxy, butoxy, isobutoxy, tert-butoxy, pentyloxy, hexyloxy, heptyloxy or octyloxy, with preference given to an alkoxy having 1 to 4 carbon atoms.

The hydroxyalkyl at $R^1$ or $R^2$ has 1 to 4 carbon atoms and is exemplified by hydroxymethyl, 1-hydroxyethyl, 1-hydroxypropyl or 1-hydroxybutyl; the haloalkyl at $R^1$ or $R^2$ has 1 to 4 carbon atoms and is exemplified by chloromethyl, bromomethyl, fluoromethyl, dichloromethyl, difluoromethyl, trifluoromethyl, chloroethyl, 2,2,3,3-tetrafluoropropyl or 2,2,2-trifluoroethyl; and the haloalkoxy at $R^t$ or $R^2$ has 1 to 4 carbon atoms and is exemplified by chloromethoxy, bromomethoxy, fluoromethoxy, dichloromethoxy, difluoromethoxy, trifluoromethoxy, chloroethoxy, 2,2,3,3-tetrafluoropropoxy or 2,2,2trifluoroethoxy.

The alkanoyl at $R^1$, $R^2$, $R^7$ or $R^8$ is an alkanoyl having 2 to 5 carbon atoms such as acetyl, propionyl, butyryl or pivaloyl; and the aroyl at $R^1$, $R^2$, $R^7$ or $R^8$ is exemplified by benzoyl or naphthoyl.

The alkanoyl moiety of the arylalkanoyl at $R^1$ or $R^2$ is an alkanoyl having 2 to 5 carbon atoms, and the arylalkanoyl is exemplified by phenylacetyl, phenylpropionyl or phenylbutyryl; the alkanoyl moiety of the alkanoyloxyalkyl at $R^1$ or $R^2$ is an alkanoyl having 1 to 5 carbon atoms and the alkyl moiety thereof is an alkyl having 1 to 4 carbon atoms, and the alkanoyloxyalkyl is exemplified by 1-formyloxypropyl, acetoxymethyl, propionyloxymethyl, 1- or 2-acetoxyethyl, 1- or 2-Propionyloxyethyl, 1- or 3-acetoxypropyl or 1- or 3-propionyloxypropyl; the alkyl moiety of the aroyloxyalkyl at $R^1$ or $R^2$ is an alkyl having 1 to 4 carbon atoms, and the aroyloxyalkyl is exemplified by benzoyloxymethyl, benzoyloxyethyl, benzoyloxypropyl or benzoyloxybutyl; the alkanoyl moiety of the alkanoylamino at $R^1$ or $R^2$ is an alkanoyl having 2 to 5 carbon atoms, and the alkanoylamino is exemplified by acetylamino, propionylamino or butyrylamino; and the alkanoyl moiety of the arylalkanoylamino at $R^1$ or $R^2$ is an alkanoyl having 2 to 5 carbon atoms, and the arylalkanoylamino is exemplified by phenylacetylamino, phenylpropionylamino or phenylbutyrylamino.

The aroylamino at $R^1$, $R^2$ or $R^7$ is exemplified by benzoylamino or naphthoylamino.

The alkyl moiety of the formylaminoalkyl at $R^1$ or $R^2$ is an alkyl having 1 to 4 carbon atoms, and the formylaminoalkyl is exemplified by formylaminomethyl or formylaminoethyl; the alkanoyl moiety of the alkanoylaminoalkyl at $R^1$ or $R^2$ is an alkanoyl having 2 to 5 carbon atoms and the alkyl moiety thereof is an alkyl having 1 to 4 carbon atoms, and the alkanoylaminoalkyl is exemplified by acetylaminomethyl, acetylaminoethyl or propionylaminomethyl; the alkanoyl moiety of the haloalkanoylaminoalkyl at $R^1$ or $R^2$ is an alkanoyl having 2 to 5 carbon atoms and the alkyl moiety thereof is an alkyl having 1 to 4 carbon atoms, and the haloalkanoylaminoalkyl is exemplified by trifluoroacetylaminomethyl or trifluoroacetylaminoethyl; the alkanoyl moiety of the arylalkanoylaminoalkyl at $R^1$ or $R^2$ is an alkanoyl having 2 to 5 carbon atoms and the alkyl moiety thereof is an alkyl having 1 to 4 carbon atoms, and the arylalkanoylaminoalkyl is exemplified by phenylacctylaminomethyl; and the alkyl moiety of the aroylaminoalkyl at $R^1$ or $R^2$ is an alkyl having 1 to 4 carbon atoms, and the aroylaminoalkyl is exemplified by benzoylaminomethyl.

The alkyl moiety of the arylalkyl at $R^1$, $R^2$, $R^7$ or $R^8$ is an alkyl having 1 to 6 carbon atoms, and the arylalkyl is exemplified by benzyl, phenylethyl, phenylpropyl or diphenylmethyl.

The mono- or di-substituted carbamoyl at $R^1$, $R^2$, $R^6$ or $R^8$ is a carbamoyl mono- or di-substituted by an alkyl having 1 to 4 carbon atoms, cyclohexyl, phenyl or benzyl, such as methylcarbamoyl, ethylcarbamoyl, propylcarbamoyl, dimethylcarbamoyl, diethylcarbamoyl, dipropylcarbamoyl, cyclohexylcarbamoyl, phenylcarbamoyl or benzylcarbamoyl.

The alkyl moiety of the carbamoylalkyl at $R^1$ or $R^2$ is an alkyl having 1 to 4 carbon atoms, and the carbamoylalkyl is exemplified by carbamoylmethyl or 2-carbamoylethyl; the mono- or di-substituted carbamoyl of the mono- or di-substituted carbamoylalkyl at $R^1$ or $R^2$ is a carbamoyl mono- or di-substituted by an alkyl having 1 to 4 carbon atoms or benzyl, and the alkyl moiety thereof is an alkyl having 1 to 4 carbon atoms, and the mono- or di-substituted carbamoylalkyl is exemplified by methylcarbamoylmethyl; the alkyl moiety of the aminoalkyl at $R^1$ or $R^2$ is an alkyl having 1 to 4 carbon atoms, and the aminoalkyl is exemplified by aminomethyl, aminoethyl or aminopropyl; the mono- or di-substituted amino of the mono- or di-substituted aminoalkyl at $R^1$ or $R^2$ is an amino mono- or di-substituted by alkyl(s) having 1 to 4 carbon atoms, and the alkyl moiety thereof is an alkyl having 1 to 4 carbon atoms, and the mono- or di-substituted aminoalkyl is exemplified by methylaminomethyl, dimethylaminomethyl, methylaminoothyl, dimethylaminoethyl, ethylaminomethyl, diethylaminomethyl, propylaminomethyl, methylaminopropyl or dimethylaminopropyl; the alkyl moieties of the alkylsulfonylaminoalkyl st $R^1$ or $R^2$ are respectively an alkyl having 1 to 4 carbon atoms, and the alkylsulfonylaminoalkyl is exemplified by methanesulfonylaminemethyl or methanesulfonylaminoethyl; the alkyl moiety of the hydroxyiminoalkyl st $R^1$ or $R^2$ is an alkyl having 1 to 4 carbon atoms, and the hydroxyiminoalkyl is exemplified by 1-hydroxyiminoethyl, 1-hydroxyiminopropyl or 1-hydroxyiminobutyl; the alkoxy moiety and the alkyl moiety of the alkoxyiminoalkyl at $R^1$ or $R^2$ are respectively alkoxy and alkyl each having 1 to 4 carbon atoms, and the alkoxyiminoalkyl is exemplified by 1-methoxyiminoethyl, 1-ethoxyiminoethyl, 1-methoxyiminopropyl or 1-isopropoxyiminoethyl.

The ester residue at $R^3$ which is hydrolyzable in the body is the one easily decomposed in the body into a free carboxylic acid or its salt, and is exemplified by an alkanoyloxyalkyl ester such as acetoxymethyl, pivaloyloxymethyl, 1-acetoxyethyl or 1-pivaloyloxyethyl; an alkoxycarbonyloxyalkyl ester such as ethoxycarbonyloxymethyl or 1-ethoxycarbonyloxyethyl; ester such as phthalidyl or dimethoxyphthalidyl; carbamoylalkyl ester such as carbamoylmethyl, carbamoylethyl, N-methylcarbamoylmethyl, N,N-dimethylcarbamoylmethyl or N,N-diethylcarbamoylmethyl; alkoxyalkyl ester such as methoxymethyl or methoxyethyl; or 5-methyl-1,3-dioxolen-2-on-4-ylmethyl ester.

The alkylene at A is a straight or branched-chain alkylene having 1 to 10 carbon atoms, such as methylene, ethylene, trimethylene, tetramethylene, pentamethylene, hexamethylene, octamethylene, decamethylene, propylene, 1,1-dimethylethylene or 2,2-dimethyltrimethylene, with preference given to an alkylene having 1 to 6 carbon atoms.

The alkyl moiety of the heteroarylalkyl at $R^4$ which may be hydrogenated is an alkyl having 1 to 4 carbon atoms, and the heteroarylalkyl is exemplified by pyridylmethyl, furylmethyl, thienylmethyl or (1,4-benzodioxan-2-yl)methyl.

The aryl at $R^7$, $R^8$ or $R^9$ is phcnyl, naphthyl, or the like.

The alkyl moiety of the cyanoalkyl at $R^7$ or $R^8$ is an alkyl having 1 to 4 carbon atoms, and the cyanoalkyl is exemplified by cyanomethyl, 2-cyanoethyl, 3-cyanopropyl or 4-cyanobutyl; the alkyl moiety of the hydroxyalkyl at $R^7$ or $R^8$ is an alkyl having 1 to 4 carbon atoms, and the hydroxyalkyl is exemplified by hydroxymethyl, 2-hydroxyethyl, 3-hydroxypropyl or 4-hydroxybutyl; the alkoxy moiety of the alkoxycarbonyl at $R^7$ or $R^8$ is an alkoxy having 1 to 4 carbon atoms, and the alkoxycarbonyl is exemplified by methoxycarbonyl, ethoxycarbonyl, propoxycarbonyl, isopropoxycarbonyl, butoxycarbonyl, isobutoxycarbonyl or tertbutoxycarbonyl; the alkyl moiety of the diarylalkyl at $R^7$ or $R^8$ is an alkyl having 1 to 4 carbon atoms, and the diarylalkyl is exemplified by diphenylmethyl or 2,2-diphenylethyl; examples of the heteroaryl at $R^7$ or $R^8$ include pyridyl, thienyl, furyl, pyrimidinyl, thiazolyl, oxazolyl, indolyl, benzothiazolyl, benzimidazolyl, 1,2-benzisothiazolyl, 1,2-benzisoxazolyl, benzothiophen-2- or 3-yl, benzofuran-2 or 3-yl, quinolyl, isoquinolyl, benzoxazolyl, pyrazinyl, pyridazinyl, imidazolyl, thieno[3,2-c]pyridin-4-yl, furo[3,2-c]pyridin-4-yl, 7,8-dihydro-5H-thiopyrano [4,3-b]pyridin-2-yl, 1,2-benzisothiazolyl-S,S-dioxide, 2-oxo-1-benzimidazolyl, 2-thioxo-1-benzimidazolyl, 2,4-dioxohexahydropyrimidin-1-yl and hydantoin-1-yl; the heretoarylalkyl at $R^7$ or $R^8$ may be hydrogenated, and the alkyl moiety thereof is an alkyl having 1 to 4 carbon atoms, and the heteroarylalkyl is exemplified by pyridylmethyl, furylmethyl, thienylmethyl, pyrrolylmethyl, oxazolylmethyl, thiazolylmethyl or (1,2-benzodioxan-2-yl)methyl; the heteroarylcarbonyl at $R^7$ or $R^8$ may be nicotinoyl, isonicotinoyl, thenoyl, furoyl, pyrrolylcarbonyl, oxazolylcarbonyl or thiazolylcarbonyl; the cycloalkyl at $R^7$ or $R^8$ is a cycloalkyl having 3 to 8 carbon atoms such as cyclopropyl, cyclobutyl, cyclopentyl, cyclohexyl or cycloheptyl; and the cycloalkyl moiety of the cycloalkylalkyl at $R^7$ or $R^8$ is a cycloalkyl having 3 to 8 carbon atoms and the alkyl moiety thereof is an alkyl having 1 to 4 carbon atoms, and the cycloalkylalkyl is exemplified by cyclopropylmethyl, cyclobutylmethyl, cyclohexylmethyl or cycloheptylmethyl.

The cyclic amino at $R^7$ includes, for example, pyrrolidinyl, piperidino, hexamethylcneimino, morpholino, thiomorpholino, piperazinyl, homopiperazinyl, 4-substituted piperazinyl and 4-substituted homopiperazinyl (substitucnt is exemplified by alkyl having 1 to 4 carbon atoms, aryl, benzyl, alkanoyl having 2 to 5 carbon atoms or benzoyl).

The bisarylmethylene formed by $R^6$ and $R^7$ is, for example, diphenylmethylene, bis(4-fluorophenyl)methylene or bis(4-chlorophenyl)methylenc.

The acyl at $R^{10}$ or $R^{11}$ is, for example, alkanoyl having 2 to 5 carbon atoms such as acetyl, propionyl or butyryl, or benzoyl.

The 5- to 7-membered ring Am having an amide bond in the formula (2) is, for example, thiazolidinonc, imidazolidinone, pyrazolidinone or pyrrolidinone, and the ring Am may further have oxygen atom, sulfur atom, carbonyl and/or N-R$^9$ (R$^9$ is hydrogen, alkyl or aryl) in the ring. The ring Am may be condensed with a 5- to 7-membered saturated or unsaturated ring, which is exemplified by 2-oxo-1,2,3,5,6, 7,8,8a-octahydroimidazo[1,2-a]pyridine-3-spiro-4'-piperidino or 2-oxo-2,3,5,6,7,8-hexahydroimidazo[1,2-a]pyridine-3-spiro-4'piperidino.

In the above definitions, the group including cycloalkyl, aryl, benzyl, benzoyl or heteroaryl may have 1 to 5, preferably 1 to 3 substituents, which substituents being exemplified by halogen, nitro, amino, cyano, haloalkyl having 1 to 4 carbon atoms, hydroxyl group, alkyl having 1 to 4 carbon atoms, alkoxy having 1 to 4 carbon atoms, alkenyl having 2 to 4 carbon atoms, and phenyl.

In the above formula (I), R$^1$ is preferably acetyl, acetylamino, acetylaminomethyl, 2-acetylaminoethyl, methyl, aminomethyl, benzoylamino, propionylaminomethyl, or the like, and R$^2$ is particularly preferably hydrogen, halogen, methyl, or the like. Preferable X includes, for example, -S-, -SO-, -SO$_2$-, -CO-, -CH$_2$- and -CH(OH)-, and A is preferably methylene, ethylene, trimethylene, tetramethylene, pentamethylene, hexamethylene, 2-methyltrimethylene, or the like. T is preferably 1-piperazinyl substituted at the 4-position by, for example, 2-pyrimidinyl, 3-trifluorophenyl, 2-methoxyphenyl, 2,3-dimethylphenyl, 1,2-benzisothiazol-3-yl, methyl, 3-chlorophenyl, bis(4-chloropheny])methyl, 3-trifluoromethyl, 6pyridyl, 1,2-benzisoxazol-3-yl, cyclohexylcarbamoyl or phenylcarbamoyl; pyperidino substituted at the 4-position by, for example, 4-fluorobenzoyl, 6-fluoro-1,2-benzisoxazol-3-yl or 1,2-benzisothiazol-3-yl; or the like, and particularly preferred are, for example, 4-(1,2-benzisothiazol-3-yl)-1-piperadinyl and 4-(6-fluoro-1,2-benzisoxazol-3-yl)piperidino.

Examples of the pharmaceutically acceptable salt of the compound of the formula (I) include salts with inorganic acids such as hydrochloric acid, hydrobromic acid, sulfuric acid, phosphoric acid and nitric acid, and salts with organic acids such as acetic acid, succinic acid, glycolic acid, lactic acid, malic acid, tartaric acid, citric acid, ascorbic acid, maleic acid, fumaric acid, methancsulfonic acid and benzenesulfonic acid. In the case where the compound has carboxyl group, the salt may be a metal salt such as sodium, potassium or calcium salt, an amine salt with methylamine, diethylamine, triethylamine, or the like, or a salt with an amino acid such as lysine, ornithine or arginine. In addition, hydrates (e.g. ½ hydrate, monohydrate, 3/2 hydrate) and other solyates are also encompassed.

Where the compound of the present invention has an asymmetric carbon, racemates and optical isomers are encompassed, and where the compound has an oxime, syn- and anti-isomers are encompassed in the present invention.

The thiophene compound of the invention can be produced by the following methods.

Method 1

The compound of the formula (I) can be produced by reacting a compound of the formula

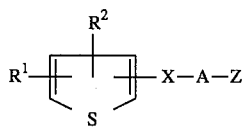
(II)

wherein Z is a hydroxyl group or a reactive atom or group derived from hydroxyl group, such as halogen, methanesulfonyloxy or P-toluensulfonyloxy, and other symbols are as defined above, with a compound of the formula

H-T (III)

wherein each symbol is as defined above.

When Z in the compound of the formula (II) is a reactive atom or group derived from hydroxyl group, the reaction with the compound of the formula (III) may be carried out in a suitable solvent which does not interfere with the reaction, such as methanol, ethanol, propanol, benzene, toluene, dimethylformamide, tetrahydrofuran, acetonitrile or acetone, in the presence of a suitable acid scavenger such as potassium carbonate, sodium carbonate, sodium hydrogencarbonate, potassium hydroxide, pyridine, triethylamine, sodium acetate or potassium acetate at a temperature between 20° C. and 150° C. for 30 minutes to 30 hours.

When Z in the compound of the formula (II) is a hydroxyl group, the reaction may be carried out in a suitable solvent which does not adversely affect the reaction, such as dimethyl-formamide or benzene in the presence of an aminophosphonium reagent such as N,N-methylphenylaminotriphenylphosphonium or iodide at a temperature between 20° C. and 150° C. for 30 minutes to 5 hours.

Method 2

Of the compounds of the formula (I), a compound wherein X is -S(O)$_n$- (n is 1 or 2) can be produced by subjecting a compound wherein n is 0 to an oxidation.

The oxidation can be usually carried out in a suitable solvent with the use of an oxidizing agent such as m-chloroperbenzoic acid, peracetic acid, sodium bromite or hydrogen peroxide. As the reaction solvent, usable are, for example, chloroform, tetrahydrofuran, dioxane, and water, and the reaction temperature is between 0° C. and a temperature near the boiling point of the solvent used, preferably between 0° C. and 30° C.

Method 3

Of the compounds of the formula (I), a compound wherein R$^1$ or R$^2$ is R$^{12}$-CONH- (R$^{12}$ is hydrogen, alkyl, aralkyl or aryl), or R$^{12}$-NHCO- (R$^{12}$ is as defined above) can be produced by converting a compound of the formula

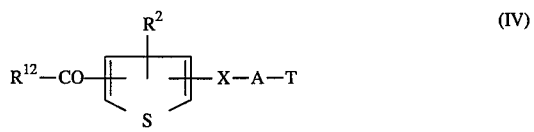
(IV)

wherein each symbol is as defined above, to an oxime compound, and subjecting the oxime compound to Beckmann rearrangement.

The conversion to an oxime compound is conducted by using hydroxylamine hydrochloride in a solvent such as water or ethanol in the presence of a base such as sodium hydroxide, potassium hydroxide, sodium hydrogencarbonate or potassium hydrogencarbonate at a temperature between 0° C. and a temperature near the boiling point of the solvent used, preferably between 80° C. and 100° C. The oxime compound thus obtained is heated to 70° C. to 120° C. in polyphosphoric acid or sulfuric acid to conduct Beckmann rearrangement.

Method 4

Of the compounds of the formula (I), a compound wherein $R^1$ or $R^2$ is aminoalkyl can be produced by reducing the oxime compound obtained in Method 3.

The reduction can be carried out by using a chemical reducing agent such as lithium aluminium hydride or sodium borohydride, in a solvent such as tetrahydrofuran or an ether at a temperature between 50° C. and 100° C.

Method 5

The compound of the formula (IV) can be produced by reacting a compound of the formula

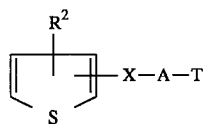
(V)

wherein each symbol is as defined above, with a carboxylic acid of the formula

$R^{12}COOH$ (VI)

wherein $R^{12}$ is as defined above, or its reactive derivative such as acid halide, acid anhydride, mixed acid anhydride, active ester, or the like.

When the compound of the formula (VI) is a free carboxylic acid, the reaction is carried out in the presence of a dehydrating agent such as polyphosphoric acid at room temperature to 150° C.

When an acid halide such as chloride, bromide, iodide, etc. is used as the reactive derivative of the formula (VI), the reaction is carried out in a suitable solvent which does not adversely affect the reaction, such as benzene, toluene, chloroform, methylene chloride or dichloroethane, in the presence of a Lewis acid such as aluminium chloride, tin chloride or iron chloride at −10° C. to 100° C. for 5 minutes to 20 hours.

Method 6

A compound of the formula

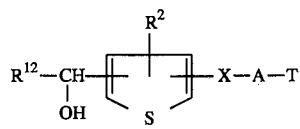
(VII)

wherein each symbol is as defined above, can be obtained by chemical reduction of the compound of the formula (IV) using, for example, sodium borohydride, lithium aluminium hydride or triethylsilane in a suitable solvent which does not adversely affect the reaction, such as methanol, ethanol, propanol, butanol or acetic acid by chemical reduction, or by catalytic reduction in the presence of a suitable catalyst such as palladium, rhodium or platinum at −10° C. to 150° C. for 5 minutes to 20 hours.

Method 7

A compound of the formula

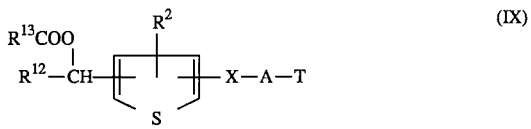
(IX)

wherein each symbol is as defined above, can be obtained by reacting the compound of the formula (VII) with a carboxylic acid of the formula

$R^{13}COOH$ (VIII)

wherein $R^{13}$ is hydrogen, alkyl, aryl, aralkyl or heteroaryl, or its acid anhydride.

The reaction proceeds in a suitable solvent which does not adversely affect the reaction, such as benzene or toluene, or without solvent at room temperature to 150° C. The instant reaction also proceeds in the presence of a base such as triethylamine.

Method 8

Of the compounds of the formula (I), a compound wherein X is -CH(OH)- or -CH$_2$- can be obtained by reducing a compound wherein X is -CO- with the use of a suitable reducing agent such as sodium borohydride.

The reaction proceeds in a suitable solvent which does not adversely affect the reaction, such as methanol, ethanol, propanol, isopropyl alcohol, tetrahydrofuran, dichloromethane or dichloroethane in the presence of a suitable reducing agent such as lithium aluminium hydride, sodium borohydride, sodium cyanoborohydride, trifluoroborodiethylate or triethylsilane at −10° C. to 100° C. for 30 minutes to 10 hours.

Method 9

Of the compounds of the formula (I), a compound wherein $R^1$ or $R^2$ is $R^{14}$-CONH-B- ($R^{14}$ is hydrogen, alkyl, haloalkyl, aralkyl or aryl, and B is a single bond or alkylene) can be obtained by reacting a compound of the formula

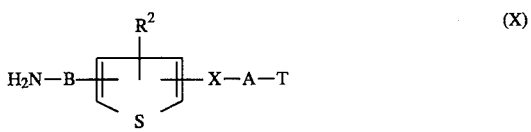
(X)

wherein each symbol is as defined above, with a carboxylic acid of the formula

$R^{14}COOH$ (XI)

wherein $R^{14}$ is as defined above, or its reactive derivative such as acid halide or acid anhydride.

The reaction proceeds in a suitable solvent which does not adversely affect the reaction such as dichloromethane, dichloroethane or chloroform in the presence of a suitable acid scavenger such as triethylamine, methylmorpholine or pyridine at 0° C. to 100° C.

Method 10

Of the compounds of the formula (I), a compound wherein $R^1$ or $R^2$ is $R^{15}$-SOaNH-B- ($R^{15}$ is alkyl or aryl, and B is a single bond or alkylene) can be obtained by reacting a compound of the formula (X) and a sulfonic acid of the formula $$R^{15}\text{-}SO_3H \tag{XII}$$

wherein $R^{15}$ is as defined above, or its reactive derivative (acid halide).

The reaction proceeds in a suitable solvent which does not adversely affect the reaction such as dichloromethane, dichloroethane or chloroform in the presence of a suitable acid scavenger such as triethylamine, methylmorpholine or pyridine at 0° C. to 100° C.

Method 11

Of the compounds of the formula (I), a compound wherein $R^1$ or $R^2$ is aminoalkyl can be obtained by hydrolyzing a compound of the formula

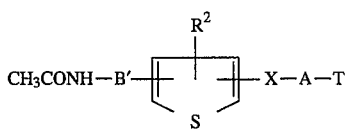
(XIII)

wherein B' is alkylene, and other symbols are as defined above.

Method 12

Of the compounds of the formula (I), a compound wherein X is -CH(OR$^{10\cdot}$)-($R^{10\cdot}$ is alkyl or acyl) can be produced by reacting a compound of the formula (I) wherein X is -CH(OH)- and a compound of the formula $$R^{10\cdot}\text{-}Z^1 \tag{XIV}$$

wherein $Z^1$ is halogen, and $R^{10\cdot}$ is as defined above.

The reaction proceeds in a suitable solvent which does not adversely affect the reaction, such as methanol, ethanol, propanol, butanol, N,N-dimethylformamide, tetrahydrofuran, benzene or toluene in the presence of a suitable acid scavenger such as sodium hydride, sodium amide, sodium methoxide, sodium ethoxide, potassium hydroxide or sodium hydroxide at room temperature to 150° C. for an hour to 20 hours.

Method 13

Of the compounds of the formula (I), a compound wherein X is -C(=NOH)- can be produced by reacting a compound of the formula (I) wherein X is -CO- with hydroxylamine.

The reaction is carried out by allowing hydroxylamine or its salt such as hydrochloride, hydrobromide or sulfate to react in a suitable solvent which is subject to no limitation so long as it does not adversely affect the reaction, and is preferably exemplified by alcohols such as methanol, ethanol, propanol, isopropyl alcohol or butanol, in the presence or absence of an acid scavenger such as an organic base (e.g. triethylamine, pyridine, N,N-dimethylaniline) or inorganic base (e.g. sodium carbonate, potassium carbonate, sodium hydrogencarbonate). The reaction temperature and reaction time are not particularly limited, and the reaction is normally conducted at room temperature to a temperature near the boiling point of the solvent used for several to several dozens of hours.

Method 14

Of the compounds of the formula (I), a compound wherein X is -C(=NOR$^{11\cdot}$)-($R^{11\cdot}$ is alkyl or acyl) can be produced by reacting a compound of the formula (I) wherein X is -C(=NOH)- with a compound of the formula $$R^{11\cdot}\text{-}Z^1 \tag{XV}$$

wherein $Z^1$ is halogen, and $R^{11\cdot}$ is as defined above, in the same manner as in Method 12.

Method 15

Of the compounds of the formula (I), a compound wherein X is -CH(NH$_2$)- can be produced by subjecting a compound of the formula (I) wilerein X is -C(=NOH)- to a reduction using a suitable reducing agent.

The reduction is carried out using a suitable catalyst such as palladium carbon, Raney-nickel, platinum or rhodium in a suitable solvent which is subject to no limitation so long as it does not adversely affect the reaction, such as alcohols (e.g. methanol, ethanol, propanol or isopropyl alcohol), or acids (e.g. formic acid, acetic acid) by a catalytic hydrogenation under atmospheric pressure or pressurization.

The reaction temperature and reaction time are not particularly limited, and the reaction is usually conducted at room temperature to about 150° C. for several to several dozens of hours, or using a suitable reducing agent such as lithium aluminium hydride or tri*tert-butoxyaluminium hydride in a suitable solvent which is subject to no limitation as long as it does not adversely affect the reaction, but preferably ethers such as diethylether, tetrahydrofuran, dioxane and dimethylcellusolve, under cooling, at room temperature, or under heating for several to several dozens of hours.

Of the starting materials represented by the formula (II) in Nethod 1, the compound wherein X is -S(O)n- (n=0) can be produced by the following reaction.

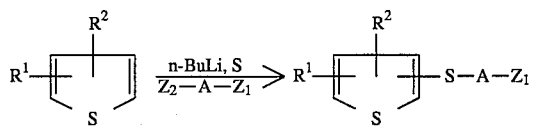

This reaction is carried out by lithiation by a conventional method using butyl lithium in a nonaqueous solvent such as ether, tetrahydrofuran, dioxane, benzene, toluene or a mixed solvent thereof, followed by reaction with sulfur, and then with a compound of $Z_2$-A-$Z_1$ (wherein $Z_1$ and $Z_2$ are each a hydroxyl group or a reactive atom or a group derived from hydroxyl group such as halogen, methancsulfonyloxy or p-toluenesulfonyloxy; $Z_1$ and $Z_2$ are not hydroxyl groups at the same time; and A is as defined above).

The reaction proceeds in a suitable solvent which does not adversely affect the reaction, such as methanol, ethanol, propanol, N,N-dimethylformamide, benzene, toluene, tetrahydrofuran or acetonitrile in the presence of a suitable base such as sodium methoxide, sodium ethoxide, potassium t-butoxide, sodium hydride, potassium hydride, sodium hydroxide, potassium hydroxide, potassium carbonate or sodium carbonate at –20° C. to 150° C. for 30 minutes to 5 hours.

Of the starting compounds represented by the formula (II), the compound wherein X is -S(O)$_n$- (n=0) can be also produced by reacting 2-mercaptothiophene derivative with, for example, dialkylene dihalide in the presence of a base such as sodium hydroxide, potassium hydroxide, sodium hydride or sodium metal. The reaction solvent is exemplified by dimethylformamide, toluene, methanol or ethanol, and the reaction temperature is from 0° C. to a temperature near the boiling point of the solvent used, preferably from 0° C. to 80° C.

Of the starting compounds represented by the formula (II), the compound wherein X is $-S(O)_n-$ (n=1,2) can be produced by oxidating the compound wherein n=0.

Examples of the oxidizing agent to be used for this oxidation include m-chloroperbenzoic acid, peracetic acid, sodium bromite, and hydrogen peroxide, and examples of the solvent to be used for this reaction include chloroform, dichloromethane, tetrahydrofuran, dioxane, dimethylformamide, and water. The reaction temperature is from −70° C. to a temperature near the boiling point of the solvent used, preferably from −20° C. to 0° C.

Of the starting compounds represented by the formula (II) in Method 1, the compound wherein X is -CO- can be produced by reacting a compound of the formula

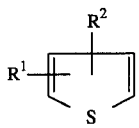

(XVI)

wherein each symbol is as defined above, with a carboxylic acid halide of the formula

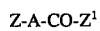

$Z-A-CO-Z^1$  (XVII)

wherein each symbol is as defined above. The reaction proceeds in a suitable solvent which does not adversely affect the reaction, such as benzene, toluene, chloroform, methylene chloride or dichloroethane, in the presence of a Lewis acid such as aluminium chloride, tin chloride or iron chloride at −10° C. to 100° C. for 5 minutes to 20 hours.

Of the starting compounds represented by the formula (II) in Method 1, the compound wherein X is -CH(OH)- or -CH$_2$- can be produced by reducing a compound wherein X is -CO- using a suitable reducing agent such as sodium borohydride.

The reaction proceeds in a suitable solvent which does not adversely affect the reaction, such as methanol, ethanol, propanol, isopropyl alcohol, tetrahydrofuran, dichloromethane or dichloroethane, in the presence of a suitable reducing agent such as lithium aluminium hydride, sodium borohydride, sodium cyanoborohydride, trifluoroborodiethylate or triethylsilane at −10° C. to 100° C. for 30 minutes to 10 hours.

The thiophene compound of the formula (I) thus produced can be converted to an acid addition salt with the above-mentioned inorganic acid or organic acid, if necessary. The compound having carboxylic group can be converted to a metal salt such as sodium, potassium or calcium salt; an amine salt with triethylamine, or the like; or a salt with an amino acid such as lysine or ornithine. Also, the compound can be obtained as a solvate such as hydrate.

When the compound of the present invention obtained in the aforementioned manner has an asymmetric center, it is normally produced as a racemate, which can be optically resolved into optical isomers by conventional methods such as fractional recrystallization, chromatography, etc. In addition, an optical isomer can be produced from an optically active starting material, and syn- or anti-isomer can be resolved by conventional methods.

Experiment Example 1: Affinity for dopamine 2 receptor

A specific binding of dopamine 2 ($D_2$) receptor was tested according to the method described in Eur. J. Pharmacol. 46, 377 (1977).

A synaptosome fraction was separated from corpus striatum of 9–10 weeks old Wistar rat, and suspended in 50 mM Tris-HCl buffer (pH 7.1) containing 120 mM sodium chloride, 5 mM potassium chloride, 2 mM calcium chloride, 1 mM magnesium chloride, 10 μM pargyline and 0.1% ascorbic acid for use in the test.

The test compound at several concentrations and tritiated spiperone (final concentration 0.2 nM) were added to the synaptosome suspension, and each mixture was reacted at 37° C. for 20 minutes. After the reaction, the reaction mixture was filtered with suction through a Whatman GF/B glass filter. The filter was washed with 50 mM Tris-HCl buffer (pH 7.7), and the radioactivity of the filter was measured by a liquid scintillation counter. Non-specific binding was determined in the presence of $10^{-4}$M(±)-sulpiride. The concentration necessary for 50% inhibition (IC$_{50}$) was determined on a graph, and inhibition constant (Ki value) was calculated. The results are shown in Table 1.

Experiment Example 2: Affinity for serotonin 1A receptor

A specific binding of serotonin 1A (5-HT$_{1A}$) receptor was tested according to the method described in J. Neurochem. 44, 1685 (1985).

A crude synaptosome fraction was separated from hippocampus of 9–10 weeks old Nistar rat, and suspended in 50 mM Tris-HCl buffer (pH 7.4) containing 1 mM manganese chloride for use in the test. The test compound at several concentrations and tritiated 8-hydroxy-2-dipropylaminotetralin (8-OH-DPAT, final concentration 0.2 nM) were added to the synaptosome suspension, and each mixture was reacted at 37° C. for 12 minutes. After the reaction, the reaction mixture was filtered with suction through a Whatman GF/B glass filter. The filter was washed with 50 mM Tris-HCl buffer (pH 7.7), and the radioactivity of the filter was measured by a liquid scintillation counter. Non-specific binding was determined in the presence of $10^{-5}$ M serotonin (5HT). The concentration necessary for 50% inhibition (IC$_{50}$) was determined on a graph, and inhibition constant (Ki value) was calculated. The results are shown in Table 1.

Experiment Example 3: Affinity for serotonin 2 receptor

A specific binding of serotonin 2 (5-HT2) receptor was tested according to the method described in Mol. Pharmacol. 21, 301 (1981).

A crude synaptosome fraction was separated from hippocampus of 9–10 weeks old Wistar rat, and suspended in 50 mM Tris-HCl buffer (pH 7.7) for use in the test. The test compound at several concentrations and tritiated ketanserin (final concentration 0.2 nM) were added to the synaptosome suspension, and each mixture was incubated at 37° C. for 20 minutes. After the incubation, the mixture was filtered with suction through a Whatman GF/B glass filter. The filter was washed with 50 mM Tris-HCl buffer (plt 7.7), and the radioactivity of the filter was measured by a liquid scintillation counter. Non-specific binding was determined in the presence of $10^{-5}$ M mianserin. The concentration necessary for 50% inhibition (IC$_{50}$) was determined on a graph, and inhibition constant (Ki value) was calculated. The results are shown in Table 1.

Experiment Example 4: Anti-apomorphine action (mouse) Male dd mice were used for the test (3 per group). The test compound was orally administered to the mice, and 60 minutes later, 0.5 mg/kg of apomorphine hydrochloride was subcutaneously administered. The movement for 20 minutes from immediately after the administration was measured using Balimex (Columbus, USA). Each group was tested three times, and the amount of the test compound necessary to lower the movement by than that of a comparison group was calculated from a graph and taken as EDso. The results are shown in Table 1.

TABLE 1

| test compound | binding (nM) | | | anti-apomorphine effect $ED_{50}$ |
|---|---|---|---|---|
| (Ex. No.) | $D_2$ | $5\text{-}HT_{1A}$ | $5\text{-}HT_2$ | (mg/kg p.o.) |
| 21 | 1.3 | 0.12 | 0.59 | 35 |
| 36 | 0.61 | 0.75 | 1.3 | 3.4 |
| 40 | 0.71 | 0.35 | 0.45 | 1.0 |
| 93 | 0.8 | 26 | 0.79 | 2.9 |
| 95 | 2.5 | 140 | 0.059 | 2.6 |
| 108 | 2.0 | 56 | 2.1 | 0.41 |
| 119 | 3.8 | 14 | 0.65 | 0.16 |
| 151 | 3.8 | 15 | 0. 099 | 0.76 |
| 155 | 1.4 | >100 | 0.37 | 1.2 |
| 158 | 0.94 | 16 | 0.13 | 0.14 |
| 159 | 0.5 | 12 | 0.047 | 0.53 |
| 165 | 0.69 | 1.7 | 1.3 | 0.24 |

Experiment Example 5: Acute toxicity Male ddY mice were used at 5 per group, and intraperitoneally administered with 100 mg/kg of the compound of Example 4. No death was observed for 5 days after the administration. In a similar manner, 300 mg/kg of the compound was orally administered, and no death was observed for 5 days after the administration.

The compound of the present invention possesses pharmacological actions required of an antipsychotic such as motility suppressing action, anti-apomorphinc action, methamphetamine antagonistic action, tetrabenazine-induced blepharoptosis enhancing action, and the like, and additionally possesses strong inhibitory action on serotonin-induced head-twitch. In the determination of affinity for receptors using tritiumlabeled ligands, the compound of the invention showed high affinity for dopamine ($D_2$) receptor and serotonin (5-HT2) receptor. Furthermore, catalepsy inducing action, which is an index of extrapyramidal side-effects, was examined using rats, and the compound of the invention showed extremely weak action, from which result the compound of the invention has been proved to be useful as an antipsychotic causing less extrapyramidal side-effects. Also, the compound of the invention has been found to show high affinity for serotonin (5-$HT_2$) receptor, and has an antianxiety action, and the compound is also useful as a non-benzodiazepine type antianxiety agent.

When the compound of the invention is used as a pharmaceutical, it is usually admixed with vehicles, diluents, solubilizers, and so on, and safely administered to patients in the form of tablet, powder, granule, capsule, injection, transfusion, etc. While the dose varies depending on symptom, body weight, age, etc. of patients, it is normally administered to an adult in the range of from 1 to 500 mg per day in a single or several times divided doses.

The present invention is hereinbelow described in detail by way of reference examples and examples. It should be understood that the present invention is not limited to these examples.

Reference Example 1

To a solution of 2-(1-ethylenedioxyethyl)thiophene (30 g) in tetrahydrofuran (250 ml) was dropwise added n-butyl lithium (110ml) at −50° C., after which sulfur (5.6 g) was added thereto, and the mixture was stirred for 2 hours. 1-Bromo-3chloropropane (28 g) was added at −50° C., and the mixture was stirred at room temperature for 2 hours. The reaction mixture was poured into water, extracted with ethyl acetate, and dried over magnesium sulfatc, whereafter the solvent was distilled off under reduced pressure. The residue was dissolved in 300 ml of tetrahydrofuran, diluted hydrochloric acid (100 ml) was added thereto, and the mixture was stirred at room temperature for 15 hours. The reaction mixture was poured into water, extracted with ethyl acetate, and dried over magnesium sulfate. Then, the solvent was distilled off under reduced pressure. The residue was purified by silica gel column chromatography to give 15 g of 2-acetyl-5-(3-chloropropylthio)thiophene.

Reference Example 2

In a similar manner as in Reference Example 1 except the use of 2-(ethylencdioxymethyl)thiophene in place of 2-(1ethylenedioxyethyl)thiophene, 2-formyl-5-(3-chloropropylthio)thiophene was obtained. A solution of hydroxylamine hydrochloride (11 g) in ethanol (100 ml) was neutralized with aqueous sodium hydroxide, and thereto was added 2-formyl-5-(3chloropropylthio)thiophenc (10 g). The mixture was stirred at 45° C. for 30 minutes, and concentrated. The residue was added with water, extracted with ethyl acetate, and washed with water, and then the solvent was distilled off. The residue (11 g) was dissolved in 36 ml of acetic acid and 12 ml of acetic anhydride, and 11 g of zinc dust was added thereto at 40° C. Then, the mixture was stirred for 30 minutes. The reaction mixture was filtered, and the filtrate was concentrated to give 6.4 g of 2-acetylaminomethyl-5-(3-chloropropylthio)thiophene.

Example 1

A mixture of 2-acetyl-5-(4-chlorobutylthio)thiophene (5 g), 2-pyrimidinylpiperazine hydrochloride (5 g), potassium carbonate (8.3 g), potassium iodide (3.3 g), dimethylformamide (50 ml), and toluene (50 ml) was stirred at 90° C. for 4 hours. The reaction mixture was cooled with water, water was added thereto, and the mixture was extracted with ethyl acetate. The organic layer was washed with brine, dried over magnesium sulfate, and concentrated. The residue was purified by silica gel column chromatography, and then ethanolhydrochloric acid was added thereto to give hydrochloride. Recrystallization from ethanol gave 5.6 g of 1-(4-((5-acetyl-2-thienyl)thio) butyl)-4-(2-pyrimidinyl)piperazine hydrochloride as white crystals, m.p. 180°–181° C.

Example 2

In a similar manner as in Example 1 except the use of 2-acetyl-5-(2-chloroethylthio)thiophene in place of 2-acetyl-5(4-chlorobutylthio)thiophene, and 1-(3-trifluoromethylphenyl)piperazine in place of 2-pyrimidinylpiperazine hydrochloride, 1( 2-((5-acetyl-2-thienyl)thio)ethyl)-4-(3-trifluoromethylphenyl)piperazine hydrochloride was obtained, m.p. 175°–177° C.

Example 3

In a similar manner as in Example 1 except the use of 2-acetyl-5-(3-chloropropylthio)thiophene in place of 2-acetyl-5(4-chlorobutylthio)thiophene, and 1-(3-trifluoromethylphenyl)piperazine in place of 2-pyrimidinylpiperazine hydrochloride, 1( 3-((5-acetyl-2-thienyl)thio)propyl)-4-(3-trifluoromethylphenyl)piperazine hydrochloride was obtained, m.p. 162°–164° C.

Example 4

In a similar manner as in Example 1 except the use of 2-acetyl-5-(3-chloropropylthio)thiophene in place of 1-acetyl-5(4-chlorobutylthio)thiophene, and 1-(2,3-dimethylphenyl)piperazine in place of 2-pyrimidinylpiperazine hydrochloride, 1( 3-((5-acetyl-2-thienyl)thio)propyl)-4-(2,3-dimethylphenyl)piperazine hydrochloride, m.p. 215°–217° C.

Example 5

A mixture of 1-(2-((5-acetyl-2-thienyl)thio)ethyl)-4-(3trifluoromethylphenyl)piperazine hydrochloride (2.5 g), hydroxylamine hydrochloride (0.7 g), sodium hydrogencarbonate (1.2 g), and ethanol (50 ml) was heated under reflux for 8 hours. The reaction mixture was concentrated, and to the residue was added water, and extracted with chloroform. After washing with water and drying over magnesium sulfate, the solvent was distilled off under reduced pressure. The residue was recrystallized from isopropyl alcohol to give 1.8 g of 1-(2-((5-(1-hydroxyiminoethyl)-2 -thienyl)thio)ethyl)-4-(g-trifluoromethylphenyl)piperazine, m.p. 140°–147° C.

Example 6

In a similar manner as in Example 5 except the use of 1(3-((5-acetyl-2-thienyl)thio)propyl)-4-(3-trifluoromethylphenyl)piperazine hydrochloride in place of 1-(2-((5-acetyl-2-thienyl)- thio)ethyl)-4-(3-trifluoromethylphcnyl)piperazine hydrochloride, 1-(3-((5-(1-hydroxyiminoethyl)-2-thienyl)thio)propyl)-4-(3trifluoromethylphenyl)piperazine as a pale brown oil.

Example 7

A mixture of 1-(3-((5-(1-hydroxyiminoethyl)-2-thienyl)-thio)Propyl) -4-(3-trifluoromethylphenyl)piperazine (1.8 g) and polyphosphoric acid (20 g) was stirred while heating at 75° C. for 30 minutes. Nater was added to the reaction mixture, and the mixture was made alkaline with potassium carbonate, and extracted with ethyl acetate. The organic layer was washed with brine, dried over magnesium sulfate, and concentrated. The residue was purified by silica gel column chromatography, and recrystallized from ethyl acetate-isopropyl ether to give 0.3 g of 1-(3-((5-acetylamino-2-thienyl)thio)propyl)-4-(3trifluoromethylphenyl)piperazine ⅓ hydrate, m.p. 127–128%.

Example 8

To a solution of 1-(3-((5-acetyl-2-thienyl)thio)propyl)-4(3 -trifluoromethylphenyl)piperazine (11 g) in acetic acid (200 ml) was added a solution of sodium metaperiodate (3 g) and water (15 ml) while stirring at room temperature. The mixture was stirred at room temperature for 1 hour, poured into water, and made alkaline with potassium carbonate. The separated oily substance was extracted twice with ethyl acetate. The organic layer was collected, washed with aqueous sodium hydrogensulfite, and dried over magnesium sulfate, and the solvent was distilled off under reduced pressure. The residue was purified by silica gel column chromatography, and the oily substance obtained was added with ethanol-hydrochloric acid to give hydrochloride thereof. Recrystallization from ethanol gave 2.8 g of 1-(3((5-acetyl-2-thienyl)sulfinyl)propyl)-4-(3-trifluoromethylphenyl)piperazine hydrochloride as white crystals, m.p. 183°–184° C.

Example 9

A mixture of 2-acctyl-5-(3-chloropropylsulfonyl)thiophene (5.3 g), 2-pyrimidinylpiperazine hydrochloride (6.2 g), potassium carbonate (6 g), potassium iodide (1.3 g), dimethylformamide (50 ml), and toluene (50 ml) was stirred at 90° C. for 4 hours. The reaction mixture was cooled with water, water was added thereto, and extracted with ethyl acetate. The organic layer was washed with brine, dried over magnesium sulfate, and concentrated. The residue was purified by silica gel column chromatography, and added with ethanol-hydrochloric acid to give hydrochloride. Recrystallization from ethanol gave 1.2 g of 1-(3-((5-acetyl-2-thienyl)sulfonyl)propyl)-4-(2pyrimidinyl)piperazine hydrochloride as white crystals, m.p. 204°–205° C.

Example 10

A mixture of 1-(3-((5-acetyl-2-thicnyl)thio)propyl)-4-(2, 3dimethylphenyl)piperazine (0.9 g), sodium borohydride (0.3 g), and methanol (50 ml) was stirred at room temperature for 1 hour. Water was added to the mixture, and the mixture was extracted with ethyl acetate. The organic layer was washed with brine, dried over magnesium sulfatc, and concentrated. The residue was purified by silica gel column chromatography. The obtained oily substance was converted to maleate. Recrystallization from isopropyl alcohol gave 1-(3-((5-(1-hydroxyethyl)-2-thienyl)-thio)propyl) -4-(2,3-dimethylphcnyl)piperazine maleate as white crystals, m.p. 126°–128° C.

The following compounds were obtained in the same manner. (11) 1-(3-((5-acetyl-2-thienyl)thio)propyl)-4-(2-methoxyphenyl)piperazine hydrochloride, m.p. 168°–171° C. (12) 1-(3-((5-acetylamino-2-thienyl)thio)propyl)-4-(2-methoxyphenyl)piperazine hydrochloride monohydrate, m.p. 186°–188° C. (13) 1-(3-((3-acetyl-5-methyl-2-thienyl)thio)propyl)4-(3trifluoromethylphenyl)piperazine hydrochloride, m.p. 192°–195° C. (14) 1-(3-((5-methyl-2-thicnyl)thio)propyl)-4-(3-trifluoromethylphenyl)piperazine hydrochloride, m.p. 155°–157° C. (15) 1-(3-((5-(1-hydroxyiminoethyl)-2-thienyl)sulfonyl)propyl)4 -(3-trifluoromethylphenyl)piperazine, m.p. 152°–155° C. (16) 1-(3-((5-acetyl-2-thienyl)thio)propyl)-4-(2-pyrimidinyl)piperazine dihydrochloride, m.p. 214°–216° C. (17) 1-(3-((5-(1-hydroxyiminoethyl)-2-thienyl)thio)propyl)-4(2,3 -dimethylphenyl)piperazine, m.p. 147°–149° C. (18) 1-(3-((5-methyl-2-thicnyl)sulfonyl)propyl)-4-(3-trifluoromethylphenyl)piperazine, m.p. 82°–83° C. (19) 1-(3-(2-thienylthio)propyl)-4-(3-trifluoromethylphenyl)piperazine hydrochloride, m.p. 155°–157° C. (20) 1-(3-((5-methyl-2-thicnyl)sulfinyl)propyl)-4-(3-trifluoromethylphenyl)piperazine, m.p. 92°–94° C. (21) 3-(4-(3-((5-acctyl-2-thicnyl)thio)propyl)-l-piperadinyl)1,2 -benzisothiazole hydrochloride, m.p. 202°–203° C. (22) 1-(4-((5-acetyl-2-thienyl)thio)butyl)-4-(3-trifluoromethylphenyl)piperidine hydrochloride, m.p. 129°–131° C. (23) 1-(3-((5-acetyl-2-thicnyl)thio)propyl)-4-(4-fluorobenzoyl)piperidine maleate, m.p. 128°–130° C. (24) 1-(3-((3-acetyl-5-methyl-2-thienyl)thio)propyl)-4methylpiperazine dihydrochloridc, m.p. 242°–246° C. (25) 1-(3-((5-methyl-2-thicnyl)thio)propyl)-4-(2-methoxyphenyl)piperazine hydrochloride monohydrate, m.p. 190°–195° C. (26) 1-(3-((3-benzoyl-5-methyl-2-thienyl)thio)propyl)-4methylpiperazine dihydrochloride, m.p. 208°–211° C. (27) 1-(3-((3-benzoyl-5-methyl-2-thienyl)thio)propyl)4-(3trifluoromethylphenyl)piperazine dihydrochloride, m.p. 148°–150° C. (28) 1-(3-((5-methyl-2-thienyl)thio)propyl)-4-(2-oxo-1benzimidazolinyl)piperidine, m.p. 111°–113° C. (29) 1-(3-((3-benzoyl-5-methyl-2-thienyl)thio)propyl)-4-(2-oxo-1-benzimidazolinyl)piperidine, m.p. 186°–190° C. (30) 1-3-((3-acetyl-5-methyl-2-thienyl)thio)propyl)-4-(2methoxyphenyl)piperazine, m.p. 104°–106° C. (31) 1-(4-((5-acetyl-2-thienyl)thio)butyl)-4-(2-methoxyphenyl)piperazine dihydrochloride, m.p. 219°–220° C. (32) 1-(2-((5-acetylamino-2-thienyl)thio)ethyl)-4-(2-methoxyphenyl)piperazine, m.p. 140°–142° C. (33) 1-(3-((5-acetyl-2-thienyl)thio)propyl)-4-(3-chlorophenyl)piperazine hydrochloride ½ hydrate, m.p. 170°–173° C. (34) 1-(2-((5-acetyl-2-thienyl)thio)ethyl)-4-(2-methoxyphenyl)piperazine dihydrochloride, m.p. 201°–202° C. (35) 3-(1-(2-((5-acetyl-2-thienyl)thio)ethyl)piperidin-4-yl)-6-fluoro-1,2-benzisoxazole, m.p. 98°–101° C. (36) 3-(1-(3-((5-acetyl-2-thienyl)thio)propyl)piperidin-4-yl)-6-fluoro-1,2-benzisoxazole hydrochloride, m.p. 183°–185° C. (37) 3-(1-(4-((5-acetyl-2-thienyl)thio)butyl)piperidin-4-yl)-6-fluoro-1,2-benzisoxazole oxalate, m.p. 137°–141° C. (38) 1-(4-((5-acetyl-2-thienyl)thio)butyl)-4-(bis(4-chloro-phenyl)methyl)piperadine oxalate, m.p. 133°–137° C. (39) 1-(3-((5-acetylamino-2-thienyl)sulfonyl)propyl))-4-(3trifluoromethylphenyl)piperazine, m.p. 164°–166° C. (40) 3-(1-(3-((5-acetylamino-2-thienyl)thio)propyl)piperidin-4-yl)-6-fluoro-1,2-benzisoxazole oxalate, m.p. 114°–117° C. (41) 1-(6-((5-acetyl-2-thienyl)thio)hexyl)-4-(2-methoxyphenyl)piperazine dihydrochloride, m.p. 182°–184° C. (decomposition) (42) 3-(1-(3-((5-acetylamino-2-thienyl)thio)propyl)piperidin-4-yl)-1,2-benzisothiazole hydrochloride ½ hydrate, m.p. 227°–229° C. (decomposition) (43) 1-(3-((5-acetylamino-2-thienyl)thio)propyl)-4-(2,3dimethylphenyl)piperazine, m.p. 112°–113° C.

In the same manner, the following compounds can be obtained. (44) 3-(4-(6-((5-acetyl-2-thienyl)thio)hexyl)-l-piperazinyl-1,2benzisothiazole (45) 3-(1-(6-((5-acetyl-2-thienyl)thio)hexyl)piperidin-4-yl)-6-fluoro-1,2-benzisoxazole (46) 3-(1-(3-((5-benzoyl-2-thienyl)thio)propyl)piperidin-4-yl)6-fluoro-1,2-benzisoxazole (47) 3-(4-(3-((5-benzoyl-2-thienyl)thio)propyl)-l-piperazinyl)1,2-benzisoxazole (48) 5-((2-(4-(6-fluoro-1,2-benzisoxazol-3-yl)piperidino)ethyl)-thio)thiophene-2-carboxylic acid (49) 5-((3-(4-(6-fluoro-1,2-benzisoxazol-3-yl)piperidino)propyl)-thio)thiophene-2-carboxylic acid (50) 5-((4-(4-(6-fluoro-1,2-benzisoxazol-3-yl)piperidino)butyl)-thio)thiophene-2-carboxylic acid (51) 5-((6-(4-(6-fluoro-1,2-benzisoxazol-3-yl)piperidino)hexyl)-thio)thiophene-2-carboxylic acid (52) 3-(1-(2-((5-formyl-2-thienyl)thio)ethyl)piperidin-4-yl)-6-fluoro-1,2-benzisoxazole (53) 3-(1-(3-((5-formyl-2-thienyl)thio)propyl)piperidin-4-yl)-6-fluoro-1,2-benzisoxazole (54) 1-(3-((5-formyl-2-thienyl)thio)propyl)-4-((4-phenyl-2pyrrolyl)carbonyl)piperazine (55) 3-(1-(4-((5-formyl-2-thienyl)thio)butyl)piperidin-4-yl)-6-fluoro-1,2-benzisoxazole (56) 1-(4-((5-formyl-2-thienyl)thio)butyl)-4-((4-phenyl-2pyrrolyl)carbonyl)piperazine (57) 3-(1-(6-((5-formyl-2-thienyl)thio)hexyl)piperidin-4-yl)-6-fluoro-1, 2-benzisoxazole (58) 1-(6-((5-formyl-2-thienyl)thio)hexyl)-4-((4-phenyl-2pyrrolyl)carbonyl)piperazine (59) 3-(4-(2-((5-bromo-2-thienyl)thio)ethyl)-l-piperazinyl)-1, 2benzisothiazole (60) 1-(2-((5-bromo-2-thienyl)thio)ethyl)-4-((4-phenyl-2pyrrolyl)carbonyl)piperazine (61) 3-(1-(3-((5-bromo-2-thienyl)thio)propyl)piperidin-4-yl)-6-fluoro-1, 2-benzisoxazole (62) 1-(3-((5-bromo-2-thienyl)thio)propyl)-4-((4-phenyl-2pyrrolyl)carbonyl)piperazine (63) 3-(1-(4-((5-bromo-2-thienyl)thio)butyl)piperidin-4-yl)-6-fluoro-1,2-benzisoxazole (64) 1-(4-((5-bromo-2-thienyl)thio)butyl)-4-((4-phenyl-2pyrrolyl)carbonyl)piperazine (65) 3-(1-(6-((5-bromo-2-thienyl)thio)hexyl)piperidin-4-yl)-6-fluoro-1,2-benzisoxazole (66) 1-(6-((5-bromo-2-thienyl)thio)hexyl)-4-((4-phenyl-2pyrrolyl)carbonyl)piperazine (67) 3-(1-(2-((5-nitro-2-thienyl)thio)ethyl)piperidin-4-yl)-6-fluoro-1,2-benzisoxazole (68) 1-(2-((5-nitro-2-thienyl)thio)ethyl)-4-((4-phenyl-2pyrrolyl)carbonyl)piperazine (69) 3-(1-(3-((5-nitro-2-thienyl)thio)propyl)piperidin-4-yl)-6-fluoro-1,2-benzisoxazole (70) 1-(3-((5-nitro-2-thienyl)thio)propyl)-4-((4-phenyl-2pyrrolyl)carbonyl)piperazine (71) 3-(1-(4-((5-nitro-2-thienyl)thio)butyl)piperidin-4-yl)-6-fluoro-1,2-benzisoxazole (72) 1-(4-((5-nitro-2-thienyl)thio)butyl)-4-((4-Phenyl-2pyrrolyl)carbonyl)piperazine (73) 3-(1-(6-((5-nitro-2-thienyl)thio)hexyl)piperidin-4-yl)-6-fluoro-1,2-benzisoxazole (74) 1-(6-((5-nitro-2-thienyl)thio)hexyl)-4-((4-Phenyl-2pyrrolyl)carbonyl)piperazine (75) 1-(2-((5-amino-2-thienyl)thio)ethyl)-4-(2-methoxyphenyl)piperazine (76) 3-(1-(2-((5-amino-2-thienyl)thio)ethyl)piperidin-4-yl)-6-fluoro-1,2-benzisoxazole (77) 1-(2-((5-amino-2-thienyl)thio)ethyl)-4-((4-phenyl-2pyrrolyl)carbonyl)piperazine (78) 3-(1-(3-((5-amino-2-thienyl)thio)propyl)piperidin-4-yl)-6-fluoro-1,2-benzisoxazole (79) 1-(3-((5-amino-2-thienyl)thio)propyl)-4-(2-methoxyphenyl)piperazine (80) 1-(3-((5-amino-2-thienyl)thio)propyl)-4-((4-phenyl-2pyrrolyl)carbonyl)piperazine (81) 1-(4-((5-amino-2-thienyl)thio)butyl)-4-(2-methoxyphenyl)piperazine (82) 3-(1-(4-((5-amino-2-thienyl)thio)butyl)piperidin-4-yl)-6-fluoro-1,2-benzisoxazole (83) 3-(1-(6-((5-amino-2-thienyl)thio)hexyl)piperidin-4-yl)-6-fluoro-1,2-benzisoxazole (84) 1-(6-((5-amino-2-thienyl)thio)hexyl)-4-(2-methoxyphenyl)piperazine (85) 3-(1-(2-((5-acetylamino-2-thienyl)thio)ethyl)piperidin-4-yl)-6-fluoro-1,2-benzisoxazole (86) 3-(1-(2-((5-methylcarbamoyl-2-thienyl)thio)ethyl)piperidin-yl)-6-fluoro-1,2-benzisoxazole (87) 4-(4-fluorophenyl)-2-(4-(3-((5-acetyl-2-thienyl)thio)-propyl)piperazin-1-yl)-7,8-dihydro-5l-thiopyrano[4,3-b]pyridine oxalate ½ hydrate, m.p. 103°–106° C. (88) 2-acetyl-5-(4-(2-oxo-2,3,5,6,7,8-hexahydroimidazo[1,2a]-pyridine-3-spiro-4'-piperidino)butylthio)thiophene dihydrochloride ½ hydrate, m.p. 245°–250° C. (decomposition) (89) 2-acetyl-5-(4-(4-carbamoyl-4-piperidinopiperidino)butylthio)thiophene dihydrochloride ½ hydrate, m.p. 240°–243° C. (decomposition) (90) 3-(1-(3-((5-formyl-2-thienyl)thio)propyl)piperidin-4-yl)-6-fluoro-1,2-benzisoxazole oxalate ½ hydrate, m.p. 148°–150° C. (91) 3-(1-(3-((5-cyano-2-thienyl)thio)propyl)piperidin-4-yl)-6-fluoro-1,2-benzisoxazole oxalate ½ hydrate, m.p. 149°–151° C. (92) 3-(1-(3-((5-acetylaminoethyl-2-thienyl)sulfinyl)propyl)-piperidin-4-yl)-6-fluoro-1,2-benzisoxazole oxalate monohydrate, m.p. 128°–130° C. (93) 3-(1-(3-((5-acetylaminomethyl-2-thienyl)thio)propyl)-piperidin-4-yl)-6-fluoro-1,2-benzisoxazole fumarate ½ hydrate, m.p. 98°–100° C. (94) 3-(1-(3-(5-acetylaminomethyl-2-thienyl)thio)-2-methyl-propyl)piperidin-4-yl)-6-fluoro-1,2-benzisoxazole oxalate ½ hydrate, m.p. 77°–79° C.

Reference Example 3

To a mixture of 2-acetylaminomethylthiophene (15 g) and 4chlorobutyryl chloride (17.7 g) in dichloroethane (150 ml) was added aluminium chloride (32 g) under ice-cooling, and the mixture was stirred for 4 hours. The reaction mixture was poured into ice-water, and extracted with chloroform. The organic layer was washed with water, and dried over magnesium sulfate, and then the solvent was distilled off under reduced pressure to give 25 g of 2-acetylaminomethyl-5-(4-chlorobutyryl)thiophene.

Reference Example 4

A mixture of 2-acetylaminomethyl-5-(4-chlorobutyryl)thiophene (15 g) in triethylsilane (21.6 ml) and trifluoroacetic acid (70 ml) was stirred at room temperature for 10 hours. The reaction mixture was poured into water, extracted with ethyl acetate, and dried over magnesium sulfate, and then the solvent was distilled off under reduced pressure. The residue was purified by silica gel column chromatography to give 10 g of 2-acetylaminomethyl-5-(4-chlorobutyl)thiophene.

Example 95

A mixture of 2-acetylaminomethyl-5-(4-chlorobutyryl)thiophene (2.6 g), 4-(6-fluoro-1,2-benzisoxazol-3-yl)piperidine (2.7 g), potassium carbonate (3.0 g), potassium iodide (1.6 g), dimethylformamide (20 ml), and toluene (20 ml) was stirred at 60° C. for 6 hours. The reaction mixture was poured into water, and the precipitated crystals were filtered off, followed by recrystallization from ethanol to give 0.9 g of 3-(1-(4-(5-acetylaminomethyl -2-thienyl)-4-oxobutyl)piperidin-4-yl)-6-fluoro-1,2-benzisoxazole as white crystals, m.p. 140–142° C.

Example 96

A mixture of 2-acetylaminomethyl-5-(4-chlorobutyryl)thiophene (3 g), 1-(3-trifluoromethylphenyl)piperazine hydrobromide (4 g), potassium carbonate (3.5 g), potassium iodide (2 g), dimethylformamide (25 ml), and toluene (25 ml) was stirred at 60° C. for 7 hours. The reaction mixture was poured into water, extracted with toluene, and dried over magnesium sulfate, and then the solvent was distilled off under reduced pressure. The residue was purified by silica gel column chromatography, and converted to fumarate, followed by recrystallization from acetone to give 0.9 g of 1-(4-(5-acetylaminomethyl -2-thienyl)-4-oxobutyl)-4-(3-trifluoromethylphenyl)piperazine fumarate as white crystals, m.p. 135°–137° C.

Example 97

In a similar manner as in Example 95 except the use of 1(1,2-benzisothiazol-3-yl)piperazine in place of 4-(6-fluoro1,2-benzisoxazol-3-yl)piperidine, 3-(1-(4-(5-acetylaminomethyl2-thienyl)-4-oxobutyl) piperazin-4-yl)-1,2-benzisothiazole was obtained, m.p. 111°–114° C.

Example 98

To a solution of 3-(1-(4-(5-acetylaminomethyl-2-thienyl)-4-oxobutyl)piperazin -4-yl)-1,2-benzisothiazole (0.3 g) in water (10 ml) was added conc. sulfuric acid (0.3 ml), and the mixture was refluxed for 2 hours. The reaction mixture was poured into water, and made alkaline with potassium carbonate, followed by extraction with chloroform. The organic layer was dried over magnesium sulfate, and the solvent was distilled off under reduced pressure. The residue was converted to oxalate, and recrystallized from ethanol to give 0.1 g of 3-(1-(4-(5-aminomethyl -2-thienyl)-4-oxobutyl)piperazin-4-yl)-1,2benzisothiazole oxalate as white crystals, m.p. 200°–202° C.

Example 99

In a similar manner as in Example 1 except the use of 2-acetylaminomethyl -5-(4-chlorobutyl)thiophene in place of 2acetylaminomethyl -5-(4-chlorobutyryl)thiophene and 1-(1,2-benzisothiazol-3 -yl)piperazine in place of 4-(6-fluoro-1,2-benzisoxazol-3-yl)piperidine, 3-(1-(4-(5-acetylaminomethyl-2 thienyl)butyl)piperazin-4-yl)-1,2-benzisothiazole was obtained, m.p. 109°–111° C.

Example 100

To a solution of 3-(1-(4-(5-aminomethyl-2-thienyl)-4-oxobutyl)piperazin -4-yl)-1,2-benzisothiazole (1.5 g), triethylamine (5 ml), and tetrahydrofuran (10 ml) was added benzoylchloride (2 ml) under ice-cooling, and the mixture was stirred for 30 minutes. The reaction mixture was poured into water, and the precipitated crystals were filtered off, and recrystallized from isopropyl alcohol to give 1.4 g of 3-(1-(4(5-(2 -benzoylaminomethyl)-2-thienyl)-4-oxobutyl)piperazin-4-yl)1,2-benzisothiazole as white crystals, m.p. 107°–109° C.

In a similar manner, the following compounds were obtained. (101) 3-(1-(4-(5-methylcarbamoylmethyl-2-thienyl)-4-oxobutyl)-piperazin -4-yl)-1,2-benzisothiazole, m.p. 118°–120° C. (102) 1-(4-(5-acetylaminomethyl-2-thienyl)-4-oxobutyl)-4-(5-trifluoromethyl-2-pyridyl) piperazine, m.p. 176–178° C. (103) 3-(1-(4-(5-(1-acetylaminoethyl)-2-thienyl)-4-oxobutyryl)-piperidin -4-yl)-6-fluoro-1,2-benzisoxazole, m.p. 124°–127° C. (104) 3-(1-(4-(5-(2-acetylaminoethyl)-2-thienyl)-4-oxobutyl)-piperazin -4-yl)-1,2-benzisothiazole hydrochloride ½ hydrate, m.p. 207°–208° C. (decomposition) (105) 3-(1-(4-(5-(2-acetylaminoethyl))-2-thienyl)-4-oxobutyl)-piperidin -4-yl)-6-fluoro-1,2-benzisoxazole, m.p. 139°–140° C. (106) 3-(1-(4-(5-methylcarbamoylmethyl-2-thienyl)-4-oxobutyl)-piperidin -4-yl)-6-fluoro-1,2-benzisoxazole, m.p. 147°–148° C. (107) 3-(1-(3-(5-acetylaminomethyl-2-thienyl)-3-oxopropyl)-piperidin -4-yl)-6-fluoro-1,2-benzisoxazole, m.p. 149°–150° C. (108) 3-(1-(4-(5-acetylaminomethyl-2-thienyl)butyl)piperidin-4-yl) -6-fluoro-1,2-benzisoxazole, m.p. 73°–75° C. (109) 3-(1-(4-(5-(3-fluorobenzoylaminomethyl)-2-thienyl)-4-oxobutyl)piperidin -4-yl)-6-fluoro-1,2-benzisoxazole oxalate ½ hydrate, m.p. 155°–157° C. (110) 3-(1-(4-(5-carbamoylmethyl-2-thienyl)-4-oxobutyl)-piperidin -4-yl)-6-fluoro-1,2-benzisoxazole hydrate, m.p. 146°–147° C. (111) 3-(1-(2-(5-acetylaminomethyl-2-thienyl)-2-oxoethyl)-piperidin -4-yl)-6-fluoro-1,2-benzisoxazole, m.p. 132°–134° C. (112) 3-(1-(4-(5-trifluoroacetylaminomethyl-2-thienyl)-4-oxobutyl)piperidin -4-yl)-6-fluoro-1,2-benzisoxazole, m.p. 113°–115° C. (113) 3-(1-(4-(5-propionylaminomethyl-2-thienyl)-4-oxobutyl)-piperazin -4-yl)-1,2-benzisothiazole, m.p. 75°–77° C. (114) 3-(1-(4-(5-mesylaminomethyl-2-thienyl)-4-oxobutyl)-piperazin -4-yl)-1,2-benzisothiazole hydrochloride hydrate, m.p. 216°–219° C. (115) 3-(1-(4-(5-butyl-2-thienyl)-4-oxobutyl)piperidin-4-yl)-6-fluoro-1,2 -benzisoxazole hydrochloride, m.p. 202°–203° C. (116) 3-(1-(4-(2-thienyl)-4-oxobutyl)piperidin-4-yl)-6-fluoro-1,2-benzisoxazole, m.p. 97°–99° C. (117) 3-(1-(6-(5-acetylaminomethyl-2-thienyl)-6-oxohexyl)-piperidin -4-yl)-6-fluoro-1,2-benzisoxazole, m.p. 107°–109° C. (118) 3-(1-(5-(5-acetylaminomethyl-2-thienyl)-5-oxopentyl)-piperidin -4-yl)-6-fluoro-1,2-benzisoxazole, m.p. 154°–156° C. (119) 3-(1-(2-(5-acetylaminomethyl-2-thienyl)ethyl)piperidin-4-yl)-6-fluoro -1,2-benzisoxazole, m.p. 98°–99° C. (120) 3-(1-(2-(5-acetylaminomethyl-2-thienyl)-2-hydroxyethyl)-piperidin -4-yl)-6-fluoro-1,2-benzisoxazole hydrochloride ½ hydrate, m.p. 102°–104° C. (121) 3-(1-(2-(5-acetylmethylaminomethyl-2-thienyl)-2-oxoethyl)-piperidin -4-yl)-6-fluoro-1,2-benzisoxazole hydrochloride ¼ hydrate, m.p. 112°–114° C.

In the same manner, the following compounds can be obtained. (122) 3-(1-(4-(5-bromo-2-thienyl)-4-oxobutyl)piperazin-4-yl)1,2-benzisothiazole (123) 3-(1-(4-(5-nitro-2-thienyl)-4-oxobutyl)piperazin-4-yl)1,2-benzisothiazole (124) 3-(1-(4-(5-amino-2-thienyl)-4-oxobutyl)piperazin-4-yl)1,2-benzisothiazole (125) 3-(1-(4-(5-formyl-2-thienyl)-4-oxobutyl)piperazin-4-yl)1,2-benzisothiazole (126) 5-(4-(4-(1,2-benzisothiazol-3-yl)-1-piperazinyl)butyryl)-thiophene-2-carboxylic acid (127) 3-(1-(4-(5-methyl-2-thienyl)-4-oxobutyl)piperazin-4-yl)-6-fluoro-1,2-benzisoxazole (128) 3-(1-(4-(5-acetylaminomethyl-3-methyl-2-thienyl)-4-oxobutyl)piperidin -4-yl)-6-fluoro-1,2-benzisoxazole (129) 3-(1-(4-(5-acetyl-2-thienyl)butyl)piperidin-4-yl)-6-fluoro-1,2-benzisoxazole (130) 3-(1-(4-(5-acctylaminomethyl-2-thienyl)-4-hydroxybutyl)-piperidin-4-yl) -6-fluoro-1,2-benzisoxazole (131) 3-(1-(4-(5-acctylaminomethyl-2-thicnyl)-4-hydroxybutyl)-piperidin-4-yl) -1,2-benzisothiazole (132) 3-(1-(4-(5-benzoyl-2-thienyl)butyl)piperidin-4-yl)-6-fluoro-1,2-benzisoxazole (133) 1-(4-(5-hydroxymethyl-2-thienyl)butyl)-4-(3-trifluoromethylphenyl)piperazine (134) 1-(4-(5-acetoxymethyl-2-thienyl)butyl)-4-(3-trifluoromethylphenyl)piperazine (135) 1-(4-(5-acetylamino-2-thicnyl)-4-oxobutyl)-4-(3-chlorophenyl)piperazine (136) 1-(4-(5-benzoyloxymethyl-2-thienyl)butyl)-4-(2-methoxyphenyl)piperazine (137) 1-(3-(5-phenylacetylamino-2-thienyl)propyl)-4-phenylpiperazine (138) 3-(1-(3-(5-benzoylamino-2-thienyl)propyl)piperazin-4-yl)-1, 2-benzisothiazole (139) 3-(1-(3-(5-formylaminomethyl-2-thienyl)-3-oxopropyl)-piperazin -4-yl)-1,2-benzisothiazole (140) 1'-(4-(5-scetylaminomethyl-2-thienyl)-4-oxobutyl)2,3,5,6,7,8 -hexahydro-2-oxoimidazo[1,2-a]pyridine-3-spiro-4'-piperidine (141) 1-(2-(5-benzyl-2-thienyl)-2-oxoethyl)-4-(4-chlorophenyl)-hydroxypiperidine (142) 3-(1-(4-(5-acetylaminomethyl-2-thienyl)-4-oxobutyl)-piperazin -4-yl)-1,2-benzisothiazole S,S-dioxide (143) 2-(1-(4-(5-acetylaminomethyl-2-thienyl)-4-oxobutyl)-piperazin -4-yl)-4-phenylthiazole (144) 3-(1-(4-(5-acetylaminomethyl-2-thienyl)-4-oxobutyl)-piperazin-4-yl)indole (145) 1-(4-(5-acetylaminomethyl-2-thicnyl)-2,2-dimethyl-4-oxobutyl) -4-(2-methoxyphenyl)piperazine (146) 1-(4-(5-acetylaminomethyl-2-thienyl)-4-oxobutyl)-4-(2pyrimidinyl)piperazine (147) 1-(4-(5-acetylaminomethyl-2-thienyl)-4-oxobutyl)-4-(5-fluoro-2-pyrimidinyl) piperazine (148) 1-(4-(5-acctylaminomethyl-2-thienyl)-4-oxobutyl)-4-Phenylcarbamoylpiperazine (149) 1-(4-(5-acetylaminomethyl-2-thicnyl)-4-oxobutyl)-4ethylcarbamoylpiperazine (150) 3-(1-(4-(5-acetylaminomethyl-2-thienyl)-4-hydroxybutyl)-piperidin -4-yl)-6-fluoro-1,2-benzisocazole oxalatc, m.p. 117°–120° C. (151) 3-(1-(2-(5-acetylaminomethyl-4-methyl-2-thienyl)ethyl)-piperadin -4-yl)-6-fluoro-1,2-benzisoxazole, m.p. 139°–140° C. (152) 1-(2-(5-acetylaminomethyl-2-thienyl)ethyl)-4-(2-pyrimidinyl)piperazine, m.p. 103°–105° C. (153) 1-(2-(5-acetylaminomethyl-2-thienyl)ethyl)-4-(4-chlorophenyl)-4-hydroxypiperidine, m.p. 131°–134° C. (154) 3-(4-(2-(5-acetylaminomethyl-2-thienyl)ethyl)piperazin-1-yl)-1,2-benzisoxazole, m.p. 99°–100° C. (155) 3-(1-(2-(5-acetylaminomethyl-2-methyl-3-thienyl)ethyl)-piperidin -4-yl)-6-fluoro-1,2-benzisoxazole, m.p. 141°–143° C. (156) 1-(2-(5-acetylaminomethyl-2-thienyl)ethyl)-4-(bis(4fluorophenyl)methylene)piperidin oxalate, m.p. 137°–138° C. (157) 1'-(2-(5-acetylaminomethyl-2-thienyl)ethyl)-4-(2-oxo-1,2,3,5,6,7,8a -octahydroimidazol [1,2-a]pyridine-3-spiro)piperidine dihydrochloride ½ hydrate, m.p. 247°–249° C. (158) 3-(1-(2-(5-(2-acetylaminoethyl)-2-thienyl)ethyl)piperidin-4-yl) -6-fluoro-1,2-benzisoxazole ½ hydrate, m.p. 101°–103° C. (159) 3-(1-(2-(5-(2-acetylaminoethyl)-4-bromo-2-thienyl)ethyl)-piperidin-4-yl) -6-fluoro-1,2-benzisoxazole, m.p. 119°–121° C. (160) 4-(2-(5-acetylaminomethyl-2-thienyl)ethyl)-N-cyclohexyl-1piperazinecarboxamide, m.p. 188°–190° C. (161) 4-(2-(5-acetylaminomethyl-2-thienyl)ethyl)-N-phenyl-1piperazinecarboxamide, m.p. 182°–184° C. (162) 3-(1-(2-(5-phenylacetylaminomethyl-2-thienyl)ethyl)-piperidin -4-yl)-6-fluoro-1,2-benzisoxazole, m.p. 117°–119° C. (163) 4-(2-(5-acetylaminomethyl-2-thienyl)ethyl)-N-ethyl-1piperazinecarboxamide, m.p. 155°–157° C. (164) 3-(1-(2-(5-aminomethyl-2-thienyl)ethyl)piperidin-4-yl)-6-fluoro-1,2-benzisoxazole, m.p. 80°–82° C. (165) 3-(1-(4-(5-aminomethyl-2-thienyl)butyl)piperidin-4-yl)-6-fluoro-1,2-benzisoxazole hydrochloride ½ hydrate, m.p. 255° C. or above (166) 3-(1-(2-(5-dimethylaminomethyl-2-thienyl)ethyl)piperidin-4-yl) -6-fluoro-1,2-benzisoxazole oxalate, m.p. 122°–125° C.

Formulation Example

Tablets containing 10 mg of the compound of the formula (I) can be prepared according to the following formulation.

| Compound of formula (I) | 10.0 mg |
|---|---|
| Lactose | 58.5 mg |
| Corn starch | 25.0 mg |
| Crystalline cellulose | 20.0 mg |
| Polyvinylpyrrolidone K-30 | 2.0 mg |
| Talc | 4.0 mg |
| Magnesium stearate | 0.5 mg |
| | 120.0 mg |

The compound of the formula (I) is pulverized in an atomizer to give a fine powder having an average particle size of 10 μ or less. The powder was thoroughly mixed with lactose, corn starch, and crystalline cellulose in a kneadcr, and kneaded with polyvinylpyrrolidone paste. The kneaded substance is passed through a 20 mesh sieve, dried at 50° C., and passed through a 24 mesh sieve. Talc and magnesium stearate are mixed in, and 120.0 mg tablets are obtained with a pounder having a diameter of 8 mm. The obtained tablets may be coated with sugar or a film where necessary.

While the present invention has been adequately and sufficiently described in the foregoing specification and examples, it should be understood that the present invention is susceptible to various changes and modifications falling within the spirit and scope of the invention.

What is claimed is:

1. A thiophene compound of the formula

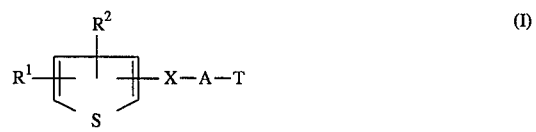

wherein $R^1$ and $R^2$ are the same or different and each (1) hydrogen, (2) halogen, (3) nitro, (4) amino, (5) cyano, (6) alkyl of 1 to 8 carbon atoms, (7) mono- or di-alkylamino wherein the alkyl moiety is of 1 to 4 carbon atoms, (8) formyl, (9) -COOR$^3$ wherein R$^3$ is hydrogen, alkyl of 1 to 8 carbon atoms or an ester residue hydrolyzable in the body,

(10) alkoxy of 1 to 8 carbon atoms,

(11) hydroxyalkyl of 1 to 4 carbon atoms,

(12) haloalkyl of 1 to 4 carbon atoms,

(13) haloalkoxy of 1 to 4 carbon atoms,

(14) alkanoyl of 2 to 5 carbon atoms,

(15) benzoyl,

(16) naphthoyl,

(17) phenylalkanoyl wherein the alkanoyl moiety has 2 to 5 carbon atoms,

(18) alkanoyloxyalkyl wherein the alkanoyl moiety has 1 to 5 carbon atoms and the alkyl moiety has 1 to 4 carbon atoms,

(19) benzoyloxyalkyl wherein the alkyl moiety has 1 to 4 carbon atoms,

(20) formylamino,

(21) alkanoylamino having 2 to 5 carbon atoms,

(22) phenylalkanoylamino wherein the alkanoyl moiety has 2 to 5 carbon atoms,

(23) benzoylamino,

(24) naphthoylamino,

(25) formylaminoalkyl wherein the alkyl moiety has 1 to 4 carbon atoms,

(26) alkanoylaminoalkyl wherein the alkanoyl moiety has 2 to 5 carbon atoms and the alkyl moiety has 1 to 4 carbon atoms,

(27) haloalkanoylaminoalkyl wherein the alkanoyl moiety has 2 to 5 carbon atoms and the alkyl moiety has 1 to 4 carbon atoms,

(28) phenylalkanoylaminoalkyl wherein the alkanoyl moiety has 2 to 5 carbon atoms and the alkyl moiety has 1 to 4 carbon atoms,

(29) benzoylaminoalkyl wherein the alkyl moiety has 1 to 4 carbon atoms,

(30) phenylalkyl wherein the alkyl moiety has 1 to 6 carbon atoms,

(31) carbamoyl,

(32) carbamoyl mono- or di-substituted by alkyl of 1 to 4 carbon atoms, cyclohexyl, phenyl or benzyl,

(33) carbamoylalkyl wherein the alkyl moiety has 1 to 4 carbon atoms,

(34) carbamoylalkyl mono- or di-substituted by alkyl of 1 to 4 carbon atoms or benzyl and the alkyl moiety having 1 to 4 carbon atoms,

(35) aminoalkyl wherein the alkyl moiety has 1 to 4 carbon atoms,

(36) aminoalkyl mono- or di-substituted by alkyl of 1 to 4 carbon atoms and the alkyl moiety having 1 to 4 carbon atoms,

(37) alkylsulfonylaminoalkyl wherein the alkyl moieties respectively have 1 to 4 carbon atoms,

(38) hydroxyiminoalkyl wherein the alkyl moiety has 1 to 4 carbon atoms, or

(39) alkoxyiminoalkyl wherein the alkoxy and alkyl moieties respectively have 1 to 4 carbon atoms;

X is (1) -S(O)$_n$- wherein n is 0, 1 or 2, (2) -CO-, (3) -CH(OR$^{10}$)- wherein R$^{10}$ is hydrogen, alkyl of 1 to 8 carbon atoms, alkanoyl of 2 to 5 carbon atoms or benzoyl, or (4) -CH$_2$-;

A is alkylene of 1 to 10 carbon atoms; and

T is

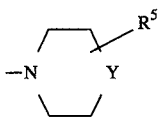

wherein

R$^5$ is hydrogen, and

Y is (a) C(R$^6$) (R$^7$) wherein

R$^6$ is hydrogen, and

R$^7$ is 1,2-benzisothiazol or 1,2-benzisoxazol which groups are unsubstituted or are substituted by 1 to 3 substituents selected from the group consisting of halogen, nitro, amino, cyano, haloalkyl of 1 to 4 carbon atoms, hydroxy, alkyl of 1 to 4 carbon atoms, alkoxy of 1 to 4 carbon atoms, alkenyl of 2 to 4 carbon atoms and phenyl, or R$^6$ and R$^7$ taken together form (1) diphenylmethylene, (2) bis(4-fluorophenyl)methylene, or (3) bis (4-chlorophenyl)-methylene, or (b) N-R$^8$ wherein R$^8$ is phenyl, pyrimidinyl, 1,2-benzisothiazol or 1,2-benzisoxazol which groups are unsubstituted or are substituted by 1 to 3 substituents selected from the group consisting of halogen, nitro, amino, cyano, haloalkyl of 1 to 4 carbon atoms, hydroxy, alkyl of 1 to 4 carbon atoms, alkoxy of 1 to 4 carbon atoms, alkenyl of 2 to 4 carbon atoms and phenyl;

with the proviso that when

X is -CO-, -CH(OR$^{10}$)-, -CH$_2$-, -C(=NOR$^{11}$)- or -CH(NH$_2$)

wherein R$^{10}$ and R$^{11}$ are as defined above, and

Y is one of the following (i) C(R$^6$)(R$^7$) wherein R$^6$ and R$^7$ together form diphenylmethylene, bis(4-fluorophenyl)methylene or bis(4-chlorophenyl)methylene, or (ii) N-R$^8$ wherein R$^8$ is phenyl which is unsubstituted or is substituted by 1 to 3 substituents selected from the group consisting of halogen, nitro, amino, cyano, haloalkyl of 1 to 4 carbon atoms, hydroxy, alkyl of 1 to 4 carbon atoms, alkoxy of 1 to 4 carbon atoms, alkenyl of 2 to 4 carbon atoms, and phenyl then, in such case, at least one of R$^1$ and R$^2$ is a group other than hydrogen, halogen, nitro, alkyl of 1 to 8 carbon atoms and alkoxy of 1 to 8 carbon atoms, or a pharmaceutically acceptable salt of said thiophene compound.

2. A thiophene compound according to claim 1, wherein R$^1$ is (1) amino, (2) cyano, (3) amino mono- or di-substituted by alkyl having 1 to 4 carbon atoms,

31

(4) formyl,
(5) -COOR$^3$ wherein R$^3$ is hydrogen, alkyl of 1 to 8 carbon atoms or an ester residue hydrolyzable in the body,
(6) hydroxyalkyl having 1 to 4 carbon atoms,
(7) haloalkyl having 1 to 4 carbon atoms,
(8) haloalkoxy having 1 to 4 carbon atoms,
(9) alkanoyl having 2 to 5 carbon atoms,
(10) benzoyl,
(11) naphthoyl,
(12) phenylalkanoyl wherein the alkanoyl moiety has 2 to 5 carbon atoms,
(13) alkanoyloxyalkyl wherein the alkanoyl moiety has 1 to 5 carbon atoms and the alkyl moiety has 1 to 4 carbon atoms,
(14) benzoyloxyalkyl wherein the alkyl moiety has 1 to 4 carbon atoms,
(15) formylamino,
(16) alkanoylamino having 2 to 5 carbon atoms,
(17) phenylalkanoylamino wherein the alkanoyl moiety has 2 to 5 carbon atoms,
(18) benzoylamino,
(19) naphthoylamino,
(20) formylaminoalkyl wherein the alkyl moiety has 1 to 4 carbon atoms,
(21) alkanoylaminoalkyl wherein the alkanoyl moiety has 2 to 5 carbon atoms and the alkyl moiety has 1 to 4 carbon atoms,
(22) haloalkanoylaminoalkyl wherein the alkanoyl moiety has 2 to 5 carbon atoms and the alkyl moiety has 1 to 4 carbon atoms,
(23) phenylalkanoylaminoalkyl wherein the alkanoyl moiety has 2 to 5 carbon atoms and the alkyl moiety has 1 to 4 carbon atoms,
(24) benzoylaminoalkyl wherein the alkyl moiety has 1 to 4 carbon atoms,
(25) phenylalkyl wherein the alkyl moiety has 1 to 6 carbon atoms,
(26) carbamoyl,
(27) carbamoyl mono- or di-substituted by alkyl having 1 to 4 carbon atoms, cyclohexyl, phenyl or benzyl,
(28) carbamoylalkyl wherein the alkyl moiety has 1 to 4 carbon atoms,
(29) carbamoylalkyl mono- or di-substituted by an alkyl having 1 to 4 carbon atoms or benzyl, and the alkyl moiety having 1 to 4 carbon atoms,
(30) aminoalkyl wherein the alkyl moiety has 1 to 4 carbon atoms,
(31) aminoalkyl mono- or di-substituted by alkyl having 1 to 4 carbon atoms, and the alkyl moiety having 1 to 4 carbon atoms,
(32) alkylsulfonylaminoalkyl wherein the alkyl moieties respectively have 1 to 4 carbon atoms,
(33) hydroxyiminoalkyl wherein the alkyl moiety has 1 to 4 carbon atoms, or
(34) alkoxyiminoalkyl wherein the alkoxy moiety and the alkyl moiety respectively have 1 to 4 carbon atoms;
R$^2$ is (1) hydrogen, (2) halogen, (3) nitro, (4) cyano, or (5) alkyl having 1 to 8 carbon atoms;
X is (1) -S (0) n- wherein n is 0,1 or 2, (2) -CO-, (3) -CH(OR$^{10}$)- wherein R$^{10}$ is hydrogen, alkyl having 1 to

32

8 carbon atoms, alkanoyl having 2 to 5 carbon atoms or benzoyl, or
A is alkylene having 1 to 10 carbon atoms; and
T is $$-N\underset{\diagdown\quad\diagup}{\overset{\diagup\quad\diagdown}{\phantom{XX}Y\phantom{XX}}}\!\!\!R^5$$

wherein
R$^5$ is hydrogen, and
Y is (a) C(R$^6$) (R$^7$) wherein
R$^6$ is hydrogen, and
R$^7$ is 1,2-benzisothiazol or 1,2-benzisoxazol which groups are unsubstituted or are substituted by 1 to 3 substituents selected from the group consisting of halogen, nitro, amino, cyano, haloalkyl having 1 to 4 carbon atoms, hydroxy, alkyl having 1 to 4 carbon atoms, alkoxy having 1 to 4 carbon atoms, alkenyl having 2 to 4 carbon atoms and phenyl,
or R$^6$ and R$^7$ taken together form (1) diphenylmethylene, (2) bis (4-fluorophenyl)methylene or (3) bis-(4-chlorophenyl)methylene, or
(b) N-R$^8$ wherein R$^8$ is phenyl, pyrimidinyl, 1,2-benzisothiazol or 1,2-benzisoxazol which groups are unsubstituted or are substituted by 1 to 3 substituents selected from the group consisting of halogen, nitro, amino, cyano, haloalkyl having 1 to 4 carbon atoms, hydroxy, alkyl having 1 to 4 carbon atoms, alkoxy having 1 to 4 carbon atoms, alkenyl having 2 to 4 carbon atoms and phenyl;
or a pharmaceutically acceptable salt of said thiophene compound.

3. A thiophene compound according to claim 1, wherein;
R$^1$ is (1) formyl,
(2) hydroxyalkyl having 1 to 4 carbon atoms,
(3) haloalkyl having 1 to 4 carbon atoms,
(4) alkanoyl having 2 to 5 carbon atoms,
(5) benzoyl,
(6) naphthoyl,
(7) alkanoylamino having 2 to 5 carbon atoms,
(8) alkanoylaminoalkyl wherein the alkanoyl moiety has 2 to 5 carbon atoms and the alkyl moiety has 1 to 4 carbon atoms,
(9) haloalkanoylaminoalkyl wherein the alkanoyl moiety has 2 to 5 carbon atoms and the alkyl moiety has 1 to 4 carbon atoms,
(10) phenylalkanoylaminoalkyl wherein the alkanoyl moiety has 2 to 5 carbon atoms and the alkyl moiety has 1 to 4 carbon atoms,
(11) benzoylaminoalkyl wherein the alkyl moiety has 1 to 4 carbon atoms,
(12) carbamoylalkyl wherein the alkyl moiety has 1 to 4 carbon atoms,
(13) carbamoylalkyl mono- or di-substituted by alkyl having 1 to 4 carbon atoms or benzyl, and the alkyl moiety has 1 to 4 carbon atoms,
(14) aminoalkyl wherein the alkyl moiety has 1 to 4 carbon atoms,
(15) aminoalkyl mono- or di-substituted by an alkyl having 1 to 4 carbon atoms, and the alkyl moiety having 1 to 4 carbon atoms,

(16) alkylsulfonylaminoalkyl wherein the alkyl moieties respectively have 1 to 4 carbon atoms, or

(17) hydroxyiminoalkyl wherein the alkyl moiety has 1 to 4 carbon atoms;

$R^2$ is (1) hydrogen, (2) halogen, (3) nitro, (4) cyano, or (5) alkyl having 1 to 8 carbon atoms;

X is (1) -S(O)$_n$- wherein n is 0,1 or 2, (2) -CO-, (3) -CH(OR$^{10}$)- wherein $R^{10}$ is hydrogen, alkyl having 1 to 8 carbon atoms, alkanoyl having 2 to 5 carbon atoms or benzoyl, or (4) -CH$_2$-;

A is alkylene having 1 to 10 carbon atoms; and

T is $$-N\diagup\diagdown Y \diagdown\diagup^{R^5}$$

wherein $R^5$ is hydrogen,

Y is (a) C ($R^6$) ($R^7$) wherein $R^6$ is hydrogen, and $R^7$ is 1,2-benzisothiazol or 1,2-benzisoxazol which groups are unsubstituted or are substituted by 1 to 3 substituents selected from the group consisting of halogen, nitro, amino, cyano, haloalkyl having 1 to 4 carbon atoms, hydroxy, alkyl having 1 to 4 carbon atoms, alkoxy having 1 to 4 carbon atoms, alkenyl having 2 to 4 carbon atoms and phenyl, or $R^6$ and $R^7$ taken together form (1) diphenylmethylene, (2) bis(4-fluorophenyl)methylene, or (3) bis(4-chlorophenyl)methylene), or (b) N-$R^8$ wherein $R^8$ is phenyl, pyrimidinyl, 1,2-benzisothiazol or 1,2-benzisoxazol which groups are unsubstituted or are substituted by 1 to 3 substituents selected from the group consisting of halogen, nitro, amino, cyano, haloalkyl having 1 to 4 carbon atoms, hydroxy, alkyl having 1 to 4 carbon atoms, alkoxy having 1 to 4 carbon atoms, alkenyl having 2 to 4 carbon atoms and phenyl;

or a pharmaceutically acceptable salt of said thiophene compound.

4. A thiophene compound according to claim 1, wherein;

$R^1$ is (1) alkanoyl having 2 to 5 carbon atoms, (2) alkanoylamino having 2 to 5 carbon atoms, (3) alkanoylaminoalkyl wherein the alkanoyl moiety has 2 to 5 carbon atoms and the alkyl moiety has 1 to 4 carbon atoms, (4) benzoylaminoalyl wherein the alkyl moiety has 1 to 4 carbon atoms, or (5) alkylsulfonylaminoalkyl wherein the alkyl moieties respectively have 1 to 4 carbon atoms;

$R^2$ is (1) hydrogen, (2) halogen, or (3) alkyl having 1 to 8 carbon atoms;

X is (1) -S(O)$_n$- wherein n is 0,1 or 2, (2) -CO-, or (3) -CH$_2$-;

A is alkylene having 1 to 10 carbon atoms; and

T is $$-N\diagup\diagdown Y \diagdown\diagup^{R^5}$$

wherein $R^5$ is hydrogen,

Y is (a) C($R^6$)($R^7$) wherein $R^6$ is hydrogen, and $R^7$ is 1,2-benzisothiazol or 1,2-benzisoxazol which groups are unsubstituted or are substituted by 1 to 3 halogen substituents, or $R^6$ and $R^7$ taken together form bis(4-fluorophenyl)methylene, or (b) N-$R^8$ wherein $R^8$ is phenyl, pyrimidinyl, 1,2 benzisothiazol or 1,2-benzisoxazol which groups are unsubstituted or are substituted by 1 to 3 substituents selected from the group consisting of halogen, haloalkyl having 1 to 4 carbon atoms, alkyl having 1 to 4 carbon atoms and alkoxy having 1 to 4 carbon atoms;

or a pharmaceutically acceptable salt of said thiophene compound.

5. A thiophene compound according to claim 1, said compound being one selected from the group consisting of 3-(4-(3-((5-acetyl-2-thienyl)thio)propyl)-1-piperazinyl)-1, 2benzisothiazole, 3-(1-(3-((5-acetyl-2-thienyl)thio)propyl)piperidin-4-yl)-6-fluoro-1,2-benzisoxazole, 3-(1-(3-((5-acetylamino-2-thienyl)thio)propyl)piperidin-4-yl)-6-fluoro-1,2-benzisoxazole, 3-(1-(3-((5-acetylaminomethyl-2-thienyl)thio)propyl)piperidin-4-yl)-6-fluoro-1,2-benzisoxazole, 3-(1-(4-(5-acetylaminomethyl-2-thienyl)-4-oxobutyl)piperidin-4yl)-6-fluoro-1,2 -benzisoxazole, 3-(1-(4-(5-acetylaminomethyl-2-thienyl)butyl)piperidin-4-yl)-6-fluoro-1,2-benzisoxazole, 3-(1-(2-(5-acetylaminomethyl-2-thienyl)ethyl)piperidin-4-yl)-6-fluoro -1,2-benzisoxazole, 3-(1-(2-(5-acetylaminomethyl-4-methyl-2-thlenyl)ethyl)-piperldin-4 -yl)-6-fluoro-1,2-benzlsoxazole, 3-(1-(2-(5-acetylaminomethyl-2-methyl-3-thienyl)ethyl)-piperidin-4 -yl)-6-fluoro-1,2-benzisoxazole, 3-(1-(2-(5-(2-acetylamino-ethyl)-2-thienyl)ethyl)piperidin-4-yl) -6-fluoro-1,2-benzisoxazole, 3-(1-(2-(5-(2-acetylaminoethyl)-4-bromo-2-thienyl)ethyl)piperidin-4 -yl)-6-fluoro-1,2-benzisoxazole, 3-(1-4-(5-acetylamino-2-thienyl)butyl)piperldin-4-yl)-6-fluoro-1,2-benzisoxazole, 1-(4-((5-acetyl-2-thienyl)thio)butyl)-4-(2-pyrimidinyl)piperazine, 1-(3-[(5-acetyl-2-thienyl)thio)propyl)-4-(2,3-dimethylphenyl)piperazine, 1-(3-((5-acetylamino-2-thienyl)thio)propyl)-4-(3trifluoromethylphenyl)piperazine, 1-(3-((5-acetylamino-2-thienyl)thio)propyl)-4-(2methoxyphenyl)piperazine, 1-(3-((5-acetyl-2-thienyl)thio)propyl)-4-(3-chlorophenyl)piperazine, 3-(1-(2-((5-acetyl-2-thienyl)thio)ethyl)piperidin-4-yl)-6-fluoro-1,2-benzisoxazole, 3-(1-(4-((5-acetyl-2-thienyl)thio)butyl)piperidin-4-yl)-6-fluoro-1,2-benzisoxazole, 1-(6-((5-acetyl-2-thienyl)thio)hexyl)-4-(2-methoxyPhenyl)piperazine, 1-(3-((5-acetylamino-2-thienyl)thio)propyl)-4-(2,3dimethylphenyl)piperazine, 1-(4-(5-acetylaminomethyl-2-thienyl)-4-oxobutyl)-4-(3-trifluoromethylphenyl)piperazine, 3-(1-(4-(5-acetylaminomethyl-2-thienyl)-4-oxobutyl)piperazin-4-yl)-

1,2-benzisothiazole, 3-(1-(4-(5-acetylaminomethyl-2-thienyl)butyl)piperazin-4-yl)-1,2-benzisothiazole, 3-(1-(4-(5-(2-benzoylaminomethyl)-2-thienyl)-4-oxobutyl)-piperazin-4-yl) -1,2-benzisothiazole, 3-(1-(4-(5-propionylaminomethyl)-2-thienyl)-4-oxobutyl)-piperazin-4-yl) -1,2-benzisothiazole, 3-(1-(4-(5-mesylaminomethyl)-2-thienyl)-4-oxobutyl)piperazin-yl) -1,2-benzisothiazole, 3-(1-(6-(5-acetylaminomethyl-2-thienyl)-6-oxohexyl)piperidin-yl) -6-fluoro-1,2-benzisoxazole, 3-(4-(2-(5-acetylaminomethyl )-2-thienyl )ethyl )piperazin-1-yl )1,2-benzisoxazole, and 1-(2-(5-acetylaminomethyl-2-thienyl)ethyl)-4-(bis(4fluorophenyl)methylene)piperidine, and a pharmaceutically acceptable salt of said compound.

6. A thiophene compound according to claim 1, wherein:

R¹ is alkanoyl having 2 to 5 carbon atoms, (2) alkanoylamino having 2 to 5 carbon atoms, or (3) alkanoylaminoalkyl wherein the alkanoyl moiety has 2 to 5 carbon atoms and the alkyl moiety has 1 to 4 carbon atoms;

R² is (1) hydrogen, (2) halogen, or (3) alkyl having 1 to 4 carbon atoms;

x is -S(O)$_n$- wherein n is 0, 1 or 2, (2) -CO-, or (3) -CH$_2$-;

A is alkylene having 1 to 6 carbon atoms; and

T is

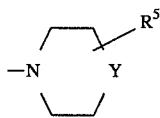

wherein R⁵ is hydrogen, and

Y is C(R⁶)(R⁷) wherein

R⁶ is hydrogen, and

R⁷ is 1,2-benzisothiazol or 1,2-benzisoxazol which groups are unsubstituted or are substituted by 1 to 3 halogen substituents;

or a pharmaceutically acceptable salt of said thiophene compound.

7. A thiophene compound according to claim 1, wherein:

R¹ is acetyl, acetylamino, acetylaminomethyl or 2-acetylaminoethyl;

R² is hydrogen, halogen or methyl;

X is (1) -S (O)$_n$- wherein n is 0, 1 or 2, (2) -CO-, or (3) -CH$_2$-;

A is methylene, ethylene or trimethylene; and

T is 4-(1,2-benzisothiazol-3-yl)-1-piperadinyl or 4-(6-fluoro-1,2 -benzisoxazol-3-yl)piperidino;

or a pharmaceutically acceptable salt of said thiophene compound.

8. A thiophene compound according to claim 1, said compound being one selected from the group consisting of 3-(4-(3-((5-acetyl-2-thienyl)thio)propyl)-1-piperazinyl)-1,2-benzisothiazole, 3-(1-(3-((5-acetyl-2-thienyl)thio)propyl)piperidin-4-yl)-6-fluoro-1,2-benzisoxazole, 3-(1-(3-((5-acetylamino-2-thienyl)thio)propyl)piperidin-4-yl)-fluoro-1,2-benzisoxazole, 3-(1-(3-((5-acetylaminomethyl-2-thienyl)thio)propyl)piperidin-yl)-6 -fluoro-1,2-benzisoxazole, 3-(1-(4-(5-acetylaminomethyl-2-thienyl)-4-oxobutyl)piperidin-yl)-6 -fluoro-1,2-benzisoxazole, 3-(1-(4-(5-acetylaminomethyl-2-thienyl)butyl)piperidin-4-yl)-fluoro-1,2-benzisoxazole, 3-(1-(2-(5-acetylaminomethyl-2-thienyl)ethyl)piperidin-4-yl)-fluoro-1,2-benzisoxazole, 3-(1-(2-(5-acetylaminomethyl-4-methyl-2-thienyl)ethyl)-piperidin-4 -yl)-6-fluoro-1,2-benzisoxazole, 3-(1-(2-(5-acetylaminomethyl-2-methyl-3-thienyl)ethyl)-piperidin-4 -yl)-6-fluoro-1,2-benzisoxazole, 3-(1-(2-(5-(2-acetylaminoethyl)-2-thienyl)ethyl)piperidin-4-yl)-6-fluoro-1,2 -benzisoxazole, 3-(1-(2-(5-(2-acetylaminoethyl)-4-bromo-2-thienyl)ethyl)-piperidin-4 -yl)-6-fluoro-1,2-benzisoxazole, and 3-(1-(4-(5-acetylamino-2-thienyl)butyl)piperidin-4-yl)-6-fluoro-1,2-benzisoxazole, and a pharmaceutically acceptable salt thereof.

9. A pharmaceutical composition for the use as an antipsychotic or an antianxiety agent comprising a therapeutically effective amount of a compound of claim 1 or a pharmaceutically acceptable salt thereof and pharmaceutically acceptable carrier therefor.

* * * * *

UNITED STATES PATENT AND TRADEMARK OFFICE
CERTIFICATE OF CORRECTION

PATENT NO. : 5,466,691
DATED : Nov. 14, 1995
INVENTOR(S) : Nakao et al.

Page 1 of 20

It is certified that error appears in the above-identified patent and that said Letters Patent is hereby corrected as shown below:

Please delete columns 1-36 and substitute columns 1-38 as per attached.

Signed and Sealed this

Twenty-ninth Day of September, 1998

Attest:

BRUCE LEHMAN

Attesting Officer

Commissioner of Patents and Trademarks

THIOPHENE COMPOUND

TECHNICAL FIELD

This is a 371 application of PCT/JP92/01002, filed Aug. 5, 1992.

The present invention relates to novel thiophene compounds useful as pharmaceuticals and their pharmaceutically acceptable salts.

BACKGROUND ART

Up to the present, there have been developed a large number of psychotropic agents for the therapy of anxiety neurosis, schizophrenia, depression, etc. Yet, most of these drugs accompany various side-effects upon continuous administration, or the like, such as excessive sedation, addiction, dyskinesia and Parkinson disease, and they are not entirely satisfactory.

Meanwhile, Tetrahedron 44(18), 5921–5928 (1988) teaches methods for synthesizing 5-acetyl-3-cyano-2-(2-diethylaminoethyl)thio-4-phenylthiophene and 5-benzoyl-4-chloro-3-cyano-2-((2-dimethylaminoethyl)thio)thiophene. Eur. J. Med. Chem. Chim. Ther. 12(6), 557–563 (1977) teaches 2-((2-piperidinoethyl)thio)thiophene, 2-((2-morpholinoethyl)thio)thiophene, and others having an antiviral activity. Japanese Patent Unexamined Publication No. 133989/1977 discloses compounds such as 1-[2-(2-thienylthio)ethyl]-4-(N-phenyl-N-propionylamino)piperidine having a hypotensive action. Japanese Patent Unexamined Publication No. 81582/1981 discloses N-[3-[[5-(dimethylamino)methyl-4-methyl-2-thienyl]thio]propyl]-isoindole-1,3(2H)-dione as a synthetic intermediate of a compound having a histamine $H_2$ antagonistic action. Also, Chemical Abstracts 112(9): 77137p shows N-[2-(2-thienylthio)ethyl]-2-oxo-5-hydroxypyrrolidine. However, there have not been reported action of these compounds on the central nervous system.

Japanese Patent Unexamined Publication No. 115568/1985 discloses methyl (2RS, 5R)-3-[2-(5-carbamoyl-2-thienyl)ethyl]-5-phenyl-2-oxazolidinecarboxylate having an antidiabetic effect. Japanese Patent Unexamined Publication No. 213278/1989 discloses 1-[2-(2-thienyl)ethyl]-4-(2-ethyl-1,3,4-oxadiazol-5-yl)-4-(N-phenylpropionamido)piperidine having an analgesic action. Yakugaku Zasshi 104(6), 680–690 (1984) reports 3-[2-(5-acetyl-2-thienyl)ethyl]-2,4-oxazolidinedione, etc. having an antiulcer action. Furthermore, Japanese Patent Unexamined Publication Nos. 185777/1985 and 45381/1989, U.S. Pat. No. 4,032,531, Japanese Patent Unexamined Publication Nos. 151183/1977, 93334/1974 and 40582/1975, U.S. Pat. No. 3,919,243, Japanese Patent Examined Publication No. 14557/1967, U.S. Pat. No. 3,171,838, UK Patent No. 1294720, and Japanese Patent Unexamined Publication Nos. 85576/1973, 85578/1973 and 206558/1983 disclose thiophene compounds. However, these compounds have not been reported as having an action on central nervous system.

As a compound having a psychotropic action, Japanese Patent Unexamined Publication No. 156879/1977 reports 4-2-(4-acetylaminomethylphenyl)ethyl-1-phenylpiperazine.

DISCLOSURE OF THE INVENTION

The present inventors have made intensive studies with the aim of developing a psychotropic agent having less side-effects and found a novel thiophene compound exhibiting superior actions, which resulted in the completion of the invention.

That is, the present invention relates to:
1. a thiophene compound of the formula

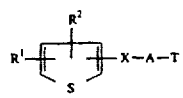

wherein;
$R^1$ and $R^2$ are the same or different, and each is a hydrogen, a halogen, a nitro, an amino, a cyano, an alkyl, a mono- or di-substituted amino, a formyl, —COOR$^3$ ($R^3$ is a hydrogen, an alkyl or an ester residue hydrolyzable in the body), an alkoxy, a hydroxyalkyl, a haloalkyl, a haloalkoxy, an alkanoyl, an aroyl, an arylalkanoyl, an alkanoyloxyalkyl, an aroyloxyalkyl, a formylamino, an alkanoylamino, an arylalkanoylamino, an aroylamino, a formylaminoalkyl, an alkanoylaminoalkyl, a haloalkanoylaminoalkyl, an arylalkanoylaminoalkyl, an aroylaminoalkyl, an arylalkyl, a carbamoyl, a mono- or di-substituted carbamoyl, a carbamoylalkyl, a mono- or di-substituted carbamoylalkyl, an aminoalkyl, a mono- or di-substituted aminoalkyl, an alkylsulfonylaminoalkyl, a hydroxyiminoalkyl or an alkoxyiminoalkyl;

X is —S(O)$_n$— (n is 0, 1 or 2), —CO—, —CH(OR$^{10}$)— ($R^{10}$ is a hydrogen, an alkyl or an acyl), —CH$_2$—, —C(=NOR$^{11}$)— ($R^{11}$ is a hydrogen, an alkyl or an acyl), or —CH(NH$_2$)—;

A is an alkylene;

T is —NHR$^4$ ($R^4$ is a heteroarylalkyl which may be hydrogenated),

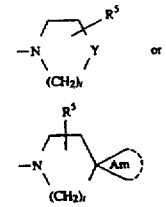

wherein t is an integer of 1–4, $R^5$ is a hydrogen, a hydroxyl group, an alkyl, an alkoxy or a carbamoyl, Y is C(R$^6$)(R$^7$) ($R^6$ is a hydrogen, a hydroxyl group, a carbamoyl, a mono- or di-substituted carbamoyl or an alkyl, and $R^7$ is a hydroxyl group, an alkyl, a cyanoalkyl, a hydroxyalkyl, an aryl, an arylalkyl, an alkoxycarbonyl, a diarylalkyl, a heteroaryl, a heteroarylalkyl, a heteroarylcarbonyl, a cycloalkyl, a cycloalkylalkyl, an alkanoyl, an aroyl, an aroylamino, an amino, a mono- or di-substituted amino or a cyclic amino, or $R^6$ and $R^7$ may form a bisarylmethylene), or N—R$^8$ ($R^8$ is an alkyl, a carbamoyl, a mono- or di-substituted carbamoyl, a cyanoalkyl, a hydroxyalkyl, an aryl, an arylalkyl, an alkoxycarbonyl, a diarylalkyl, a heteroaryl, a heteroarylalkyl, a heteroarylcarbonyl, a cycloalkyl, a cycloalkylalkyl, an alkanoyl, an aroyl or a cinnamyl), and the ring Am in the formula (2) is a 5 to 7-membered ring having an amide bond in the ring, which may further have an oxygen atom, a sulfur atom, a carbonyl and/or N—R$^9$ ($R^9$ is a hydrogen, an alkyl or an aryl), and may be condensed with a 5 to 7-membered saturated or unsaturated ring;

In the above definitions, the group having a cycloalkyl, an aryl or a heteroaryl may have 1 to 5 substituents on its ring;

provided that when X is —CO—, —CH(OR$^{10}$)— (R$^{10}$ is a hydrogen, an alkyl or an acyl), —CH$_2$—, —C(=NOR$^{11}$)— (R$^{11}$ is a hydrogen, an alkyl or an acyl) or —CH(NH$_2$)—, T is represented by the formula (1), t is 2 or 3, R$^5$ is a hydrogen, and Y is any one of the following, at least either R$^1$ or R$^2$ is a group other than a hydrogen, a halogen, a nitro, an alkoxy and an alkyl;

(i) Y is C(R$^6$)(R$^7$) (R$^6$ is a hydroxyl group and R$^7$ is an aryl or an arylalkyl)

(ii) Y is C(R$^6$)(R$^7$) (R$^6$ is a hydrogen and R$^7$ is a diarylalkyl)

(iii) Y is C(R$^6$)(R$^7$) (R$^6$ and R$^7$ form a bisarylmethylene)

(iv) Y is N—R$^8$ (R$^8$ is an alkyl, an aryl, an arylalkyl, a heteroarylalkyl, a diarylalkyl, a cycloalkylalkyl or an aroyl; or its pharmaceutically acceptable salt, 2. the thiophene compound as described in 1. above, wherein;

R$^1$ and R$^2$ are the same or different, and each is a hydrogen, a halogen, a nitro, an amino, a cyano, an alkyl, a mono- or di-substituted amino, a formyl, —COOR$^3$ (R$^3$ is a hydrogen, an alkyl or an ester residue hydrolyzable in the body), an alkoxy, a hydroxyalkyl, a haloalkyl, an alkanoyl, an aroyl, an arylalkanoyl, an alkanoylamino, an arylalkanoylamino, an aroylamino, an alkanoylaminoalkyl, a haloalkanoylaminoalkyl, an arylalkanoylaminoalkyl, an aroylaminoalkyl, an arylalkyl, a carbamoyl, a mono- or di-substituted carbamoyl, a carbamoylalkyl, a mono- or di-substituted carbamoylalkyl, an aminoalkyl, a mono- or di-substituted aminoalkyl, an alkylsulfonylaminoalkyl, a hydroxyiminoalkyl or an alkoxyiminoalkyl;

X is —S(O)$_n$— (n is 0, 1 or 2), —CO—, —CH(OR$^{10}$)— (R$^{10}$ is a hydrogen, an alkyl or an acyl), —CH$_2$—, —C(=NOR$^{11}$)— (R$^{11}$ is a hydrogen, an alkyl or an acyl), or —CH(NH$_2$)—;

A is an alkylene;

T is —NHR$^4$ (R$^4$ is a heteroarylalkyl which may be hydrogenated),

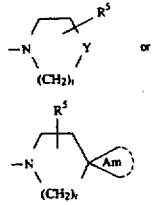

wherein t is an integer of 1–4, R$^5$ is a hydrogen or a hydroxyl group, Y is C(R$^6$)(R$^7$) (R$^6$ is a hydrogen, a hydroxyl group or a carbamoyl, and R$^7$ is an aryl, an arylalkyl, a diarylalkyl, a heteroaryl, a heteroarylalkyl, a heteroarylcarbonyl, an alkanoyl, an aroyl, an aroylamino, an amino, a mono- or di-substituted amino or a cyclic amino, or R$^6$ and R$^7$ may form a bisarylmethylene), or N—R$^8$ (R$^8$ is an alkyl, a carbamoyl, mono- or di-substituted carbamoyl, an aryl, an arylalkyl, a diarylalkyl, a heteroaryl, a heteroarylalkyl, a heteroarylcarbonyl, an alkanoyl or an aroyl), and the ring Am in the formula (2) is a 5 to 7-membered ring having an amide bond in the ring, which may further have an oxygen atom, a sulfur atom, a carbonyl and/or N—R$^9$ (R$^9$ is a hydrogen, an alkyl or an aryl), and may be condensed with a 5 to 7-membered saturated or unsaturated ring;

In the above definitions, the group having an aryl or a heteroaryl may have 1 to 5 substituents on its ring;

provided that when X is —CO—, —CH(OR$^{10}$)— (R$^{10}$ is a hydrogen, an alkyl or an acyl), —CH$_2$—, —C(=NOR$^{11}$)— (R$^{11}$ is a hydrogen, an alkyl or an acyl), or —CH(NH$_2$)—, T is represented by the formula (1), t is 2 or 3, R$^5$ is a hydrogen, and Y is any one of the following, at least either R$^1$ or R$^2$ is a group other than a hydrogen, a halogen, a nitro, an alkoxy and an alkyl;

(i) Y is C(R$^6$)(R$^7$) (R$^6$ is a hydroxyl group and R$^7$ is an aryl or an arylalkyl)

(ii) Y is C(R$^6$)(R$^7$) (R$^6$ is a hydrogen and R$^7$ is a diarylalkyl)

(iii) Y is C(R$^6$)(R$^7$) (R$^6$ and R$^7$ form a bisarylmethylene)

(iv) Y is N—R$^8$ (R$^8$ is an alkyl, an aryl, an arylalkyl, a heteroarylalkyl, a diarylalkyl or an aroyl); or its pharmaceutically acceptable salt, 3. the thiophene compound as described in 1. above, wherein;

R$^1$ and R$^2$ are the same or different, and each is a hydrogen, a halogen, a cyano, an alkyl, a formyl, a hydroxyalkyl, a haloalkyl, an alkanoyl, an aroyl, an alkanoylamino, an alkanoylaminoalkyl, a haloalkanoylaminoalkyl, an arylalkanoylaminoalkyl, an aroylaminoalkyl, a carbamoylalkyl, a mono- or di-substituted carbamoylalkyl, an aminoalkyl, a mono- or di-substituted aminoalkyl, an alkylsulfonylaminoalkyl or a hydroxyiminoalkyl;

X is —S(O)$_n$— (n is 0, 1 or 2), —CO—, —CH(OR$^{10}$)— (R$^{10}$ is a hydrogen, an alkyl or an acyl), or —CH$_2$—;

A is an alkylene;

T is

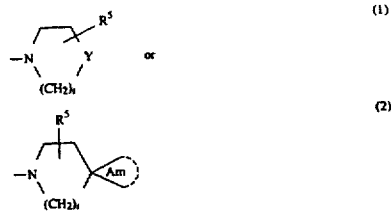

wherein t is an integer of 1–4, R$^5$ is a hydrogen or a hydroxyl group, Y is C(R$^6$)(R$^7$) (R$^6$ is a hydrogen, a hydroxyl group or a carbamoyl, and R$^7$ is an aryl, an arylalkyl, a diarylalkyl, a heteroaryl, a heteroarylalkyl, a heteroarylcarbonyl, an aroyl or a cyclic amino, or R$^6$ and R$^7$ may form a bisarylmethylene), or N—R$^8$ (R$^8$ is an alkyl, a carbamoyl, a mono- or di-substituted carbamoyl, an aryl, an arylalkyl, a diarylalkyl or a heteroaryl), and the ring Am in the formula (2) is a 5 to 7-membered ring having an amide bond in the ring, which may further have a carbonyl and/or N—R$^9$ (R$^9$ is hydrogen or an alkyl), and may be condensed with a 5 to 7-membered saturated or unsaturated ring;

In the above definitions, the group having an aryl or a heteroaryl may have 1 to 5 substituents on its ring;

provided that when X is —CO—, —CH(OR$^{10}$)— (R$^{10}$ is a hydrogen, an alkyl or an acyl), or —CH$_2$—, T is represented by the formula (1), t is 2 or 3, R$^5$ is a hydrogen, and Y is any one of the following, at least either R$^1$ or R$^2$ is a group other than a hydrogen, a halogen and an alkyl;

(i) Y is C(R$^6$)(R$^7$) (R$^6$ is a hydroxyl group and R$^7$ is an aryl or an arylalkyl)

(ii) Y is C(R$^6$ )(R$^7$) (R$^6$ is a hydrogen and R$^7$ is a diarylalkyl)

(iii) Y is C(R$^6$)(R$^7$) (R$^6$ and R$^7$ form a bisarylmethylene)

(iv) Y is N—R$^8$ (R$^8$ is an alkyl, an aryl, an arylalkyl or a diarylalkyl); or its pharmaceutically acceptable salt, 4. the thiophene compound as described in 1. above, wherein;

$R^1$ is a formyl, a hydroxyalkyl, a haloalkyl, an alkanoyl, an aroyl, an alkanoylamino, an alkanoylaminoalkyl, a haloalkanoylaminoalkyl, an arylalkanoylaminoalkyl, an aroylaminoalkyl, a carbamoylalkyl, a mono- or di-substituted carbamoylalkyl, an aminoalkyl, a mono- or di-substituted aminoalkyl, an alkylsulfonylaminoalkyl or a hydroxyiminoalkyl;

$R^2$ is a hydrogen, a halogen, a nitro, a cyano or an alkyl;

X is $-S(O)_n-$ (n is 0, 1 or 2), $-CO-$, $-CH(OR^{10})-$ ($R^{10}$ is a hydrogen, an alkyl or an acyl) or $-CH_2-$;

A is an alkylene;

T is (1)

or (2)

wherein t is an integer of 1–4, $R^5$ is a hydrogen or a hydroxyl group, Y is $C(R^6)(R^7)$ ($R^6$ is a hydrogen, a hydroxyl group or a carbamoyl, and $R^7$ is an aryl, an arylalkyl, a diarylalkyl, a heteroaryl, heteroarylalkyl, heteroarylcarbonyl, an aroyl or a cyclic amino, or $R^6$ and $R^7$ may form a bisarylmethylene), or $N-R^8$ ($R^8$ is an alkyl, a carbamoyl, a mono- or di-substituted carbamoyl, an aryl, an arylalkyl, a diarylalkyl or a heteroaryl), and the ring Am in the formula (2) is a 5 to 7-membered ring having an amide bond in the ring, which may further have a carbonyl and/or $N-R^9$ ($R^9$ is a hydrogen or an alkyl), and may be condensed with a 5 to 7-membered saturated or unsaturated ring;

In the above definitions, the group having an aryl or a heteroaryl may have 1 to 5 substituents on its ring; or its pharmaceutically acceptable salt, 5. the thiophene compound as described in 1. above which is preferably selected from 3-(4-(3-((5-acetyl-2-thienyl)thio)propyl)-1-piperazinyl)-1,2-benzisothiazole, 3-(1-(3-((5-acetyl-2-thienyl)thio)propyl)piperidin-4-yl)-6-fluoro-1,2-benzisoxazole, 3-(1-(3-((5-acetylamino-2-thienyl)thio)propyl)piperidin-4yl)-6-fluoro-1,2-benzisoxazole, 3-(1-(3-((5-acetylaminomethyl-2thienyl)thio)propyl)piperidin-4-yl)-6-fluoro-1,2-benzisoxazole, 3-(1-(4-(5-acetylaminomethyl-2-thienyl)-4-oxobutyl)piperidin-4-yl)-6-fluoro-1,2-benzisoxazole, 3-(1-(4-(5-acetylaminomethyl-2-thienyl)butyl)piperidin-4-yl)-6-fluoro-1,2-benzisoxazole, 3-(1-(2-(5-acetylaminomethyl-2-thienyl)ethyl)piperidin-4-yl)-6-fluoro-1,2-benzisoxazole, 3-(1-(2-(5-acetylaminomethyl-4-methyl-2-thienyl)ethyl)piperidin-4-yl)-6-fluoro-1,2-benzisoxazole, 3-(1-(2-(5-acetylaminomethyl-2-methyl-3-thienyl)ethyl)piperidin-4-yl)-6-fluoro-1,2-benzisoxazole, 3-(1-(2-(5-(2-acetylaminoethyl)-2-thienyl)ethyl)piperidin-4-yl)-6-fluoro-1,2-benzisoxazole, 3-(1-(2-(5-(2-acetylaminoethyl)-4-bromo-2-thienyl)ethyl)piperidin-4-yl)-6-fluoro-1,2-benzisoxazole, 3-(1-(4-(5-acetylamino-2-thienyl)butyl)piperidin-4-yl)-6-fluoro-1,2-benzisoxazole, and their pharmaceutically acceptable salts, 6. a pharmaceutical composition containing the compound as described in 1. above and additives for pharmaceuticals.

7. an antipsychotic containing, as an active ingredient, the compound as described in 1. above, 8. a thiophene compound of the formula wherein;

$R^1$ and $R^2$ are the same or different, and each is a hydrogen, a halogen, a nitro, an amino, an alkyl, a mono- or di-substituted amino, a formyl, $-COOR^3$ ($R^3$ is a hydrogen, an alkyl or an ester residue hydrolyzable in the body), an alkoxy, a hydroxyalkyl, a haloalkyl, a haloalkoxy, an alkanoyl, an aroyl, an arylalkanoyl, an alkanoyloxyalkyl, an aroyloxyalkyl, a formylamino, an alkanoylamino, an arylalkanoylamino, an aroylamino, an aralkyl, a carbamoyl, a mono- or di-substituted carbamoyl, a hydroxyiminoalkyl, an alkoxyiminoalkyl, an aminoalkyl or a mono- or di-substituted aminoalkyl;

n is 0, 1 or 2;

A is an alkylene;

T is $-NHR^4$ ($R^4$ is a heteroarylalkyl which may be hydrogenated), (1)

or (2)

wherein t is an integer of 1–4, $R^5$ is a hydrogen, a hydroxyl group, an alkyl, an alkoxy or a carbamoyl, Y is $C(R^6)(R^7)$ ($R^6$ is a hydrogen, a hydroxyl group, a carbamoyl, a mono- or di-substituted carbamoyl or an alkyl, and $R^7$ is a hydroxyl group, an alkyl, a cyanoalkyl, a hydroxyalkyl, an aryl, an arylalkyl, an alkoxycarbonyl, a diarylalkyl, a heteroaryl, a heteroarylalkyl, a heteroarylcarbonyl, a cycloalkyl, a cycloalkylalkyl, an alkanoyl, an aroyl, an aroylamino, an amino, a mono- or di-substituted amino or a cyclic amino, or $R^6$ and $R^7$ may form a bisarylmethylene), or $N-R^8$ ($R^8$ is alkyl, a cyanoalkyl, a hydroxyalkyl, an aryl, an arylalkyl, an alkoxycarbonyl, a diarylalkyl, a heteroaryl, a heteroarylalkyl, a heteroarylcarbonyl, a cycloalkyl, a cycloalkylalkyl, an alkanoyl, an aroyl or a cinnamyl), and the ring Am in the formula (2) is a 5 to 7-membered ring having an amide bond in the ring, which may further have an oxygen atom, a sulfur atom, a carbonyl and/or $N-R^9$ ($R^9$ is a hydrogen, an alkyl or an aryl), and may be condensed with a 5 to 7-membered saturated or unsaturated ring;

In the above definitions, the group having an aryl or a heteroaryl may have 1 to 5 substituents on its ring; or its pharmaceutically acceptable salt, and 9. a thiophene compound of the formula wherein:

$R^1$ and $R^2$ are the same or different, and each is a hydrogen, a halogen, a nitro, an amino, an alkyl, a mono- or di-substituted amino, a formyl, —COOR$^3$ ($R^3$ is a hydrogen, an alkyl or an ester residue hydrolyzable in the body), an alkoxy, a hydroxyalkyl, a haloalkyl, a haloalkoxy, an alkanoyl, an aroyl, an arylalkanoyl, an alkanoyloxyalkyl, an aroyloxyalkyl, a formylamino, an alkanoylamino, an arylalkanoylamino, an aroylamino, a formylaminoalkyl, an alkanoylaminoalkyl, a haloalkanoylaminoalkyl, an arylalkanoylaminoalkyl, an aroylaminoalkyl, an arylalkyl, a carbamoyl, a mono- or di-substituted carbamoyl, a carbamoylalkyl, a mono- or di-substituted carbamoylalkyl, an aminoalkyl, a mono- or di-substituted aminoalkyl or an alkylsulfonylaminoalkyl;

X is —CO—, —CH(OR$^{10}$)— ($R^{10}$ is a hydrogen, an alkyl or an acyl), —CH$_2$—, —C(=NOR$^{11}$ ($R^{11}$ is a hydrogen, an alkyl or an acyl), or —CH(NH$_2$)—;

A is an alkylene;

T is —NHR$^4$ ($R^4$ is a heteroarylalkyl which may be hydrogenated),

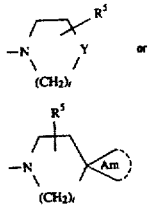

wherein t is an integer of 1–4, $R^5$ is a hydrogen, a hydroxyl group, an alkyl, an alkoxy or a carbamoyl, Y is C(R$^6$)(R$^7$) ($R^6$ is a hydrogen, a hydroxyl group, a carbamoyl, a mono- or di-substituted carbamoyl or an alkyl, and $R^7$ is a hydroxyl group, an alkyl, a cyanoalkyl, a hydroxyalkyl, an aryl, an arylalkyl, an alkoxycarbonyl, diarylalkyl, a heteroaryl, a heteroarylalkyl, a heteroarylcarbonyl, a cycloalkyl, a cycloalkylalkyl, an alkanoyl, an aroyl, an aroylamino, an amino, a mono- or di-substituted amino or a cyclic amino, or $R^6$ and $R^7$ may form a bisarylmethylene), or N—R$^8$ ($R^8$ is an alkyl, a cyanoalkyl, a hydroxyalkyl, an aryl, an arylalkyl, an alkoxycarbonyl, diarylalkyl, a heteroaryl, a heteroarylalkyl, a heteroarylcarbonyl, a cycloalkyl, a cycloalkylalkyl, an alkanoyl, an aroyl or a cinnamyl), and the ring Am in the formula (2) is a 5 to 7-membered ring having an amide bond in the ring, which may further have an oxygen atom, a sulfur atom, a carbonyl and/or N-R$^9$ ($R^9$ is a hydrogen, an alkyl or an aryl) and may be condensed with a 5 to 7-membered saturated or unsaturated ring;

In the above definitions, the group having an aryl or a heteroaryl may have 1 to 5 substituents on its ring; provided that when T is represented by the formula (1), t is 2 or 3, $R^5$ is a hydrogen, and Y is any one of the following, at least either $R^1$ or $R^2$ is a group other than a hydrogen, a halogen, a nitro, an alkoxy and an alkyl:

(i) Y is C(R$^6$)(R$^7$) ($R^6$ is a hydroxyl group and $R^7$ is an aryl or an arylalkyl)

(ii) Y is C(R$^6$)(R$^7$) ($R^6$ is a hydrogen and $R^7$ is a diarylalkyl)

(iii) Y is C(R$^6$)(R$^7$) ($R^6$ and $R^7$ form a bisarylmethylene)

(iv) Y is N—R$^8$ ($R^8$ is an alkyl, an aryl, an arylalkyl, a heteroarylalkyl, a diarylalkyl, a cycloalkylalkyl or an aroyl); or its pharmaceutically acceptable salt.

In the above formula (I), the halogen at $R^1$ or $R^2$ is chlorine, bromine, iodine or fluorine.

The alkyl at $R^1$, $R^2$, $R^3$, $R^5$, $R^6$, $R^7$, $R^8$, $R^9$, $R^{10}$ or $R^{11}$ is a straight or branched-chain alkyl having 1 to 8 carbon atoms, and is exemplified by methyl, ethyl, propyl, isopropyl, butyl, isobutyl, tert-butyl, pentyl, isopentyl, hexyl, heptyl or octyl, with preference given to an alkyl having 1 to 4 carbon atoms.

The mono- or di-substituted amino at $R^1$, $R^2$ or $R^7$ is an amino mono- or di-substituted by alkyl(s) having 1 to 4 carbon atoms, and is exemplified by methylamino, dimethylamino, ethylamino, diethylamino, propylamino, dipropylamino or isopropylamino.

The alkoxy at $R^1$, $R^2$ or $R^5$ is a straight or branched-chain alkoxy having 1 to 8 carbon atoms such as methoxy, ethoxy, propoxy, isopropoxy, butoxy, isobutoxy, tert-butoxy, pentyloxy, hexyloxy, heptyloxy or octyloxy, with preference given to an alkoxy having 1 to 4 carbon atoms.

The hydroxyalkyl at $R^1$ or $R^2$ has 1 to 4 carbon atoms and is exemplified by hydroxymethyl, 1-hydroxyethyl, 1-hydroxypropyl or 1-hydroxybutyl; the haloalkyl at $R^1$ or $R^2$ has 1 to 4 carbon atoms and is exemplified by chloromethyl, bromomethyl, fluoromethyl, dichloromethyl, difluoromethyl, trifluoromethyl, chloroethyl, 2,2,3,3-tetrafluoropropyl or 2,2,2-trifluoroethyl; and the haloalkoxy at $R^1$ or $R^2$ has 1 to 4 carbon atoms and is exemplified by chloromethoxy, bromomethoxy, fluoromethoxy, dichloromethoxy, difluoromethoxy, trifluoromethoxy, chloroethoxy, 2,2,3,3-tetrafluoropropoxy or 2,2,2-trifluoroethoxy.

The alkanoyl at $R^1$, $R^2$, $R^7$ or $R^8$ is an alkanoyl having 2 to 5 carbon atoms such as acetyl, propionyl, butyryl or pivaloyl; and the aroyl at $R^1$, $R^2$, $R^7$ or $R^8$ is exemplified by benzoyl or naphthoyl.

The alkanoyl moiety of the arylalkanoyl at $R^1$ or $R^2$ is an alkanoyl having 2 to 5 carbon atoms, and the arylalkanoyl is exemplified by phenylacetyl, phenylpropionyl or phenylbutyryl; the alkanoyl moiety of the alkanoyloxyalkyl at $R^1$ or $R^2$ is an alkanoyl having 1 to 5 carbon atoms and the alkyl moiety thereof is an alkyl having 1 to 4 carbon atoms, and the alkanoyloxyalkyl is exemplified by 1-formyloxypropyl, acetoxymethyl, propionyloxymethyl, 1- or 2-acetoxyethyl, 1- or 2-propionyloxyethyl, 1- or 3-acetoxypropyl or 1- or 3-propionyloxypropyl; the alkyl moiety of the aroyloxyalkyl at $R^1$ or $R^2$ is an alkyl having 1 to 4 carbon atoms, and the aroyloxyalkyl is exemplified by benzoyloxymethyl, benzoyloxyethyl, benzoyloxypropyl or benzoyloxybutyl; the alkanoyl moiety of the alkanoylamino at $R^1$ or $R^2$ is an alkanoyl having 2 to 5 carbon atoms, and the alkanoylamino is exemplified by acetylamino, propionylamino or butyrylamino; and the alkanoyl moiety of the arylalkanoylamino at $R^1$ or $R^2$ is an alkanoyl having 2 to 5 carbon atoms, and the arylalkanoylamino is exemplified by phenylacetylamino, phenylpropionylamino or phenylbutyrylamino.

The aroylamino at $R^1$, $R^2$ or $R^7$ is exemplified by benzoylamino or naphthoylamino.

The alkyl moiety of the formylaminoalkyl at $R^1$ or $R^2$ is an alkyl having 1 to 4 carbon atoms, and the formylaminoalkyl is exemplified by formylaminomethyl or formylaminoethyl; the alkanoyl moiety of the alkanoylaminoalkyl at $R^1$ or $R^2$ is an alkanoyl having 2 to 5 carbon atoms and the alkyl moiety thereof is an alkyl having 1 to 4 carbon atoms, and the alkanoylaminoalkyl is exemplified by acetylaminomethyl, acetylaminoethyl or propionylaminomethyl; the alkanoyl moiety of the haloalkanoylaminoalkyl at $R^1$ or $R^2$ is an alkanoyl having 2 to 5 carbon atoms and the alkyl moiety thereof is an alkyl having 1 to 4 carbon atoms, and the haloalkanoylaminoalkyl is exemplified by trifluoroacetylaminomethyl or trifluoroacetylaminoethyl; the alkanoyl moiety of the arylalkanoylaminoalkyl at $R^1$ or $R^2$ is an alkanoyl having 2 to 5 carbon atoms and the alkyl moiety thereof is an alkyl having 1 to 4 carbon atoms, and the arylalkanoylaminoalkyl is exemplified by phenylacetylaminomethyl; and the alkyl moiety of the aroylaminoalkyl at $R^1$ or $R^2$ is an alkyl having 1 to 4 carbon atoms, and the aroylaminoalkyl is exemplified by benzoylaminomethyl.

The alkyl moiety of the arylalkyl at $R^1$, $R^2$, $R^7$ or $R^8$ is an alkyl having 1 to 6 carbon atoms, and the arylalkyl is exemplified by benzyl, phenylethyl, phenylpropyl or diphenylmethyl.

The mono- or di-substituted carbamoyl at $R^1$, $R^2$, $R^6$ or $R^8$ is a carbamoyl mono- or di-substituted by an alkyl having 1 to 4 carbon atoms, cyclohexyl, phenyl or benzyl, such as methylcarbamoyl, ethylcarbamoyl, propylcarbamoyl, dimethylcarbamoyl, diethylcarbamoyl, dipropylcarbamoyl, cyclohexylcarbamoyl, phenylcarbamoyl or benzylcarbamoyl.

The alkyl moiety of the carbamoylalkyl at $R^1$ or $R^2$ is an alkyl having 1 to 4 carbon atoms, and the carbamoylalkyl is exemplified by carbamoylmethyl or 2-carbamoylethyl; the mono- or di-substituted carbamoyl of the mono- or di-substituted carbamoylalkyl at $R^1$ or $R^2$ is a carbamoyl mono- or di-substituted by an alkyl having 1 to 4 carbon atoms or benzyl, and the alkyl moiety thereof is an alkyl having 1 to 4 carbon atoms, and the mono- or di-substituted carbamoylalkyl is exemplified by methylcarbamoylmethyl; the alkyl moiety of the aminoalkyl at $R^1$ or $R^2$ is an alkyl having 1 to 4 carbon atoms, and the aminoalkyl is exemplified by aminomethyl, aminoethyl or aminopropyl; the mono- or di-substituted amino of the mono- or di-substituted aminoalkyl at $R^1$ or $R^2$ is an amino mono- or di-substituted by alkyl(s) having 1 to 4 carbon atoms, and the alkyl moiety thereof is an alkyl having 1 to 4 carbon atoms, and the mono- or di-substituted aminoalkyl is exemplified by methylaminomethyl, dimethylaminomethyl, methylaminoethyl, dimethylaminoethyl, ethylaminomethyl, diethylaminomethyl, propylaminomethyl, methylaminopropyl or dimethylaminopropyl; the alkyl moieties of the alkylsulfonylaminoalkyl at $R^1$ or $R^2$ are respectively an alkyl having 1 to 4 carbon atoms, and the alkylsulfonylaminoalkyl is exemplified by methanesulfonylaminomethyl or methanesulfonylaminoethyl; the alkyl moiety of the hydroxyiminoalkyl at $R^1$ or $R^2$ is an alkyl having 1 to 4 carbon atoms, and the hydroxyiminoalkyl is exemplified by 1-hydroxyiminoethyl, 1-hydroxyiminopropyl or 1-hydroxyiminobutyl; the alkoxy moiety and the alkyl moiety of the alkoxyiminoalkyl at $R^1$ or $R^2$ are respectively alkoxy and alkyl each having 1 to 4 carbon atoms, and the alkoxyiminoalkyl is exemplified by 1-methoxyiminoethyl, 1-ethoxyiminoethyl, 1-methoxyiminopropyl or 1-isopropoxyiminoethyl.

The ester residue at $R^3$ which is hydrolyzable in the body is the one easily decomposed in the body into a free carboxylic acid or its salt, and is exemplified by an alkanoyloxyalkyl ester such as acetoxymethyl, pivaloyloxymethyl, 1-acetoxyethyl or 1-pivaloyloxyethyl; an alkoxycarbonyloxyalkyl ester such as ethoxycarbonyloxymethyl or 1-ethoxycarbonyloxyethyl; ester such as phthalidyl or dimethoxyphthalidyl; carbamoylalkyl ester such as carbamoylmethyl, carbamoylethyl, N-methylcarbamoylmethyl, N,N-dimethylcarbamoylmethyl or N,N-diethylcarbamoylmethyl; alkoxyalkyl ester such as methoxymethyl or methoxyethyl; or 5-methyl-1,3-dioxolen-2-on-4-ylmethyl ester.

The alkylene at A is a straight or branched-chain alkylene having 1 to 10 carbon atoms, such as methylene, ethylene, trimethylene, tetramethylene, pentamethylene, hexamethylene, octamethylene, decamethylene, propylene, 1,1-dimethylethylene or 2,2-dimethyltrimethylene, with preference given to an alkylene having 1 to 6 carbon atoms.

The alkyl moiety of the heteroarylalkyl at $R^4$ which may be hydrogenated is an alkyl having 1 to 4 carbon atoms, and the heteroarylalkyl is exemplified by pyridylmethyl, furylmethyl, thienylmethyl or (1,4-benzodioxan-2-yl)methyl.

The aryl at $R^7$, $R^8$ or $R^9$ is phenyl, naphthyl, or the like.

The alkyl moiety of the cyanoalkyl at $R^7$ or $R^8$ is an alkyl having 1 to 4 carbon atoms, and the cyanoalkyl is exemplified by cyanomethyl, 2-cyanoethyl, 3-cyanopropyl or 4-cyanobutyl; the alkyl moiety of the hydroxyalkyl at $R^7$ or $R^8$ is an alkyl having 1 to 4 carbon atoms, and the hydroxyalkyl is exemplified by hydroxymethyl, 2-hydroxyethyl, 3-hydroxypropyl or 4-hydroxybutyl; the alkoxy moiety of the alkoxycarbonyl at $R^7$ or $R^8$ is an alkoxy having 1 to 4 carbon atoms, and the alkoxycarbonyl is exemplified by methoxycarbonyl, ethoxycarbonyl, propoxycarbonyl, isopropoxycarbonyl, butoxycarbonyl, isobutoxycarbonyl or tert-butoxycarbonyl; the alkyl moiety of the diarylalkyl at $R^7$ or $R^8$ is an alkyl having 1 to 4 carbon atoms, and the diarylalkyl is exemplified by diphenylmethyl or 2,2-diphenylethyl; examples of the heteroaryl at $R^7$ or $R^8$ include pyridyl, thienyl, furyl, pyrimidinyl, thiazolyl, oxazolyl, indolyl, benzothiazolyl, benzimidazolyl, 1,2-benzisothiazolyl, 1,2-benzisoxazolyl, benzothiophen-2- or 3-yl, benzofuran-2 or 3-yl, quinolyl, isoquinolyl, benzoxazolyl, pyrazinyl, pyridazinyl, imidazolyl, thieno[3,2-c]pyridin-4-yl, furo[3,2-c]pyridin-4-yl, 7,8-dihydro-5H-thiopyrano[4,3-b]pyridin-2-yl, 1,2-benzisothiazolyl-S,S-dioxide, 2-oxo-1-benzimidazolyl, 2-thioxo-1-benzimidazolyl, 2,4-dioxohexahydropyrimidin-1-yl and hydantoin-1-yl; the heteroarylalkyl at $R^7$ or $R^8$ may be hydrogenated, and the alkyl moiety thereof is an alkyl having 1 to 4 carbon atoms, and the heteroarylalkyl is exemplified by pyridylmethyl, furylmethyl, thienylmethyl, pyrrolylmethyl, oxazolylmethyl, thiazolylmethyl or (1,2-benzodioxan-2-yl)methyl; the heteroarylcarbonyl at $R^7$ or $R^8$ may be nicotinoyl, isonicotinoyl, thenoyl, furoyl, pyrrolylcarbonyl, oxazolylcarbonyl or thiazolylcarbonyl; the cycloalkyl at $R^7$ or $R^8$ is a cycloalkyl having 3 to 8 carbon atoms such as cyclopropyl, cyclobutyl, cyclopentyl, cyclohexyl or cycloheptyl; and the cycloalkyl moiety of the cycloalkylalkyl at $R^7$ or $R^8$ is a cycloalkyl having 3 to 8 carbon atoms and the alkyl moiety thereof is an alkyl having 1 to 4 carbon atoms, and the cycloalkylalkyl is exemplified by cyclopropylmethyl, cyclobutylmethyl, cyclohexylmethyl or cycloheptylmethyl.

The cyclic amino at $R^7$ includes, for example, pyrrolidinyl, piperidino, hexamethyleneimino, morpholino, thiomorpholino, piperazinyl, homopiperazinyl, 4-substituted piperazinyl and 4-substituted homopiperazinyl (substituent is exemplified by alkyl having 1 to 4 carbon atoms, aryl, benzyl, alkanoyl having 2 to 5 carbon atoms or benzoyl).

The bisarylmethylene formed by $R^6$ and $R^7$ is, for example, diphenylmethylene, bis(4-fluorophenyl)methylene or bis(4-chlorophenyl)methylene.

The acyl at $R^{10}$ or $R^{11}$ is, for example, alkanoyl having 2 to 5 carbon atoms such as acetyl, propionyl or butyryl, or benzoyl.

The 5- to 7-membered ring Am having an amide bond in the formula (2) is, for example, thiazolidinone, imidazolidinone, pyrazolidinone or pyrrolidinone, and the ring Am may further have oxygen atom, sulfur atom, carbonyl and/or N—$R^9$ ($R^9$ is hydrogen, alkyl or aryl) in the ring. The ring Am may be condensed with a 5- to 7-membered saturated or unsaturated ring, which is exemplified by 2-oxo-1,2,3,5,6,7,8,8a-octahydroimidazo[1,2-a]pyridine-3-spiro-4'-piperidino or 2-oxo-2,3,5,6,7,8-hexahydroimidazo[1,2-a]pyridine-3-spiro-4'-piperidino.

In the above definitions, the group including cycloalkyl, aryl, benzyl, benzoyl or heteroaryl may have 1 to 5, preferably 1 to 3 substituents, which substituents being exemplified by halogen, nitro, amino, cyano, haloalkyl having 1 to 4 carbon atoms, hydroxyl group, alkyl having 1 to 4 carbon atoms, alkoxy having 1 to 4 carbon atoms, alkenyl having 2 to 4 carbon atoms, and phenyl.

In the above formula (I), $R^1$ is preferably acetyl, acetylamino, acetylaminomethyl, 2-acetylaminoethyl, methyl, aminomethyl, benzoylamino, propionylaminomethyl, or the like, and $R^2$ is particularly preferably hydrogen, halogen, methyl, or the like. Preferable X includes, for example, —S—, —SO—, —SO$_2$—, —CO—, —CH$_2$— and —CH(OH)—, and A is preferably methylene, ethylene, trimethylene, tetramethylene, pentamethylene, hexamethylene, 2-methyltrimethylene, or the like. T is preferably 1-piperazinyl substituted at the 4-position by, for example, 2-pyrimidinyl, 3-trifluorophenyl, 2-methoxyphenyl, 2,3-dimethylphenyl, 1,2-benzisothiazol-3-yl, methyl, 3-chlorophenyl, bis(4-chlorophenyl)methyl, 3-trifluoromethyl, 6-pyridyl, 1,2-benzisoxazol-3-yl, cyclohexylcarbamoyl or phenylcarbamoyl; pyperidino substituted at the 4-position by, for example, 4-fluorobenzoyl, 6-fluoro-1,2-benzisoxazol-3-yl or 1,2-benzisothiazol-3-yl; or the like, and particularly preferred are, for example, 4-(1,2-benzisothiazol-3-yl)-1-piperadinyl and 4-(6-fluoro-1,2-benzisoxazol-3-yl)piperidino.

Examples of the pharmaceutically acceptable salt of the compound of the formula (I) include salts with inorganic acids such as hydrochloric acid, hydrobromic acid, sulfuric acid, phosphoric acid and nitric acid, and salts with organic acids such as acetic acid, succinic acid, glycolic acid, lactic acid, malic acid, tartaric acid, citric acid, ascorbic acid, maleic acid, fumaric acid, methanesulfonic acid and benzenesulfonic acid. In the case where the compound has carboxyl group, the salt may be a metal salt such as sodium, potassium or calcium salt, an amine salt with methylamine, diethylamine, triethylamine, or the like, or a salt with an amino acid such as lysine, ornithine or arginine. In addition, hydrates (e.g. ½ hydrate, monohydrate, ¾ hydrate) and other solvates are also encompassed.

Where the compound of the present invention has an asymmetric carbon, racemates and optical isomers are encompassed, and where the compound has an oxime, syn- and anti-isomers are encompassed in the present invention.

The thiophene compound of the invention can be produced by the following methods.

Method 1

The compound of the formula (I) can be produced by reacting a compound of the formula

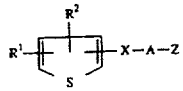

(II)

wherein Z is a hydroxyl group or a reactive atom or group derived from hydroxyl group, such as halogen, methanesulfonyloxy or p-toluenesulfonyloxy, and other symbols are as defined above, with a compound of the formula

H—T (III)

wherein each symbol is as defined above.

When Z in the compound of the formula (II) is a reactive atom or group derived from hydroxyl group, the reaction with the compound of the formula (III) may be carried out in a suitable solvent which does not interfere with the reaction, such as methanol, ethanol, propanol, benzene, toluene, dimethylformamide, tetrahydrofuran, acetonitrile or acetone, in the presence of a suitable acid scavenger such as potassium carbonate, sodium carbonate, sodium hydrogencarbonate, potassium hydroxide, pyridine, triethylamine, sodium acetate or potassium acetate at a temperature between 20° C. and 150° C. for 30 minutes to 30 hours.

When Z in the compound of the formula (II) is a hydroxyl group, the reaction may be carried out in a suitable solvent which does not adversely affect the reaction, such as dimethylformamide or benzene in the presence of an aminophosphonium reagent such as N,N-methylphenylaminotriphenylphosphonium or iodide at a temperature between 20° C. and 150° C. for 30 minutes to 5 hours.

Method 2

Of the compounds of the formula (I), a compound wherein X is —S(O)$_n$— (n is 1 or 2) can be produced by subjecting a compound wherein n is 0 to an oxidation.

The oxidation can be usually carried out in a suitable solvent with the use of an oxidizing agent such as m-chloroperbenzoic acid, peracetic acid, sodium bromite or hydrogen peroxide. As the reaction solvent, usable are, for example, chloroform, tetrahydrofuran, dioxane, and water, and the reaction temperature is between 0° C. and a temperature near the boiling point of the solvent used, preferably between 0° C. and 30° C.

Method 3

Of the compounds of the formula (I), a compound wherein $R^1$ or $R^2$ is $R^{12}$—CONH— ($R^{12}$ is hydrogen, alkyl, aralkyl or aryl), or $R^{12}$—NHCO— ($R^{12}$ is as defined above) can be produced by converting a compound of the formula

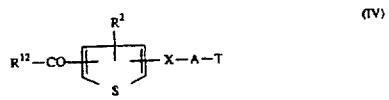

(IV)

wherein each symbol is as defined above, to an oxime compound, and subjecting the oxime compound to Beckmann rearrangement.

The conversion to an oxime compound is conducted by using hydroxylamine hydrochloride in a solvent such as water or ethanol in the presence of a base such as sodium hydroxide, potassium hydroxide, sodium hydrogencarbonate or potassium hydrogencarbonate at a temperature between 0° C. and a temperature near the boiling point of the solvent used, preferably between 80° C. and 100° C. The oxime compound thus obtained is heated to 70° C. to 120° C. in polyphosphoric acid or sulfuric acid to conduct Beckmann rearrangement.

Method 4

Of the compounds of the formula (I), a compound wherein $R^1$ or $R^2$ is aminoalkyl can be produced by reducing the oxime compound obtained in Method 3.

The reduction can be carried out by using a chemical reducing agent such as lithium aluminium hydride or sodium borohydride, in a solvent such as tetrahydrofuran or an ether at a temperature between 50° C. and 100° C.

Method 5

The compound of the formula (IV) can be produced by reacting a compound of the formula

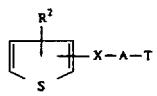  (V)

wherein each symbol is as defined above, with a carboxylic acid of the formula $R^{12}COOH$ (VI)

wherein $R^{12}$ is as defined above, or its reactive derivative such as acid halide, acid anhydride, mixed acid anhydride, active ester, or the like.

When the compound of the formula (VI) is a free carboxylic acid, the reaction is carried out in the presence of a dehydrating agent such as polyphosphoric acid at room temperature to 150° C.

When an acid halide such as chloride, bromide, iodide, etc. is used as the reactive derivative of the formula (VI), the reaction is carried out in a suitable solvent which does not adversely affect the reaction, such as benzene, toluene, chloroform, methylene chloride or dichloroethane, in the presence of a Lewis acid such as aluminium chloride, tin chloride or iron chloride at −10° C. to 100° C. for 5 minutes to 20 hours.

Method 6

A compound of the formula

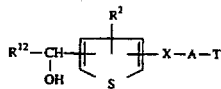  (VII)

wherein each symbol is as defined above, can be obtained by chemical reduction of the compound of the formula (IV) using, for example, sodium borohydride, lithium aluminium hydride or triethylsilane in a suitable solvent which does not adversely affect the reaction, such as methanol, ethanol, propanol, butanol or acetic acid by chemical reduction, or by catalytic reduction in the presence of a suitable catalyst such as palladium, rhodium or platinum at −10° C. to 150° C. for 5 minutes to 20 hours.

Method 7

A compound of the formula

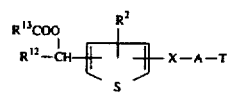  (IX)

wherein each symbol is as defined above, can be obtained by reacting the compound of the formula (VII) with a carboxylic acid of the formula $R^{11}COOH$ (VIII)

wherein $R^{13}$ is hydrogen, alkyl, aryl, aralkyl or heteroaryl, or its acid anhydride.

The reaction proceeds in a suitable solvent which does not adversely affect the reaction, such as benzene or toluene, or without solvent at room temperature to 150° C. The instant reaction also proceeds in the presence of a base such as triethylamine.

Method 8

Of the compounds of the formula (I), a compound wherein X is —CH(OH)— or —CH$_2$— can be obtained by reducing a compound wherein X is —CO— with the use of a suitable reducing agent such as sodium borohydride.

The reaction proceeds in a suitable solvent which does not adversely affect the reaction, such as methanol, ethanol, propanol, isopropyl alcohol, tetrahydrofuran, dichloromethane or dichloroethane in the presence of a suitable reducing agent such as lithium aluminium hydride, sodium borohydride, sodium cyanoborohydride, trifluoroborodiethylate or triethylsilane at −10° C. to 100° C. for 30 minutes to 10 hours.

Method 9

Of the compounds of the formula (I), a compound wherein $R^1$ or $R^2$ is $R^{14}$—CONH—B— ($R^{14}$ is hydrogen, alkyl, haloalkyl, aralkyl or aryl, and B is a single bond or alkylene) can be obtained by reacting a compound of the formula

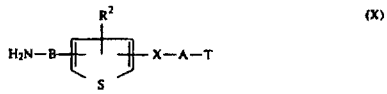  (X)

wherein each symbol is as defined above, with a carboxylic acid of the formula $R^{14}COOH$ (XI)

wherein $R^{14}$ is as defined above, or its reactive derivative such as acid halide or acid anhydride.

The reaction proceeds in a suitable solvent which does not adversely affect the reaction such as dichloromethane, dichloroethane or chloroform in the presence of a suitable acid scavenger such as triethylamine, methylmorpholine or pyridine at 0° C. to 100° C.

Method 10

Of the compounds of the formula (I), a compound wherein $R^1$ or $R^2$ is $R^{15}$—SO$_2$NH—B— ($R^{15}$ is alkyl or aryl, and B is a single bond or alkylene) can be obtained by reacting a compound of the formula (X) and a sulfonic acid of the formula $R^{15}$—SO$_3$H (XII)

wherein $R^{15}$ is as defined above, or its reactive derivative (acid halide).

The reaction proceeds in a suitable solvent which does not adversely affect the reaction such as dichloromethane, dichloroethane or chloroform in the presence of a suitable acid scavenger such as triethylamine, methylmorpholine or pyridine at 0° C. to 100° C.

Method 11

Of the compounds of the formula (I), a compound wherein $R^1$ or $R^2$ is aminoalkyl can be obtained by hydrolyzing a compound of the formula

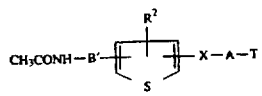  (XIII)

wherein B' is alkylene, and other symbols are as defined above.

Method 12

Of the compounds of the formula (I), a compound wherein X is —CH(OR$^{10'}$)— (R$^{10'}$ is alkyl or acyl) can be produced by reacting a compound of the formula (I) wherein X is —CH(OH)— and a compound of the formula

    (XIV)

wherein Z$^1$ is halogen, and R$^{10'}$ is as defined above.

The reaction proceeds in a suitable solvent which does not adversely affect the reaction, such as methanol, ethanol, propanol, butanol, N,N-dimethylformamide, tetrahydrofuran, benzene or toluene in the presence of a suitable acid scavenger such as sodium hydride, sodium amide, sodium methoxide, sodium ethoxide, potassium hydroxide or sodium hydroxide at room temperature to 150° C. for an hour to 20 hours.

Method 13

Of the compounds of the formula (I), a compound wherein X is —C(=NOH)— can be produced by reacting a compound of the formula (I) wherein X is —CO— with hydroxylamine.

The reaction is carried out by allowing hydroxylamine or its salt such as hydrochloride, hydrobromide or sulfate to react in a suitable solvent which is subject to no limitation so long as it does not adversely affect the reaction, and is preferably exemplified by alcohols such as methanol, ethanol, propanol, isopropyl alcohol or butanol, in the presence or absence of an acid scavenger such as an organic base (e.g. triethylamine, pyridine, N,N-dimethylaniline) or inorganic base (e.g. sodium carbonate, potassium carbonate, sodium hydrogencarbonate). The reaction temperature and reaction time are not particularly limited, and the reaction is normally conducted at room temperature to a temperature near the boiling point of the solvent used for several to several dozens of hours.

Method 14

Of the compounds of the formula (I), a compound wherein X is —C(=NOR$^{11'}$)—(R$^{11'}$ is alkyl or acyl) can be produced by reacting a compound of the formula (I) wherein X is —C(=NOH)— with a compound of the formula R$^{11'}$—Z$^1$+tm  (XV)

wherein Z' is halogen, and R$^{11'}$ is as defined above, in the same manner as in Method 12.

Method 15

Of the compounds of the formula (I), a compound wherein X is —CH(NH$_2$)— can be produced by subjecting a compound of the formula (I) wherein X is —C(=NOH)— to a reduction using a suitable reducing agent.

The reduction is carried out using a suitable catalyst such as palladium carbon, Raney-nickel, platinum or rhodium in a suitable solvent which is subject to no limitation so long as it does not adversely affect the reaction, such as alcohols (e.g. methanol, ethanol, propanol or isopropyl alcohol), or acids (e.g. formic acid, acetic acid) by a catalytic hydrogenation under atmospheric pressure or pressurization.

The reaction temperature and reaction time are not particularly limited, and the reaction is usually conducted at room temperature to about 150° C. for several to several dozens of hours, or using a suitable reducing agent such as lithium aluminium hydride or tri-tert-butoxyaluminium hydride in a suitable solvent which is subject to no limitation as long as it does not adversely affect the reaction, but preferably ethers such as diethylether, tetrahydrofuran, dioxane and dimethylcellusolve, under cooling, at room temperature, or under heating for several to several dozens of hours.

Of the starting materials represented by the formula (II) in Method 1, the compound wherein X is —S(O)$_n$— (n=0) can be produced by the following reaction.

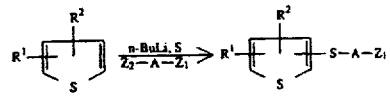

This reaction is carried out by lithiation by a conventional method using butyl lithium in a nonaqueous solvent such as ether, tetrahydrofuran, dioxane, benzene, toluene or a mixed solvent thereof, followed by reaction with sulfur, and then with a compound of Z$_2$—A—Z$_1$ (wherein Z$_1$ and Z$_2$ are each a hydroxyl group or a reactive atom or a group derived from hydroxyl group such as halogen, methanesulfonyloxy or p-toluenesulfonyloxy; Z$_1$ and Z$_2$ are not hydroxyl groups at the same time; and A is as defined above).

The reaction proceeds in a suitable solvent which does not adversely affect the reaction, such as methanol, ethanol, propanol, N,N-dimethylformamide, benzene, toluene, tetrahydrofuran or acetonitrile in the presence of a suitable base such as sodium methoxide, sodium ethoxide, potassium t-butoxide, sodium hydride, potassium hydride, sodium hydroxide, potassium hydroxide, potassium carbonate or sodium carbonate at -20° C. to 150° C. for 30 minutes to 5 hours.

Of the starting compounds represented by the formula (II), the compound wherein X is —S(O)$_n$— (n=0) can be also produced by reacting 2-mercaptothiophene derivative with, for example, dialkylene dihalide in the presence of a base such as sodium hydroxide, potassium hydroxide, sodium hydride or sodium metal. The reaction solvent is exemplified by dimethylformamide, toluene, methanol or ethanol, and the reaction temperature is from 0° C. to a temperature near the boiling point of the solvent used, preferably from 0° C. to 80° C.

Of the starting compounds represented by the formula (II), the compound wherein X is —S(O)$_n$— (n=1, 2) can be produced by oxidating the compound wherein n=0.

Examples of the oxidizing agent to be used for this oxidation include m-chloroperbenzoic acid, peracetic acid, sodium bromite, and hydrogen peroxide, and examples of the solvent to be used for this reaction include chloroform, dichloromethane, tetrahydrofuran, dioxane, dimethylformamide, and water. The reaction temperature is from -70° C. to a temperature near the boiling point of the solvent used, preferably from -20° C. to 0° C.

Of the starting compounds represented by the formula (II) in Method 1, the compound wherein X is —CO— can be produced by reacting a compound of the formula

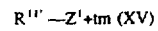

(XVI)

wherein each symbol is as defined above, with a carboxylic acid halide of the formula

  (XVII)

wherein each symbol is as defined above. The reaction proceeds in a suitable solvent which does not adversely affect the reaction, such as benzene, toluene, chloroform, methylene chloride or dichloroethane, in the presence of a Lewis acid such as aluminium chloride, tin chloride or iron chloride at −10° C. to 100° C. for 5 minutes to 20 hours.

Of the starting compounds represented by the formula (II) in Method 1, the compound wherein X is —CH(OH)— or —CH$_2$— can be produced by reducing a compound wherein X is —CO— using a suitable reducing agent such as sodium borohydride.

The reaction proceeds in a suitable solvent which does not adversely affect the reaction, such as methanol, ethanol, propanol, isopropyl alcohol, tetrahydrofuran, dichloromethane or dichloroethane, in the presence of a suitable reducing agent such as lithium aluminium hydride, sodium borohydride, sodium cyanoborohydride, trifluoroborodiethylate or triethylsilane at −10° C. to 100° C. for 30 minutes to 10 hours.

The thiophene compound of the formula (I) thus produced can be converted to an acid addition salt with the abovementioned inorganic acid or organic acid, if necessary. The compound having carboxylic group can be converted to a metal salt such as sodium, potassium or calcium salt; an amine salt with triethylamine, or the like; or a salt with an amino acid such as lysine or ornithine. Also, the compound can be obtained as a solvate such as hydrate.

When the compound of the present invention obtained in the aforementioned manner has an asymmetric center, it is normally produced as a racemate, which can be optically resolved into optical isomers by conventional methods such as fractional recrystallization, chromatography, etc. In addition, an optical isomer can be produced from an optically active starting material, and syn- or anti-isomer can be resolved by conventional methods.

EXPERIMENT EXAMPLE 1

Affinity for dopamine 2 receptor

A specific binding of dopamine 2 (D$_2$) receptor was tested according to the method described in Eur. J. Pharmacol. 46, 377 (1977).

A synaptosome fraction was separated from corpus striatum of 9–10 weeks old Wistar rat, and suspended in 50 mM Tris-HCl buffer (pH 7.1) containing 120 mM sodium chloride, 5 mM potassium chloride, 2 mM calcium chloride, 1 mM magnesium chloride, 10 μM pargyline and 0.1% ascorbic acid for use in the test.

The test compound at several concentrations and tritiated spiperone (final concentration 0.2 nM) were added to the synaptosome suspension, and each mixture was reacted at 37° C. for 20 minutes. After the reaction, the reaction mixture was filtered with suction through a Whatman GF/B glass filter. The filter was washed with 50 mM Tris-HCl buffer (pH 7.7), and the radioactivity of the filter was measured by a liquid scintillation counter. Non-specific binding was determined in the presence of $10^{-4}$ M($\pm$)-sulpiride. The concentration necessary for 50% inhibition (IC$_{50}$) was determined on a graph, and inhibition constant (Ki value) was calculated. The results are shown in Table 1.

EXPERIMENT EXAMPLE 2

Affinity for serotonin 1A receptor

A specific binding of serotonin 1A (5-HT$_{1A}$) receptor was tested according to the method described in J. Neurochem. 44, 1685 (1985).

A crude synaptosome fraction was separated from hippocampus of 9–10 weeks old Wistar rat, and suspended in 50 mM Tris-HCl buffer (pH 7.4) containing 1 mM manganese chloride for use in the test. The test compound at several concentrations and tritiated 8-hydroxy-2-dipropylaminotetralin (8-OH-DPAT, final concentration 0.2 nM) were added to the synaptosome suspension, and each mixture was reacted at 37° C. for 12 minutes. After the reaction, the reaction mixture was filtered with suction through a Whatman GF/B glass filter. The filter was washed with 50 mM Tris-HCl buffer (pH 7.7), and the radioactivity of the filter was measured by a liquid scintillation counter. Non-specific binding was determined in the presence of $10^{-5}$M serotonin (5-HT). The concentration necessary for 50% inhibition (IC$_{50}$) was determined on a graph, and inhibition constant (Ki value) was calculated. The results are shown in Table 1.

EXPERIMENT EXAMPLE 3

Affinity for serotonin 2 receptor

A specific binding of serotonin 2 (5-HT$_2$) receptor was tested according to the method described in Mol. Pharmacol. 21, 301 (1981).

A crude synaptosome fraction was separated from hippocampus of 9–10 weeks old Wistar rat, and suspended in 50 mM Tris-HCl buffer (pH 7.7) for use in the test. The test compound at several concentrations and tritiated ketanserin (final concentration 0.2 nM) were added to the synaptosome suspension, and each mixture was incubated at 37° C. for 20 minutes. After the incubation, the mixture was filtered with suction through a Whatman GF/B glass filter. The filter was washed with 50 mM Tris-HCl buffer (pH 7.7), and the radioactivity of the filter was measured by a liquid scintillation counter. Non-specific binding was determined in the presence of $10^{-5}$M mianserin. The concentration necessary for 50% inhibition (IC$_{50}$) was determined on a graph, and inhibition constant (Ki value) was calculated. The results are shown in Table 1.

EXPERIMENT EXAMPLE 4

Anti-apomorphine action (mouse)

Male dd mice were used for the test (3 per group). The test compound was orally administered to the mice, and 60 minutes later, 0.5 mg/kg of apomorphine hydrochloride was subcutaneously administered. The movement for 20 minutes from immediately after the administration was measured using Balimex (Columbus, USA). Each group was tested three times, and the amount of the test compound necessary to lower the movement by 50% than that of a comparison group was calculated from a graph and taken as ED$_{50}$. The results are shown in Table 1.

TABLE 1

| test compound (Ex. No.) | binding (nM) $D_2$ | $5\text{-}HT_{1A}$ | $5\text{-}HT_2$ | anti-apomorphine effect $ED_{50}$ (mg/kg p.o.) |
|---|---|---|---|---|
| 21  | 1.3  | 0.12 | 0.59  | 3.5  |
| 36  | 0.61 | 0.75 | 1.3   | 3.4  |
| 40  | 0.71 | 0.35 | 0.45  | 1.0  |
| 93  | 0.8  | 26   | 0.79  | 2.9  |
| 95  | 2.5  | 140  | 0.059 | 2.6  |
| 108 | 2.0  | 56   | 2.1   | 0.41 |
| 119 | 3.8  | 14   | 0.65  | 0.16 |
| 151 | 3.8  | 15   | 0.099 | 0.76 |
| 155 | 1.4  | >100 | 0.37  | 1.2  |
| 158 | 0.94 | 16   | 0.13  | 0.14 |
| 159 | 0.5  | 12   | 0.047 | 0.53 |
| 165 | 0.69 | 1.7  | 1.3   | 0.24 |

EXPERIMENT EXAMPLE 5

Acute toxicity

Male ddY mice were used at 5 per group, and intraperitoneally administered with 100 mg/kg of the compound of Example 4. No death was observed for 5 days after the administration. In a similar manner, 300 mg/kg of the compound was orally administered, and no death was observed for 5 days after the administration.

The compound of the present invention possesses pharmacological actions required of an antipsychotic such as motility suppressing action, anti-apomorphine action, methamphetamine antagonistic action, tetrabenazine-induced blepharoptosis enhancing action, and the like, and additionally possesses strong inhibitory action on serotonin-induced head-twitch. In the determination of affinity for receptors using tritium-labeled ligands, the compound of the invention showed high affinity for dopamine ($D_2$) receptor and serotonin (5-$HT_2$) receptor. Furthermore, catalepsy inducing action, which is an index of extrapyramidal side-effects, was examined using rats, and the compound of the invention showed extremely weak action, from which result the compound of the invention has been proved to be useful as an antipsychotic causing less extrapyramidal side-effects. Also, the compound of the invention has been found to show high affinity for serotonin (5-$HT_{1A}$) receptor, and has an antianxiety action, and the compound is also useful as a non-benzodiazepine type antianxiety agent.

When the compound of the invention is used as a pharmaceutical, it is usually admixed with vehicles, diluents, solubilizers, and so on, and safely administered to patients in the form of tablet, powder, granule, capsule, injection, transfusion, etc. While the dose varies depending on symptom, body weight, age, etc. of patients, it is normally administered to an adult in the range of from 1 to 500 mg per day in a single or several times divided doses.

The present invention is hereinbelow described in detail by way of reference examples and examples. It should be understood that the present invention is not limited to these examples.

REFEREMCE EXAMPLE 1

To a solution of 2-(1-ethylenedioxyethyl)thiophene (30 g) in tetrahydrofuran (250 ml) was dropwise added n-butyl lithium (110 ml) at −50° C., after which sulfur (5.6 g) was added thereto, and the mixture was stirred for 2 hours. 1-Bromo-3-chloropropane (28 g) was added at −50° C., and the mixture was stirred at room temperature for 2 hours. The reaction mixture was poured into water, extracted with ethyl acetate, and dried over magnesium sulfate, whereafter the solvent was distilled off under reduced pressure. The residue was dissolved in 300 ml of tetrahydrofuran, diluted hydrochloric acid (100 ml) was added thereto, and the mixture was stirred at room temperature for 15 hours. The reaction mixture was poured into water, extracted with ethyl acetate, and dried over magnesium sulfate. Then, the solvent was distilled off under reduced pressure. The residue was purified by silica gel column chromatography to give 15 g of 2-acetyl-5-(3-chloropropylthio)thiophene.

REFERENCE EXAMPLE 2

In a similar manner as in Reference Example 1 except the use of 2-(ethylenedioxymethyl)thiophene in place of 2-(1-ethylenedioxyethyl)thiophene, 2-formyl-5-(3-chloropropylthio)thiophene was obtained. A solution of hydroxylamine hydrochloride (11 g) in ethanol (100 ml) was neutralized with aqueous sodium hydroxide, and thereto was added 2-formyl-5-(3-chloropropylthio)thiophene (10 g). The mixture was stirred at 45° C. for 30 minutes, and concentrated. The residue was added with water, extracted with ethyl acetate, and washed with water, and then the solvent was distilled off. The residue (11 g) was dissolved in 36 ml of acetic acid and 12 ml of acetic anhydride, and 11 g of zinc dust was added thereto at 40° C. Then, the mixture was stirred for 30 minutes. The reaction mixture was filtered, and the filtrate was concentrated to give 6.4 g of 2-acetylaminomethyl-5-(3-chloropropylthio)thiophene.

EXAMPLE 1

A mixture of 2-acetyl-5-(4-chlorobutylthio)thiophene (5 g), 2-pyrimidinylpiperazine hydrochloride (5 g), potassium carbonate (8.3 g), potassium iodide (3.3 g), dimethylformamide (50 ml), and toluene (50 ml) was stirred at 90° C. for 4 hours. The reaction mixture was cooled with water, water was added thereto, and the mixture was extracted with ethyl acetate. The organic layer was washed with brine, dried over magnesium sulfate, and concentrated. The residue was purified by silica gel column chromatography, and then ethanol-hydrochloric acid was added thereto to give hydrochloride. Recrystallization from ethanol gave 5.6 g of 1-(4-((5-acetyl-2-thienyl)thio) butyl)-4-(2-pyrimidinyl)piperazine hydrochloride as white crystals, m.p. 180°–181° C.

EXAMPLE 2

In a similar manner as in Example 1 except the use of 2acetyl-5-(2-chloroethylthio)thiophene in place of 2-acetyl-5(4-chlorobutylthio)thiophene, and 1-(3-trifluoromethylphenyl)piperazine in place of 2-pyrimidinylpiperazine hydrochloride, 1-(2-((5-acetyl-2-thienyl)thio)ethyl)-4-(3-trifluoromethyl phenyl)piperazine hydrochloride was obtained, m.p. 175°–177° C.

EXAMPLE 3

In a similar manner as in Example 1 except the use of 2-acetyl-5-(3-chloropropylthio)thiophene in place of 2-acetyl-5-(4-chlorobutylthio)thiophene, and 1-(3-trifluoromethylphenyl)piperazine in place of 2-pyrimidinylpiperazine hydrochloride, 1-(3-((5-acetyl-2-thienyl)thio)propyl)-4-(3-trifluoromethyl phenyl)piperazine hydrochloride was obtained, m.p. 162°–164° C.

EXAMPLE 4

In a similar manner as in Example 1 except the use of 2-acetyl-5-(3-chloropropylthio)thiophene in place of 2-acetyl-5-(4-chlorobutylthio)thiophene, and 1-(2,3-dimethylphenyl)piperazine in place of 2-pyrimidinylpiperazine hydrochloride, 1-(3-((5-acetyl-2-thienyl)thio)propyl)-4-(2,3-dimethylphenyl) piperazine hydrochloride, m.p. 215°–217° C.

EXAMPLE 5

A mixture of 1-(2-((5-acetyl-2-thienyl)thio)ethyl)-4-(3-trifluoromethylphenyl)piperazine hydrochloride (2.5 g), hydroxylamine hydrochloride (0.7 g), sodium hydrogencarbonate (1.2 g), and ethanol (50 ml) was heated under reflux for 8 hours. The reaction mixture was concentrated, and to the residue was added water, and extracted with chloroform. After washing with water and drying over magnesium sulfate, the solvent was distilled off under reduced pressure. The residue was recrystallized from isopropyl alcohol to give 1.8 g of 1-(2-((5-(1-hydroxyiminoethyl)-2-thienyl)thio)ethyl)-4-(3-trifluoromethylphenyl)piperazine, m.p. 140°–147° C.

EXAMPLE 6

In a similar manner as in Example 5 except the use of 1-(3-((5-acetyl-2-thienyl)thio)propyl)-4-(3-trifluoromethylphenyl)piperazine hydrochloride in place of 1-(2-((5-acetyl-2-thienyl)thio)ethyl)-4-(3-trifluoromethylphenyl)piperazine hydrochloride, 1-(3-((5-(1-hydroxyiminoethyl)-2-thienyl)thio)propyl)-4-(3-trifluoromethylphenyl)piperazine as a pale brown oil.

EXAMPLE 7

A mixture of 1-(3-((5-(1-hydroxyiminoethyl)-2-thienyl)thio)propyl)-4-(3-trifluoromethylphenyl)piperazine (1.8 g) and polyphosphoric acid (20 g) was stirred while heating at 75° C. for 30 minutes. Water was added to the reaction mixture, and the mixture was made alkaline with potassium carbonate, and extracted with ethyl acetate. The organic layer was washed with brine, dried over magnesium sulfate, and concentrated. The residue was purified by silica gel column chromatography, and recrystallized from ethyl acetate-isopropyl ether to give 0.3 g of 1-(3-((5-acetylamino-2-thienyl)thio)propyl)-4-(3-trifluoromethylphenyl)piperazine ⅓ hydrate, m.p. 127°–128° C.

EXAMPLE 8

To a solution of 1-(3-((5-acetyl-2-thienyl)thio)propyl)-4-(3-trifluoromethylphenyl)piperazine (11 g) in acetic acid (200 ml) was added a solution of sodium metaperiodate (3 g) and water (15 ml) while stirring at room temperature. The mixture was stirred at room temperature for 1 hour, poured into water, and made alkaline with potassium carbonate. The separated oily substance was extracted twice with ethyl acetate. The organic layer was collected, washed with aqueous sodium hydrogensulfite, and dried over magnesium sulfate, and the solvent was distilled off under reduced pressure. The residue was purified by silica gel column chromatography, and the oily substance obtained was added with ethanol-hydrochloric acid to give hydrochloride thereof. Recrystallization from ethanol gave 2.8 g of 1-(3-((5-acetyl-2-thienyl)sulfinyl)propyl)-4-(3-trifluoromethylphenyl)piperazine hydrochloride as white crystals, m.p. 183°–184° C.

EXAMPLE 9

A mixture of 2-acetyl-5-(3-chloropropylsulfonyl)thiophene (5.3 g), 2-pyrimidinylpiperazine hydrochloride (6.2 g), potassium carbonate (6 g), potassium iodide (1.3 g), dimethylformamide (50 ml), and toluene (50 ml) was stirred at 90° C. for 4 hours. The reaction mixture was cooled with water, water was added thereto, and extracted with ethyl acetate. The organic layer was washed with brine, dried over magnesium sulfate, and concentrated. The residue was purified by silica gel column chromatography, and added with ethanol-hydrochloric acid to give hydrochloride. Recrystallization from ethanol gave 1.2 g of 1-(3-((5-acetyl-2-thienyl)sulfonyl)propyl)-4-(2-pyrimidinyl)piperazine hydrochloride as white crystals, m.p. 204°–205° C.

EXAMPLE 10

A mixture of 1-(3-((5-acetyl-2-thienyl)thio)propyl)-4-(2,3-dimethylphenyl)piperazine (0.9 g), sodium borohydride (0.3 g), and methanol (50 ml) was stirred at room temperature for 1 hour. Water was added to the mixture, and the mixture was extracted with ethyl acetate. The organic layer was washed with brine, dried over magnesium sulfate, and concentrated. The residue was purified by silica gel column chromatography. The obtained oily substance was converted to maleate. Recrystallization from isopropyl alcohol gave 1-(3-((5-(1-hydroxyethyl)-2-thienyl)thio)propyl)-4-(2,3-dimethylphenyl)piperazine maleate as white crystals, m.p. 126°–128° C.

The following compounds were obtained in the same manner.

(11) 1-(3-((5-acetyl-2-thienyl)thio)propyl)-4-(2-methoxyphenyl)piperazine hydrochloride, m.p. 168°–171° C.

(12) 1-(3-((5-acetylamino-2-thienyl)thio)propyl)-4-(2-methoxyphenyl)piperazine hydrochloride monohydrate, m.p. 186°–188° C.

(13) 1-(3-((3-acetyl-5-methyl-2-thienyl)thio)propyl)-4-(3-trifluoromethylphenyl)piperazine hydrochloride, m.p. 192°–195° C.

(14) 1-(3-((5-methyl-2-thienyl)thio)propyl)-4-(3-trifluoromethylphenyl)piperazine hydrochloride, m.p. 155°–157° C.

(15) 1-(3-((5-(1-hydroxyiminoethyl)-2-thienyl)sulfonyl)propyl)4-(3-trifluoromethylphenyl)piperazine, m.p. 152°–155° C.

(16) 1-(3-((5-acetyl-2-thienyl)thio)propyl)-4-(2-pyrimidinyl)piperazine dihydrochloride, m.p. 214°–216° C.

(17) 1-(3-((5-(1-hydroxyiminoethyl)-2-thienyl)thio)propyl)-4(2,3-dimethylphenyl)piperazine, m.p. 147°–149° C.

(18) 1-(3-((5-methyl-2-thienyl)sulfonyl)propyl)-4-(3-trifluoromethylphenyl)piperazine, m.p. 82°–83° C.

(19) 1-(3-(2-thienylthio)propyl)-4-(3-trifluoromethylphenyl)piperazine hydrochloride, m.p. 155°–157° C.

(20) 1-(3-((5-methyl-2-thienyl)sulfinyl)propyl)-4-(3-trifluoromethylphenyl)piperazine, m.p. 92°–94° C.

(21) 3-(4-(3-((5-acetyl-2-thienyl)thio)propyl)-1-piperadinyl)-1,2-benzisothiazole hydrochloride, m.p. 202°–203° C.

(22) 1-(4-((5-acetyl-2-thienyl)thio)butyl)-4-(3-trifluoromethylphenyl)piperidine hydrochloride, m.p. 129°–131° C.

(23) 1-(3-((5-acetyl-2-thienyl)thio)propyl)-4-(4-fluorobenzoyl)piperidine maleate, m.p. 128°–130° C.

(24) 1-(3-((3-acetyl-5-methyl-2-thienyl)thio)propyl)-4-methylpiperazine dihydrochloride, m.p. 242°–246° C.

(25) 1-(3-((5-methyl-2-thienyl)thio)propyl)-4-(2-methoxyphenyl)piperazine hydrochloride monohydrate, m.p. 190°–195° C.

(26) 1-(3-((3-benzoyl-5-methyl-2-thienyl)thio)propyl)-4-methylpiperazine dihydrochloride, m.p. 208°–211° C.

(27) 1-(3-((3-benzoyl-5-methyl-2-thienyl)thio)propyl)-4-(3-trifluoromethylphenyl)piperazine dihydrochloride, m.p. 148°–150° C.

(28) 1-(3-((5-methyl-2-thienyl)thio)propyl)-4-(2-oxo-1-benzimidazolinyl)piperidine, m.p. 111°–113° C.
(29) 1-(3-((3-benzoyl-5-methyl-2-thienyl)thio)propyl)-4-(2-oxo-1-benzimidazolinyl)piperidine, m.p. 186°–190° C.
(30) 1-(3-((3-acetyl-5-methyl-2-thienyl)thio)propyl)-4-(2-methoxyphenyl)piperazine, m.p. 104°–106° C.
(31) 1-(4-((5-acetyl-2-thienyl)thio)butyl)-4-(2-methoxyphenyl)piperazine dihydrochloride, m.p. 219°–220° C.
(32) 1-(2-((5-acetylamino-2-thienyl)thio)ethyl)-4-(2-methoxyphenyl)piperazine, m.p. 140°–142° C.
(33) 1-(3-((5-acetyl-2-thienyl)thio)propyl)-4-(3-chlorophenyl)piperazine hydrochloride ½ hydrate, m.p. 170°–173° C.
(34) 1-(2-((5-acetyl-2-thienyl)thio)ethyl)-4-(2-methoxyphenyl)piperazine dihydrochloride, m.p. 201°–202° C.
(35) 3-(1-(2-((5-acetyl-2-thienyl)thio)ethyl)piperidin-4-yl)-6-fluoro-1,2-benzisoxazole, m.p. 98°–101° C.
(36) 3-(1-(3-((5-acetyl-2-thienyl)thio)propyl)piperidin-4-yl)-6-fluoro-1,2-benzisoxazole hydrochloride, m.p. 183°–185° C.
(37) 3-(1-(4-((5-acetyl-2-thienyl)thio)butyl)piperidin-4-yl)-6-fluoro-1,2-benzisoxazole oxalate, m.p. 137°–141° C.
(38) 1-(4-((5-acetyl-2-thienyl)thio)butyl)-4-(bis(4-chlorophenyl)methyl)piperadine oxalate, m.p. 133°–137° C.
(39) 1-(3-((5-acetylamino-2-thienyl)sulfonyl)propyl))-4-(3-trifluoromethylphenyl)piperazine, m.p. 164°–166° C.
(40) 3-(1-(3-((5-acetylamino-2-thienyl)thio)propyl)piperidin-4-yl)-6-fluoro-1,2-benzisoxazole oxalate, m.p. 114°–117° C.
(41) 1-(6-((5-acetyl-2-thienyl)thio)hexyl)-4-(2-methoxyphenyl)piperazine dihydrochloride, m.p. 182°–184° C. (decomposition)
(42) 3-(1-(3-((5-acetylamino-2-thienyl)thio)propyl)piperidin-4-yl)-1,2-benzisothiazole hydrochloride ½ hydrate, m.p. 227°–229° C. (decomposition)
(43) 1-(3-((5-acetylamino-2-thienyl)thio)propyl)-4-(2,3-dimethylphenyl)piperazine, m.p. 112°–113° C.

In the same manner, the following compounds can be obtained.

(44) 3-(4-(6-((5-acetyl-2-thienyl)thio)hexyl)-1-piperazinyl-1,2-benzisothiazole
(45) 3-(1-(6-((5-acetyl-2-thienyl)thio)hexyl)piperidin-4-yl)-6-fluoro-1,2-benzisoxazole
(46) 3-(1-(3-((5-benzoyl-2-thienyl)thio)propyl)piperidin-4-yl)-6-fluoro-1,2-benzisoxazole
(47) 3-(4-(3-((5-benzoyl-2-thienyl)thio)propyl)-1-piperazinyl)-1,2-benzisoxazole
(48) 5-((2-(4-(6-fluoro-1,2-benzisoxazol-3-yl)piperidino)ethyl)thio)thiophene-2-carboxylic acid
(49) 5-((3-(4-(6-fluoro-1,2-benzisoxazol-3-yl)piperidino)propyl)-thio)thiophene-2-carboxylic acid
(50) 5-((4-(4-(6-fluoro-1,2-benzisoxazol-3-yl)piperidino)butyl)thio)thiophene-2-carboxylic acid
(51) 5-((6-(4-(6-fluoro-1,2-benzisoxazol-3-yl)piperidino)hexyl)thio)thiophene-2-carboxylic acid
(52) 3-(1-(2-((5-formyl-2-thienyl)thio)ethyl)piperidin-4-yl)-6-fluoro-1,2-benzisoxazole
(53) 3-(1-(3-((5-formyl-2-thienyl)thio)propyl)piperidin-4-yl)-6-fluoro-1,2-benzisoxazole
(54) 1-(3-((5-formyl-2-thienyl)thio)propyl)-4-((4-phenyl-2-pyrrolyl)carbonyl)piperazine
(55) 3-(1-(4-((5-formyl-2-thienyl)thio)butyl)piperidin-4-yl)-6-fluoro-1,2-benzisoxazole
(56) 1-(4-((5-formyl-2-thienyl)thio)butyl)-4-((4-phenyl-2-pyrrolyl)carbonyl)piperazine
(57) 3-(1-(6-((5-formyl-2-thienyl)thio)hexyl)piperidin-4-yl)-6-fluoro-1,2-benzisoxazole
(58) 1-(6-((5-formyl-2-thienyl)thio)hexyl)-4-((4-phenyl-2pyrrolyl)carbonyl)piperazine
(59) 3-(4-(2-((5-bromo-2-thienyl)thio)ethyl)-1-piperazinyl)-1,2-benzisothiazole
(60) 1-(2-((5-bromo-2-thienyl)thio)ethyl)-4-((4-phenyl-2-pyrrolyl)carbonyl)piperazine
(61) 3-(1-(3-((5-bromo-2-thienyl)thio)propyl)piperidin-4-yl)-6)-fluoro-1,2-benzisoxazole
(62) 1-(3-((5-bromo-2-thienyl)thio)propyl)-4-((4-phenyl-2-pyrrolyl)carbonyl)piperazine
(63) 3-(1-(4-((5-bromo-2-thienyl)thio)butyl)piperidin-4-yl)-6-fluoro-1,2-benzisoxazole
(64) 1-(4-((5-bromo-2-thienyl)thio)butyl)-4-((4-phenyl-2-pyrrolyl)carbonyl)piperazine
(65) 3-(1-(6-((5-bromo-2-thienyl)thio)hexyl)piperidin-4-yl)-6-fluoro-1,2-benzisoxazole
(66) 1-(6-((5-bromo-2-thienyl)thio)hexyl)-4-((4-phenyl-2-pyrrolyl)carbonyl)piperazine
(67) 3-(1-(2-((5-nitro-2-thienyl)thio)ethyl)piperidin-4-yl)-6-fluoro-1,2-benzisoxazole
(68) 1-(2-((5-nitro-2-thienyl)thio)ethyl)-4-((4-phenyl-2-pyrrolyl)carbonyl)piperazine
(69) 3-(1-(3-((5-nitro-2-thienyl)thio)propyl)piperidin-4-yl)-6-fluoro-1,2-benzisoxazole
(70) 1-(3-((5-nitro-2-thienyl)thio)propyl)-4-((4-phenyl-2-pyrrolyl)carbonyl)piperazine
(71) 3-(1-(4-((5-nitro-2-thienyl)thio)butyl)piperidin-4-yl)-6-fluoro-1,2-benzisoxazole
(72) 1-(4-((5-nitro-2-thienyl)thio)butyl)-4-((4-phenyl-2-pyrrolyl)carbonyl)piperazine
(73) 3-(1-(6-((5-nitro-2-thienyl)thio)hexyl)piperidin-4-yl)-6-fluoro-1,2-benzisoxazole
(74) 1-(6-((5-nitro-2-thienyl)thio)hexyl)-4-((4-phenyl-2-pyrrolyl)carbonyl)piperazine
(75) 1-(2-((5-amino-2-thienyl)thio)ethyl)-4-(2-methoxyphenyl)piperazine
(76) 3-(1-(2-((5-amino-2-thienyl)thio)ethyl)piperidin-4-yl)-6-fluoro-1,2-benzisoxazole
(77) 1-(2-((5-amino-2-thienyl)thio)ethyl)-4-((4-phenyl-2-pyrrolyl)carbonyl)piperazine
(78) 3-(1-(3-((5-amino-2-thienyl)thio)propyl)piperidin-4-yl)-6-fluoro-1,2-benzisoxazole
(79) 1-(3-((5-amino-2-thienyl)thio)propyl)-4-(2-methoxyphenyl)piperazine
(80) 1-(3-((5-amino-2-thienyl)thio)propyl)-4-((4-phenyl-2-pyrrolyl)carbonyl)piperazine
(81) 1-(4-((5-amino-2-thienyl)thio)butyl)-4-(2-methoxyphenyl)piperazine
(82) 3-(1-(4-((5-amino-2-thienyl)thio)butyl)piperidin-4-yl)-6-fluoro-1,2-benzisoxazole
(83) 3-(1-(6-((5-amino-2-thienyl)thio)hexyl)piperidin-4-yl)-6-fluoro-1,2-benzisoxazole
(84) 1-(6-((5-amino-2-thienyl)thio)hexyl)-4-(2-methoxyphenyl)piperazine
(85) 3-(1-(2-((5-acetylamino-2-thienyl)thio)ethyl)piperidin-4-yl)-6-fluoro-1,2-benzisoxazole
(86) 3-(1-(2-((5-methylcarbamoyl-2-thienyl)thio)ethyl)piperidin-4-yl)-6-fluoro-1,2-benzisoxazole
(87) 4-(4-fluorophenyl)-2-(4-(3-((5-acetyl-2-thienyl)thio)propyl)piperazin-1-yl)-7,8-dihydro-5H-thiopyrano[4,3-b]-pyridine oxalate ½ hydrate, m.p. 103°–106° C.
(88) 2-acetyl-5-(4-(2-oxo-2,3,5,6,7,8-hexahydroimidazo[1,2-a]pyridine-3-spiro-4'-piperidino)butylthio)thiophene dihydrochloride ½ hydrate, m.p. 245°–250° C. (decomposition)
(89) 2-acetyl-5-(4-(4-carbamoyl-4-piperidinopiperidino)butylthio)thiophene dihydrochloride ½ hydrate, m.p. 240°–243° C. (decomposition)

(90) 3-(1-(3-((5-formyl-2-thienyl)thio)propyl)piperidin-4-yl)-6-fluoro-1,2-benzisoxazole oxalate ½ hydrate, m.p. 148°–150° C.

(91) 3-(1-(3-((5-cyano-2-thienyl)thio)propyl)piperidin-4-yl)-6-fluoro-1,2-benzisoxazole oxalate ½ hydrate, m.p. 149°–151° C.

(92) 3-(1-(3-((5-acetylaminomethyl-2-thienyl)sulfinyl)propyl)piperidin-4-yl)-6-fluoro-1,2-benzisoxazole oxalate monohydrate, m.p. 128°–130° C.

(93) 3-(1-(3-((5-acetylaminomethyl-2-thienyl)thio)propyl)piperidin-4-yl)-6-fluoro-1,2-benzisoxazole fumarate ½ hydrate, m.p. 98°–100° C.

(94) 3-(1-(3-(5-acetylaminomethyl-2-thienyl)thio)-2-methylpropyl)piperidin-4-yl)-6-fluoro-1,2-benzisoxazole oxalate ½ hydrate, m.p. 77°–79° C.

REFERENCE EXAMPLE 3

To a mixture of 2-acetylaminomethylthiophene (15 g) and 4-chlorobutyryl chloride (17.7 g) in dichloroethane (150 ml) was added aluminium chloride (32 g) under ice-cooling, and the mixture was stirred for 4 hours. The reaction mixture was poured into ice-water, and extracted with chloroform. The organic layer was washed with water, and dried over magnesium sulfate, and then the solvent was distilled off under reduced pressure to give 25 g of 2-acetylaminomethyl-5-(4-chlorobutyryl)thiophene.

REFERENCE EXAMPLE 4

A mixture of 2-acetylaminomethyl-5-(4-chlorobutyryl)thiophene (15 g) in triethylsilane (21.6 ml) and trifluoroacetic acid (70 ml) was stirred at room temperature for 10 hours. The reaction mixture was poured into water, extracted with ethyl acetate, and dried over magnesium sulfate, and then the solvent was distilled off under reduced pressure. The residue was purified by silica gel column chromatography to give 10 g of 2-acetylaminomethyl-5-(4-chlorobutyl)thiophene.

EXAMPLE 95

A mixture of 2-acetylaminomethyl-5-(4-chlorobutyryl)thiophene (2.6 g), 4-(6-fluoro-1,2-benzisoxazol-3-yl)piperidine (2–7 g), potassium carbonate (3.0 g), potassium iodide (1.6 g), dimethylformamide (20 ml), and toluene (20 ml) was stirred at 60° C. for 6 hours. The reaction mixture was poured into water, and the precipitated crystals were filtered off, followed by recrystallization from ethanol to give 0.9 g of 3-(1-(4-(5-acetylaminomethyl-2-thienyl)-4-oxobutyl)piperidin-4-yl)-6-fluoro-1,2-benzisoxazole as white crystals, m.p. 140°–142° C.

EXAMPLE 96

A mixture of 2-acetylaminomethyl-5-(4-chlorobutyryl)thiophene (3 g), 1-(3-trifluoromethylphenyl)piperazine hydrobromide (4 g), potassium carbonate (3.5 g), potassium iodide (2 g), dimethylformamide (25 ml), and toluene (25 ml) was stirred at 60° C. for 7 hours. The reaction mixture was poured into water, extracted with toluene, and dried over magnesium sulfate, and then the solvent was distilled off under reduced pressure. The residue was purified by silica gel column chromatography, and converted to fumarate, followed by recrystallization from acetone to give 0.9 g of 1-(4-(5-acetylaminomethyl-2-thienyl)-4-oxobutyl)-4-(3-trifluoromethylphenyl)piperazine fumarate as white crystals, m.p. 135°–137° C.

EXAMPLE 97

In a similar manner as in Example 95 except the use of 1-(1,2-benzisothiazol-3-yl)piperazine in place of 4-(6-fluoro-1,2-benzisoxazol-3-yl)piperidine, 3-(1-(4-(5-acetylaminomethyl-2-thienyl)-4-oxobutyl)piperazin-4-yl)-1,2-benzisothiazole was obtained, m.p. 111°–114° C.

EXAMPLE 98

To a solution of 3-(1-(4-(5-acetylaminomethyl-2-thienyl)-4-oxobutyl)piperazin-4-yl)-1,2-benzisothiazole (0.3 g) in water (10 ml) was added conc. sulfuric acid (0.3 ml), and the mixture was refluxed for 2 hours. The reaction mixture was poured into water, and made alkaline with potassium carbonate, followed by extraction with chloroform. The organic layer was dried over magnesium sulfate, and the solvent was distilled off under reduced pressure. The residue was converted to oxalate, and recrystallized from ethanol to give 0.1 g of 3-(1-(4-(5-aminomethyl-2-thienyl)-4-oxobutyl)piperazin-4-yl)-1,2-benzisothiazole oxalate as white crystals, m.p. 200°–202° C.

EXAMPLE 99

In a similar manner as in Example 1 except the use of 2-acetylaminomethyl-5-(4-chlorobutyl)thiophene in place of 2-acetylaminomethyl-5-(4-chlorobutyryl)thiophene and 1-(1,2-benzisothiazol-3-yl)piperazine in place of 4-(6-fluoro-1,2-benzisoxazol-3-yl)piperidine, 3-(1-(4-(5-acetylaminomethyl-2-thienyl)butyl)piperazin-4-yl)-1,2-benzisothiazole was obtained, m.p. 109°–111° C.

EXAMPLE 100

To a solution of 3-(1-(4-(5-aminomethyl-2-thienyl)-4-oxobutyl)piperazin-4-yl)-1,2-benzisothiazole (1.5 g), triethylamine (5 ml), and tetrahydrofuran (10 ml) was added benzoylchloride (2 ml) under ice-cooling, and the mixture was stirred for 30 minutes. The reaction mixture was poured into water, and the precipitated crystals were filtered off, and recrystallized from isopropyl alcohol to give 1.4 g of 3-(1-(4-(5-(2-benzoylaminomethyl)-2-thienyl)-4-oxobutyl)piperazin-4-yl)-1,2-benzisothiazole as white crystals, m.p. 107°–109° C.

In a similar manner, the following compounds were obtained.

(101) 3-(1-(4-(5-methylcarbamoylmethyl-2-thienyl)-4-oxobutyl)piperazin-4-yl)-1,2-benzisothiazole, m.p. 118°–120° C.

(102) 1-(4-(5-acetylaminomethyl-2-thienyl)-4-oxobutyl)-4-(5-trifluoromethyl-2-pyridyl)piperazine, m.p. 176°–178° C.

(103) 3-(1-(4-(5-(1-acetylaminoethyl)-2-thienyl)-4-oxobutyryl)piperidin-4-yl)-6-fluoro-1,2-benzisoxazole, m.p. 124°–127° C.

(104) 3-(1-(4-(5-(2-acetylaminoethyl)-2-thienyl)-4-oxobutyl)piperazin-4-yl)-1,2-benzisothiazole hydrochloride ½ hydrate, m.p. 207°–208° C. (decomposition)

(105) 3-(1-(4-(5-(2-acetylaminoethyl)-2-thienyl)-4-oxobutyl)piperidin-4-yl)-6-fluoro-1,2-benzisoxazole, m.p. 139°–140° C.

(106) 3-(1-(4-(5-methylcarbamoylmethyl-2-thienyl)-4-oxobutyl)piperidin-4-yl)-6-fluoro-1,2-benzisoxazole, m.p. 147°–148° C.

(107) 3-(1-(3-(5-acetylaminomethyl-2-thienyl)-3-oxopropyl)piperidin-4-yl)-6-fluoro-1,2-benzisoxazole, m.p. 149°–150° C.

(108) 3-(1-(4-(5-acetylaminomethyl-2-thienyl)butyl)piperidin-4-yl)-6-fluoro-1,2-benzisoxazole, m.p. 73°–75° C (109) 3-(1-(4-(5-(3-fluorobenzoylaminomethyl)-2-thienyl)-4-oxobutyl)piperidin-4-yl)-6-fluoro-1,2-benzisoxazole oxalate ½ hydrate, m.p. 155°–157° C.

(110) 3-(1-(4-(5-carbamoylmethyl-2-thienyl)-4-oxobutyl)piperidin-4-yl)-6-fluoro-1,2-benzisoxazole hydrate, m.p. 146°–147° C.

(111) 3-(1-(2-(5-acetylaminomethyl-2-thienyl)-2-oxoethyl)piperidin-4-yl)-6-fluoro-1,2-benzisoxazole, m.p. 132°–134° C.
(112) 3-(1-(4-(5-trifluoroacetylaminomethyl-2-thienyl)-4-oxobutyl)piperidin-4-yl)-6-fluoro-1,2-benzisoxazole, m.p. 113°–115° C.
(113) 3-(1-(4-(5-propionylaminomethyl-2-thienyl)-4-oxobutyl)piperazin-4-yl)-1,2-benzisothiazole, m.p. 75°–77° C.
(114) 3-(1-(4-(5-mesylaminomethyl-2-thienyl)-4-oxobutyl)piperazin-4-yl)-1,2-benzisothiazole hydrochloride hydrate, m.p. 216°–219° C.
(115) 3-(1-(4-(5-butyl-2-thienyl)-4-oxobutyl)piperidin-4-yl)-6-fluoro-1,2-benzisoxazole hydrochloride, m.p. 202°–203° C.
(116) 3-(1-(4-(2-thienyl)-4-oxobutyl)piperidin-4-yl)-6-fluoro-1,2-benzisoxazole, m.p. 97°–99° C.
(117) 3-(1-(6-(5-acetylaminomethyl-2-thienyl)-6-oxohexyl)piperidin-4-yl)-6-fluoro-1,2-benzisoxazole, m.p. 107°–109° C.
(118) 3-(1-(5-(5-acetylaminomethyl-2-thienyl)-5-oxopentyl)piperidin-4-yl)-6-fluoro-1,2-benzisoxazole, m.p. 154°–156° C.
(119) 3-(1-(2-(5-acetylaminomethyl-2-thienyl)ethyl)piperidin-4-yl)-6-fluoro-1,2-benzisoxazole, m.p. 98°–99° C.
(120) 3-(1-(2-(5-acetylaminomethyl-2-thienyl)-2-hydroxyethyl)piperidin-4-yl)-6-fluoro-1,2-benzisoxazole hydrochloride ½ hydrate, m.p. 102°–104° C.
(121) 3-(1-(2-(5-acetylmethylaminomethyl-2-thienyl)-2-oxoethyl)piperidin-4-yl)-6-fluoro-1,2-benzisoxazole hydrochloride ¼ hydrate, m.p. 112°–114° C.

In the same manner, the following compounds can be obtained.

(122) 3-(1-(4-(5-bromo-2-thienyl)-4-oxobutyl)piperazin-4-yl)-1,2-benzisothiazole
(123) 3-(1-(4-(5-nitro-2-thienyl)-4-oxobutyl)piperazin-4-yl)1,2-benzisothiazole
(124) 3-(1-(4-(5-amino-2-thienyl)-4-oxobutyl)piperazin-4-yl)-1,2-benzisothiazole
(125) 3-(1-(4-(5-formyl-2-thienyl)-4-oxobutyl)piperazin-4-yl)-1,2-benzisothiazole
(126) 5-(4-(4-(1,2-benzisothiazol-3-yl)-1-piperazinyl)butyryl)-thiophene- 2-carboxylic acid
(127) 3-(1-(4-(5-methyl-2-thienyl)-4-oxobutyl)piperazin-4-yl)-6-fluoro-1,2-benzisoxazole p (128) 3-(1-(4-(5-acetylaminomethyl-3-methyl-2-thienyl)-4-oxobutyl)piperidin-4-yl)-6-fluoro-1,2-benzisoxazole
(129) 3-(1-(4-(5-acetyl-2-thienyl)butyl)piperidin-4-yl)-6-fluoro-1,2-benzisoxazole
(130) 3-(1-(4-(5-acetylaminomethyl-2-thienyl)-4-hydroxybutyl)piperidin-4-yl)-6-fluoro-1,2-benzisoxazole
(131) 3-(1-(4-(5-acetylaminomethyl-2-thienyl)-4-hydroxybutyl)piperidin-4-yl)-1,2-benzisothiazole
(132) 3-(1-(4-(5-benzoyl-2-thienyl)butyl)piperidin-4-yl)-6-fluoro-1,2-benzisoxazole
(133) 1-(4-(5-hydroxymethyl-2-thienyl)butyl)-4-(3-trifluoromethylphenyl)piperazine
(134) 1-(4-(5-acetoxymethyl-2-thienyl)butyl)-4-(3-trifluoromethylphenyl)piperazine
(135) 1-(4-(5-acetylamino-2-thienyl)-4-oxobutyl)-4-(3-chlorophenyl)piperazine
(136) 1-(4-(5-benzoyloxymethyl-2-thienyl)butyl)-4-(2-methoxyphenyl)piperazine
(137) 1-(3-(5-phenylacetylamino-2-thienyl)propyl)-4-phenylpiperazine
(138) 3-(1-(3-(5-benzoylamino-2-thienyl)propyl)piperazin-4-yl)-1,2-benzisothiazole
(139) 3-(1-(3-(5-formylaminomethyl-2-thienyl)-3-oxopropyl)piperazin-4-yl)-1,2-benzisothiazole
(140) 1'-(4-(5-acetylaminomethyl-2-thienyl)-4-oxobutyl)2,3,5,6,7,8-hexahydro-2-oxoimidazo[1,2-a]pyridine-3-spiro-4'-piperidine
(141) 1-(2-(5-benzyl-2-thienyl)-2-oxoethyl)-4-(4-chlorophenyl)-4-hydroxypiperidine
(142) 3-(1-(4-(5-acetylaminomethyl-2-thienyl)-4-oxobutyl)piperazin-4-yl)-1,2-benzisothiazole S,S-dioxide
(143) 2-(1-(4-(5-acetylaminomethyl-2-thienyl)-4-oxobutyl)piperazin-4-yl)-4-phenylthiazole
(144) 3-(1-(4-(5-acetylaminomethyl-2-thienyl)-4-oxobutyl)piperazin-4-yl)indole
(145) 1-(4-(5-acetylaminomethyl-2-thienyl)-2,2-dimethyl-4-oxobutyl)-4-(2-methoxyphenyl)piperazine
(146) 1-(4-(5-acetylaminomethyl-2-thienyl)-4-oxobutyl)-4-(2-pyrimidinyl)piperazine
(147) 1-(4-(5-acetylaminomethyl-2-thienyl)-4-oxobutyl)-4-(5-fluoro-2-pyrimidinyl)piperazine
(148) 1-(4-(5-acetylaminomethyl-2-thienyl)-4-oxobutyl)-4-phenylcarbamoylpiperazine
(149) 1-(4-(5-acetylaminomethyl-2-thienyl)-4-oxobutyl)-4-ethylcarbamoylpiperazine
(150) 3-(1-(4-(5-acetylaminomethyl-2-thienyl)-4-hydroxybutyl)piperidin-4-yl)-6-fluoro-1,2-benzisocazole oxalate, m.p. 117°–120° C.
(151) 3-(1-(2-(5-acetylaminomethyl-4-methyl-2-thienyl)ethyl)piperidin-4-yl)-6-fluoro-1,2-benzisoxazole, m.p. 139°–140° C.
(152) 1-(2-(5-acetylaminomethyl-2-thienyl)ethyl)-4-(2-pyrimidinyl)piperazine, m.p. 103°–105° C.
(153) 1-(2-(5-acetylaminomethyl-2-thienyl)ethyl)-4-(4-chlorophenyl)-4-hydroxypiperidine, m.p. 131°–134° C.
(154) 3-(4-(2-(5-acetylaminomethyl-2-thienyl)ethyl)piperazin-1-yl)-1,2-benzisoxazole, m.p. 99°–100° C.
(155) 3-(1-(2-(5-acetylaminomethyl-2-methyl-3-thienyl)ethyl)piperidin-4-yl)-6-fluoro-1,2-benzisoxazole, m.p. 141°–143° C.
(156) 1-(2-(5-acetylaminomethyl-2-thienyl)ethyl)-4-(bis(4-fluorophenyl)methylene)piperidin oxalate, m.p. 137°–138° C.
(157) 1'-(2-(5-acetylaminomethyl-2-thienyl)ethyl)-4-(2-oxo-1,2,3,5,6,7,8,8a-octahydroimidazol[1,2-a]pyridine-3-spiro)piperidine dihydrochloride ½ hydrate, m.p. 247°–249° C.
(158) 3-(1-(2-(5-(2-acetylaminoethyl)-2-thienyl)ethyl)piperidin-4-yl)-6-fluoro-1,2-benzisoxazole ½ hydrate, m.p. 101°–103° C.
(159) 3-(1-(2-(5-(2-acetylaminoethyl)-4-bromo-2-thienyl)ethyl)piperidin-4-yl)-6-fluoro-1,2-benzisoxazole, m.p. 119°–121° C.
(160) 4-(2-(5-acetylaminomethyl-2-thienyl)ethyl)-N-cyclohexyl-1-piperazinecarboxamide, m.p. 188°–190° C.
(161) 4-(2-(5-acetylaminomethyl-2-thienyl)ethyl)-N-phenyl-1-piperazinecarboxamide, m.p. 182°–184° C.
(162) 3-(1-(2-(5-phenylacetylaminomethyl-2-thienyl)ethyl)piperidin-4-yl)-6-fluoro-1,2-benzisoxazole, m.p. 117°–119° C.
(163) 4-(2-(5-acetylaminomethyl-2-thienyl)ethyl)-N-ethyl-1-piperazinecarboxamide, m.p. 155°–157° C.
(164) 3-(1-(2-(5-aminomethyl-2-thienyl)ethyl)piperidin-4-yl)-6-fluoro-1,2-benzisoxazole, m.p. 80°–82° C.
(165) 3-(1-(4-(5-aminomethyl-2-thienyl)butyl)piperidin-4-yl)-6-fluoro-1,2-benzisoxazole hydrochloride ½ hydrate, m.p. 255° C. or above
(166) 3-(1-(2-(5-dimethylaminomethyl-2-thienyl)ethyl)piperidin-4-yl)-6-fluoro-1,2-benzisoxazole oxalate, m.p. 122°–125° C.

FORMULATION EXAMPLE

Tablets containing 10 mg of the compound of the formula (I) can be prepared according to the following formulation.

| | |
|---|---|
| Compound of formula (I) | 10.0 mg |
| Lactose | 58.5 mg |
| Corn starch | 25.0 mg |
| Crystalline cellulose | 20.0 mg |
| Polyvinylpyrrolidone K-30 | 2.0 mg |
| Talc | 4.0 mg |
| Magnesium stearate | 0.5 mg |
| | 120.0 mg |

The compound of the formula (I) is pulverized in an atomizer to give a fine powder having an average particle size of 10 μ or less. The powder was thoroughly mixed with lactose, corn starch, and crystalline cellulose in a kneader, and kneaded with polyvinylpyrrolidone paste. The kneaded substance is passed through a 20 mesh sieve, dried at 50° C., and passed through a 24 mesh sieve. Talc and magnesium stearate are mixed in, and 120.0 mg tablets are obtained with a pounder having a diameter of 8 mm. The obtained tablets may be coated with sugar or a film where necessary.

While the present invention has been adequately and sufficiently described in the foregoing specification and examples, it should be understood that the present invention is susceptible to various changes and modifications falling within the spirit and scope of the invention.

What is claimed is:

1. A thiophene compound of the formula

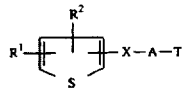

wherein
$R^1$ and $R^2$ are the same or different and each is
(1) hydrogen,
(2) halogen,
(3) nitro,
(4) amino,
(5) cyano,
(6) alkyl of 1 to 8 carbon atoms,
(7) mono- or di-alkylamino wherein the alkyl moiety is of 1 to 4 carbon atoms,
(8) formyl,
(9) —COOR$^3$ wherein R$^3$ is hydrogen, alkyl of 1 to 8 carbon atoms or an ester residue hydrolyzable in the body,
(10) alkoxy of 1 to 8 carbon atoms,
(11) hydroxyalkyl of 1 to 4 carbon atoms,
(12) haloalkyl of 1 to 4 carbon atoms,
(13) haloalkoxy of 1 to 4 carbon atoms,
(14) alkanoyl of 2 to 5 carbon atoms,
(15) benzoyl,
(16) naphthoyl,
(17) phenylalkanoyl wherein the alkanoyl moiety has 2 to 5 carbon atoms,
(18) alkanoyloxyalkyl wherein the alkanoyl moiety has 1 to 5 carbon atoms and the alkyl moiety has 1 to 4 carbon atoms,
(19) benzoyloxyalkyl wherein the alkyl moiety has 1 to 4 carbon atoms,
(20) formylamino,
(21) alkanoylamino having 2 to 5 carbon atoms,
(22) phenylalkanoylamino wherein the alkanoyl moiety has 2 to 5 carbon atoms,
(23) benzoylamino,
(24) naphthoylamino,
(25) formylaminoalkyl wherein the alkyl moiety has 1 to 4 carbon atoms,
(26) alkanoylaminoalkyl wherein the alkanoyl moiety has 2 to 5 carbon atoms and the alkyl moiety has 1 to 4 carbon atoms,
(27) haloalkanoylaminoalkyl wherein the alkanoyl moiety has 2 to 5 carbon atoms and the alkyl moiety has 1 to 4 carbon atoms,
(28) phenylalkanoylaminoalkyl wherein the alkanoyl moiety has 2 to 5 carbon atoms and the alkyl moiety has 1 to 4 carbon atoms,
(29) benzoylaminoalkyl wherein the alkyl moiety has 1 to 4 carbon atoms,
(30) phenylalkyl wherein the alkyl moiety has 1 to 6 carbon atoms,
(31) carbamoyl,
(32) carbamoyl mono- or di-substituted by alkyl of 1 to 4 carbon atoms, cyclohexyl, phenyl or benzyl,
(33) carbamoylalkyl wherein the alkyl moiety has 1 to 4 carbon atoms,
(34) carbamoylalkyl mono- or di-substituted by alkyl of 1 to 4 carbon atoms or benzyl and the alkyl moiety having 1 to 4 carbon atoms,
(35) aminoalkyl wherein the alkyl moiety has 1 to 4 carbon atoms,
(36) aminoalkyl mono- or di-substituted by alkyl of 1 to 4 carbon atoms and the alkyl moiety having 1 to 4 carbon atoms,
(37) alkylsulfonylaminoalkyl wherein the alkyl moieties respectively have 1 to 4 carbon atoms,
(38) hydroxyiminoalkyl wherein the alkyl moiety has 1 to 4 carbon atoms, or
(39) alkoxyiminoalkyl wherein the alkoxy and alkyl moieties respectively have 1 to 4 carbon atoms;

X is
(1) —S(O)$_n$— wherein n is 0, 1 or 2,
(2) —CO—,
(3) —CH(OR$^{10}$)— wherein R$^{10}$ is hydrogen, alkyl of 1 to 8 carbon atoms, alkanoyl of 2 to 5 carbon atoms or benzoyl,
(4) —CH$_2$—;

A is alkylene of 1 to 10 carbon atoms; and

T is

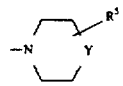

wherein
R$^5$ is hydrogen, and

Y is
(a) C(R⁶)(R⁷) wherein
R⁶ is hydrogen, and
R⁷ is 1,2-benzisothiazol or 1,2-benzisoxazol which groups are unsubstituted or are substituted by 1 to 3 substituents selected from the group consisting of halogen, nitro, amino, cyano, haloalkyl of 1 to 4 carbon atoms, hydroxy, alkyl of 1 to 4 carbon atoms, alkoxy of 1 to 4 carbon atoms, alkenyl of 2 to 4 carbon atoms and phenyl, or R⁶ and R⁷ taken together form
(1) diphenylmethylene,
(2) bis(4-fluorophenyl)methylene, or
(3) bis(4-chlorophenyl)methylene, or
(b) N—R⁸ wherein R⁸ is phenyl, pyrimidinyl, 1,2-benzisothiazol or 1,2-benzisoxazol which groups are unsubstituted or are substituted by 1 to 3 substituents selected from the group consisting of halogen, nitro, amino, cyano, haloalkyl of 1 to 4 carbon atoms, hydroxy, alkyl of 1 to 4 carbon atoms, alkoxy of 1 to 4 carbon atoms, alkenyl of 2 to 4 carbon atoms and phenyl;
with the proviso that when
X is —CO—, —CH(OR¹⁰)—, —CH₂—, —C(=NOR¹¹)— or —CH(NH₂) wherein R¹⁰ and R¹¹ are as defined above, and
Y is one of the following
(i) C(R⁶)(R⁷) wherein R⁶ and R⁷ together form diphenylmethylene, bis(4-fluorophenyl)methylene or bis(4-chlorophenyl)methylene, or
(ii) N—R⁸ wherein R⁸ is phenyl which is unsubstituted or is substituted by 1 to 3 substituents selected from the group consisting of halogen, nitro, amino, cyano, haloalkyl of 1 to 4 carbon atoms, hydroxy, alkyl of 1 to 4 carbon atoms, alkoxy of 1 to 4 carbon atoms, alkenyl of 2 to 4 carbon atoms, and phenyl
then, in such case, at least one of R¹ and R² is a group other than hydrogen, halogen, nitro, alkyl of 1 to 8 carbon atoms and alkoxy of 1 to 8 carbon atoms, or a pharmaceutically acceptable salt of said thiophene compound.

2. A thiophene compound according to claim 1, wherein R¹ is
(1) amino,
(2) cyano,
(3) amino mono- or di-substituted by alkyl having 1 to 4 carbon atoms,
(4) formyl,
(5) —COOR³ wherein R³ is hydrogen, alkyl of 1 to 8 carbon atoms or an ester residue hydrolyzable in the body,
(6) hydroxyalkyl having 1 to 4 carbon atoms,
(7) haloalkyl having 1 to 4 carbon atoms,
(8) haloalkoxy having 1 to 4 carbon atoms,
(9) alkanoyl having 2 to 5 carbon atoms,
(10) benzoyl,
(11) naphthoyl,
(12) phenylalkanoyl wherein the alkanoyl moiety has 2 to 5 carbon atoms,
(13) alkanoyloxyalkyl wherein the alkanoyl moiety has 1 to 5 carbon atoms and the alkyl moiety has 1 to 4 carbon atoms,
(14) benzoyloxyalkyl wherein the alkyl moiety has 1 to 4 carbon atoms,
(15) formylamino,
(16) alkanoylamino having 2 to 5 carbon atoms,
(17) phenylalkanoylamino wherein the alkanoyl moiety has 2 to 5 carbon atoms,
(18) benzoylamino,
(19) naphthoylamino,
(20) formylaminoalkyl wherein the alkyl moiety has 1 to 4 carbon atoms,
(21) alkanoylaminoalkyl wherein the alkanoyl moiety has 2 to 5 carbon atoms and the alkyl moiety has 1 to 4 carbon atoms,
(22) haloalkanoylaminoalkyl wherein the alkanoyl moiety has 2 to 5 carbon atoms and the alkyl moiety has 1 to 4 carbon atoms,
(23) phenylalkanoylaminoalkyl wherein the alkanoyl moiety has 2 to 5 carbon atoms and the alkyl moiety has 1 to 4 carbon atoms,
(24) benzoylaminoalkyl wherein the alkyl moiety has 1 to 4 carbon atoms,
(25) phenylalkyl wherein the alkyl moiety has 1 to 6 carbon atoms,
(26) carbamoyl,
(27) carbamoyl mono- or di-substituted by alkyl having 1 to 4 carbon atoms, cyclohexyl, phenyl or benzyl,
(28) carbamoylalkyl wherein the alkyl moiety has 1 to 4 carbon atoms,
(29) carbamoylalkyl mono- or di-substituted by an alkyl having 1 to 4 carbon atoms or benzyl, and the alkyl moiety having 1 to 4 carbon atoms,
(30) aminoalkyl wherein the alkyl moiety has 1 to 4 carbon atoms,
(31) aminoalkyl mono- or di-substituted by alkyl having 1 to 4 carbon atoms, and the alkyl moiety having 1 to 4 carbon atoms,
(32) alkylsulfonylaminoalkyl wherein the alkyl moieties respectively have 1 to 4 carbon atoms,
(33) hydroxyiminoalkyl wherein the alkyl moiety has 1 to 4 carbon atoms, or
(34) alkoxyiminoalkyl wherein the alkoxy moiety and the alkyl moiety respectively have 1 to 4 carbon atoms;
R² is
(1) hydrogen,
(2) halogen,
(3) nitro,
(4) cyano, or
(5) alkyl having 1 to 8 carbon atoms;
X is
(1) —S(O)ₙ— wherein n is 0, 1 or 2,
(2) —CO—,
(3) —CH(OR¹⁰)— wherein R¹⁰ is hydrogen, alkyl having 1 to 8 carbon atoms, alkanoyl having 2 to 5 carbon atoms or benzoyl, or
(4) —CH₂—;
A is alkylene having 1 to 10 carbon atoms; and
T is

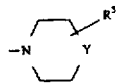

wherein

R⁵ is hydrogen, and

Y is (a) C(R⁶) (R⁷) wherein

R⁶ is hydrogen, and

R⁷ is 1,2-benzisothiazol or 1,2-benzisoxazol which groups are unsubstituted or are substituted by 1 to 3 substituents selected from the group consisting of halogen, nitro, amino, cyano, haloalkyl having 1 to 4 carbon atoms, hydroxy, alkyl having 1 to 4 carbon atoms, alkoxy having 1 to 4 carbon atoms, alkenyl having 2 to 4 carbon atoms and phenyl, or R⁶ and R⁷ taken together form (1) diphenylmethylene, (2) bis(4-fluorophenyl)methylene or (3) bis-(4-chlorophenyl)methylene, or (b) N—R⁸ wherein R⁸ is phenyl, pyrimidinyl, 1,2-benzisothiazol or 1,2-benzisoxazol which groups are unsubstituted or are substituted by 1 to 3 substituents selected from the group consisting of halogen, nitro, amino, cyano, haloalkyl having 1 to 4 carbon atoms, hydroxy, alkyl having 1 to 4 carbon atoms, alkoxy having 1 to 4 carbon atoms, alkenyl having 2 to 4 carbon atoms and phenyl;

or a pharmaceutically acceptable salt of said thiophene compound.

3. A thiophene compound according to claim 1, wherein;

R¹ is (1) formyl, (2) hydroxyalkyl having 1 to 4 carbon atoms, (3) haloalkyl having 1 to 4 carbon atoms, (4) alkanoyl having 2 to 5 carbon atoms, (5) benzoyl, (6) naphthoyl, (7) alkanoylamino having 2 to 5 carbon atoms, (8) alkanoylaminoalkyl wherein the alkanoyl moiety has 2 to 5 carbon atoms and the alkyl moiety has 1 to 4 carbon atoms, (9) haloalkanoylaminoalkyl wherein the alkanoyl moiety has 2 to 5 carbon atoms and the alkyl moiety has 1 to 4 carbon atoms,

(10) phenylalkanoylaminoalkyl wherein the alkanoyl moiety has 2 to 5 carbon atoms and the alkyl moiety has 1 to 4 carbon atoms,

(11) benzoylaminoalkyl wherein the alkyl moiety has 1 to 4 carbon atoms,

(12) carbamoylalkyl wherein the alkyl moiety has 1 to 4 carbon atoms,

(13) carbamoylalkyl mono- or di-substituted by alkyl having 1 to 4 carbon atoms or benzyl, and the alkyl moiety has 1 to 4 carbon atoms,

(14) aminoalkyl wherein the alkyl moiety has 1 to 4 carbon atoms,

(15) aminoalkyl mono- or di-substituted by an alkyl having 1 to 4 carbon atoms, and the alkyl moiety having 1 to 4 carbon atoms,

(16) alkylsulfonylaminoalkyl wherein the alkyl moieties respectively have 1 to 4 carbon atoms, or

(17) hydroxyiminoalkyl wherein the alkyl moiety has 1 to 4 carbon atoms;

R² is (1) hydrogen, (2) halogen, (3) nitro, (4) cyano, or (5) alkyl having 1 to 8 carbon atoms;

X is (1) —S(O)ₙ— wherein n is 0, 1 or 2, (2) —CO—, (3) —CH(OR¹⁰)— wherein R¹⁰ is hydrogen, alkyl having 1 to 8 carbon atoms, alkanoyl having 2 to 5 carbon atoms or benzoyl, or (4) —CH₂—;

A is alkylene having 1 to 10 carbon atoms; and

T is

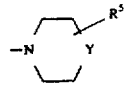

wherein R⁵ is hydrogen,

Y is (a) C(R⁶) (R⁷) wherein

R⁶ is hydrogen, and R⁷ is 1,2-benzisothiazol or 1,2-benzisoxazol which groups are unsubstituted or are substituted by 1 to 3 substituents selected from the group consisting of halogen, nitro, amino, cyano, haloalkyl having 1 to 4 carbon atoms, hydroxy, alkyl having 1 to 4 carbon atoms, alkoxy having 1 to 4 carbon atoms, alkenyl having 2 to 4 carbon atoms and phenyl, or R⁶ and R⁷ taken together form (1) diphenylmethylene, (2) bis(4-fluorophenyl)methylene, or (3) bis(4-chlorophenyl)methylene), or (b) N—R⁸ wherein R⁸ is phenyl, pyrimidinyl, 1,2-benzisothiazol or 1,2-benzisoxazol which groups are unsubstituted or are substituted by 1 to 3 substituents selected from the group consisting of halogen, nitro, amino, cyano, haloalkyl having 1 to 4 carbon atoms, hydroxy, alkyl having 1 to 4 carbon atoms, alkoxy having 1 to 4 carbon atoms, alkenyl having 2 to 4 carbon atoms and phenyl;

or a pharmaceutically acceptable salt of said thiophene compound.

4. A thiophene compound according to claim 1, wherein;

R¹ is (1) alkanoyl having 2 to 5 carbon atoms, (2) alkanoylamino having 2 to 5 carbon atoms, (3) alkanoylaminoalkyl wherein the alkanoyl moiety has 2 to 5 carbon atoms and the alkyl moiety has 1 to 4 carbon atoms, (4) benzoylaminoalyl wherein the alkyl moiety has 1 to 4 carbon atoms, or (5) alkylsulfonylaminoalkyl wherein the alkyl moieties respectively have 1 to 4 carbon atoms;

R² is (1) hydrogen, (2) halogen, or (3) alkyl having 1 to 8 carbon atoms;

X is (1) —S(O)ₙ— wherein n is 0, 1 or 2, (2) —CO—, or (3) —CH₂—;

A is alkylene having 1 to 10 carbon atoms; and
T is $$-N\underset{\diagdown\_\diagup}{\overset{\diagup\ \ \ \diagdown}{\phantom{X}}}\overset{R^5}{\underset{Y}{\phantom{X}}}$$

wherein
R⁵ is hydrogen,
Y is
(a) C(R⁶)(R⁷) wherein
 R⁶ is hydrogen, and
 R⁷ is 1,2-benzisothiazol or 1,2-benzisoxazol which groups are unsubstituted or are substituted by 1 to 3 halogen substituents, or R⁶ and R⁷ taken together form bis (4-fluorophenyl) methylene, or
(b) N—R⁸ wherein R⁸ is phenyl, pyrimidinyl, 1,2-benzisothiazol or 1,2-benzisoxazol which groups are unsubstituted or are substituted by 1 to 3 substituents selected from the group consisting of halogen, haloalkyl having 1 to 4 carbon atoms, alkyl having 1 to 4 carbon atoms and alkoxy having 1 to 4 carbon atoms; or a pharmaceutically acceptable salt of said thiophene compound.

5. A thiophene compound according to claim 1, said compound being one selected from the group consisting of
3-(4-(3-((5-acetyl-2-thienyl)thio)propyl)-1-piperazinyl)-1,2-benzisothiazole,
3-(1-(3-((5-acetyl-2-thienyl)thio)propyl)piperidin-4-yl)-6-fluoro-1,2-benzisoxazole,
3-(1-(3-((5-acetylamino-2-thienyl)thio)propyl)piperidin-4-yl)-6-fluoro-1,2-benzisoxazole,
3-(1-(3-((5-acetylaminomethyl-2-thienyl)thio)propyl)piperidin-4-yl)-6-fluoro-1,2-benzisoxazole,
3-(1-(4-(5-acetylaminomethyl-2-thienyl-4-oxobutyl)piperidin-4-yl)-6-fluoro-1,2-benzisoxazole,
3-(1-(4-(5-acetylaminomethyl-2-thienyl)butyl)piperidin-4-yl)6-fluoro-1,2-benzisoxazole,
3-(1-(2-(5-acetylaminomethyl-2-thienyl)ethyl)piperidin-4-yl)6-fluoro-1,2-benzisoxazole,
3-(1-(2-(5-acetylaminomethyl-4-methyl-2-thienyl)ethyl)piperidin-4-yl)-6-fluoro-1,2-benzisoxazole,
3-(1-(2-(5-acetylaminomethyl-2-methyl-3-thienyl)ethyl)piperidin-4-yl)-6-fluoro-1,2-benzisoxazole,
3-(1-(2-(5-2-acetaminoethyl)-2-thienyl)ethyl)piperidin-4-yl)-6-fluoro-1,2-benzisoxazole,
3-(1-(2-(5-(2-acetylaminoethyl)-4-bromo-2-thienyl)ethyl)piperidin-4-yl)-6-fluoro-1,2-benzisoxazole,
3-(1-(4-(5-acetylamino-2-thienyl)butyl)piperidin-4-yl)-6-fluoro-1,2-benzisoxazole,
1-(4-((5-acetyl-2-thienyl)thio)butyl)-4-(2-pyrimidinyl)piperazine,
1-(3-((5-acetyl-2-thienyl)thio)propyl)-4-(2,3-dimethylphenyl)piperazine,
1-(3-((5-acetylamino-2-thienyl)thio)propyl)-4-(3-trifluoromethylphenyl)piperazine,
1-(3-((5-acetylamino-2-thienyl)thio)propyl)-4-(2methoxyphenyl)piperazine,
1-(3-((5-acetyl-2-thienyl)thio)propyl)-4-(3-chlorophenyl)piperazine,
3-(1-(2-((5-acetyl-2-thienyl)thio)ethyl)piperidin-4-yl)-6-fluoro-1,2-benzisoxazole,
3-(1-(4-((5-acetyl-2-thienyl)thio)butyl)piperidin-4-yl)-6-fluoro-1,2-benzisoxazole,
1-(6-((5-acetyl-2-thienyl)thio)hexyl)-4-(2-methoxyphenyl)piperazine,
1-(3-((5-acetylamino-2-thienyl)thio)propyl)-4-(2,3-dimethylphenyl)piperazine,
1-(4-(5-acetylaminomethyl-2-thienyl)-4-oxobutyl)-4-(3-trifluoromethylphenyl)piperazine,
3-(1-(4-(5-acetylaminomethyl-2-thienyl)-4-oxobutyl)piperazin-4-yl)-1,2-benzisothiazole,
3-(1-(4-(5-acetylaminomethyl-2-thienyl)butyl)piperazin-4-yl)-1,2-benzisothiazole,
3-(1-(4-(5-(2-benzoylaminomethyl)-2-thienyl)-4-oxobutyl)piperazin-4-yl)-1,2-benzisothiazole,
3-(1-(4-(5-propionylaminomethyl)-2-thienyl)-4-oxobutyl)piperazin-4-yl)-1,2-benzisothiazole,
3-(1-(4-(5-mesylaminomethyl)-2-thienyl)-4-oxobutyl)piperazin-4-yl)-1,2-benzisothiazole,
3-(1-(6-(5-acetylaminomethyl-2-thienyl)-6-oxohexyl)piperidin-4-yl)-6-fluoro-1,2-benzisoxazole,
3-(4-(2-(5-acetylaminomethyl)-2-thienyl)ethyl)piperazin-1-yl)-1,2-benzisoxazole, and
1-(2-(5-acetylaminomethyl-2-thienyl)ethyl)-4-(bis(4-fluorophenyl)methylene)piperidine, and a pharmaceutically acceptable salt of said compound.

6. A thiophene compound according to claim 1, wherein:
R¹ is
 (1) alkanoyl having 2 to 5 carbon atoms,
 (2) alkanoylamino having 2 to 5 carbon atoms, or
 (3) alkanoylaminoalkyl wherein the alkanoyl moiety has 2 to 5 carbon atoms and the alkyl moiety has 1 to 4 carbon atoms;
R² is
 (1) hydrogen,
 (2) halogen, or
 (3) alkyl having 1 to 4 carbon atoms;
X is
 (1) —S(O)$_n$— wherein n is 0, 1 or 2,
 (2) —CO—, or
 (3) —CH$_2$—;
A is alkylene having 1 to 6 carbon atoms; and
T is $$-N\underset{\diagdown\_\diagup}{\overset{\diagup\ \ \ \diagdown}{\phantom{X}}}\overset{R^5}{\underset{Y}{\phantom{X}}}$$

wherein R⁵ is hydrogen, and
Y is C(R⁶)(R⁷) wherein
 R⁶ is hydrogen, and
 R⁷ is 1,2-benzisothiazol or 1,2-benzisoxazol which groups are unsubstituted or are substituted by 1 to 3 halogen substituents; or a pharmaceutically acceptable salt of said thiophene compound.

7. A thiophene compound according to claim 1, wherein:
R¹ is acetyl, acetylamino, acetylaminomethyl or 2-acetylaminoethyl;
R² is hydrogen, halogen or methyl;
X is
 (1) —S(O)$_n$— wherein n is 0, 1 or 2,
 (2) —CO—, or
 (3) —CH$_2$—;
A is methylene, ethylene or trimethylene; and
T is 4-(1,2-benzisothiazol-3-yl)-1-piperadinyl or 4-(6-fluoro-1,2-benzisoxazol-3-yl)piperidino;
or a pharmaceutically acceptable salt of said thiophene compound.

8. A thiophene compound according to claim 1, said compound being one selected from the group consisting of 3-(4-(3-((5-acetyl-2-thienyl)thio)propyl)-1-piperazinyl)-1,2-benzisothiazole, 3-(1-(3-((5-acetyl-2-thienyl)thio)propyl)piperidin-4-yl)-6-fluoro-1,2-benzisoxazole, 3-(1-(3-((5-acetylamino-2-thienyl)thio)propyl)piperidin-4-yl)6-fluoro-1,2-benzisoxazole, 3-(1-(3-((5-acetylaminomethyl-2-thienyl)thio)propyl)piperidin-4-yl)-6-fluoro-1,2-benzisoxazole, 3-(1-(4-(5-acetylaminomethyl-2-thienyl)-4-oxobutyl)piperidin4-yl)-6-fluoro-1,2-benzisoxazole, 3-(1-(4-(5-acetylaminomethyl-2-thienyl)butyl)piperidin-4-yl)-6-fluoro-1,2-benzisoxazole, 3-(1-(2-(5-acetylaminomethyl-2-thienyl)ethyl)piperidin-4-yl)-6-fluoro-1,2-benzisoxazole, 3-(1-(2-(5-acetylaminomethyl-4-methyl-2-thienyl)ethyl)piperidin-4-yl)-6-fluoro-1,2-benzisoxazole, 3-(1-(2-(5-acetylaminomethyl-2-methyl-3-thienyl)ethyl)piperidin-4-yl)-6-fluoro-1,2-benzisoxazole, 3-(1-(2-(5-(2-acetylaminoethyl)-2-thienyl)ethyl)piperidin-4-yl)-6-fluoro-1,2-benzisoxazole, 3-(i-(2-(5-(2-acetylaminoethyl)-4-bromo-2-thienyl)ethyl)piperidin-4-yl)-6-fluoro-1,2-benzisoxazole, and 3-(1-(4-(5-acetylamino-2-thienyl)butyl)piperidin-4-yl)-6-fluoro-1,2-benzisoxazole, and a pharmaceutically acceptable salt thereof.

9. A pharmaceutical composition for the use as an antipsychotic or an antianxiety agent comprising a therapeutically effective amount of a compound of claim 1 or a pharmaceutically acceptable salt thereof and pharmaceutically acceptable carrier therefor.

* * * * *